US012366577B2

(12) United States Patent
Gaylord et al.

(10) Patent No.: US 12,366,577 B2
(45) **Date of Patent: *Jul. 22, 2025**

(54) FLUORESCENT METHODS AND MATERIALS FOR DIRECTED BIOMARKER SIGNAL AMPLIFICATION

(71) Applicant: SIRIGEN II LIMITED, Workingham (GB)

(72) Inventors: Brent S. Gaylord, San Diego, CA (US); Janice W. Hong, San Diego, CA (US); Tsu-Ju Fu, Poway, CA (US); ChengJun Sun, Goleta, CA (US); Russell A. Baldocchi, Encinitas, CA (US)

(73) Assignee: SIRIGEN II LIMITED, Workingham (GB)

( * ) Notice: Subject to any disclaimer, the term of this patent is extended or adjusted under 35 U.S.C. 154(b) by 148 days.

This patent is subject to a terminal disclaimer.

(21) Appl. No.: 17/531,027

(22) Filed: Nov. 19, 2021

(65) Prior Publication Data

US 2022/0082568 A1 Mar. 17, 2022

Related U.S. Application Data

(63) Continuation of application No. 16/528,469, filed on Jul. 31, 2019, now Pat. No. 11,209,438, which is a (Continued)

(51) Int. Cl.

*G01N 33/58* (2006.01)
*C08G 61/02* (2006.01)
(Continued)

(52) U.S. Cl.

CPC ........... *G01N 33/582* (2013.01); *C08G 61/02* (2013.01); *C08G 61/12* (2013.01); *G01N 33/542* (2013.01);
(Continued)

(58) Field of Classification Search

CPC .................... C08G 61/12; C08G 61/02; C08G 2261/3142; C08G 2261/3241;
(Continued)

(56) References Cited

U.S. PATENT DOCUMENTS

| | | | |
|---|---|---|---|
| 4,486,530 A | 12/1984 | David et al. | |
| 5,143,854 A | 9/1992 | Pirrung et al. | |

(Continued)

FOREIGN PATENT DOCUMENTS

| | | |
|---|---|---|
| CA | 2365814 | 6/2003 |
| CN | 1594314 | 3/2005 |

(Continued)

OTHER PUBLICATIONS

Sumranjit, et al. "Conjugated Organic Molecules as Models for Potential Sensors", Univ. of Mass, Dept. of Chemistry, 2008, 137 pages.

(Continued)

*Primary Examiner* — Shafiqul Haq
(74) *Attorney, Agent, or Firm* — Travis Young; Bret E. Field; BOZICEVIC, FIELD & FRANCIS LLP

(57) ABSTRACT

Methods and compositions are provided that include a multichromophore and/or multichromophore complex for identifying a target biomolecule. A sensor biomolecule, for example, an antibody can be covalently linked to the multichromophore. Additionally, a signaling chromophore can be covalently linked to the multichromophore. The arrangement is such that the signaling chromophore is capable of receiving energy from the multichromophore upon excitation of the multichromophore. Since the sensor biomolecule is capable of interacting with the target biomolecule, the multichromophore and/or multichromophore complex can provide enhanced detection signals for a target biomolecule.

14 Claims, 22 Drawing Sheets

$R^1$ = solubilizing group, such as $(CH_2)_n\overset{\oplus}{N}Me_3\overset{\ominus}{Br}$

Related U.S. Application Data continuation of application No. 16/154,541, filed on Oct. 8, 2018, now Pat. No. 10,859,578, which is a continuation of application No. 15/799,969, filed on Oct. 31, 2017, now Pat. No. 10,641,777, which is a continuation of application No. 15/162,436, filed on May 23, 2016, now Pat. No. 10,126,302, which is a continuation of application No. 14/307,258, filed on Jun. 17, 2014, now Pat. No. 9,383,353, which is a continuation of application No. 13/195,747, filed on Aug. 1, 2011, now Pat. No. 8,802,450, which is a continuation of application No. 11/868,870, filed on Oct. 8, 2007, now Pat. No. 8,158,444.

(60) Provisional application No. 60/828,615, filed on Oct. 6, 2006.

(51) Int. Cl.
*C08G 61/12* (2006.01)
*G01N 33/542* (2006.01)
*H10K 85/10* (2023.01)

(52) U.S. Cl.
CPC ................ *C08G 2261/3142* (2013.01); *C08G 2261/3221* (2013.01); *C08G 2261/3241* (2013.01); *C08G 2261/3246* (2013.01); *C08G 2261/522* (2013.01); *C08G 2261/78* (2013.01); *C08G 2261/94* (2013.01); *H10K 85/115* (2023.02); *Y10T 436/13* (2015.01)

(58) Field of Classification Search
CPC ...... C08G 2261/522; C08G 2261/3246; C08G 2261/78; C08G 2261/3221; C08G 2261/94; G01N 33/542; G01N 33/582; Y10T 436/13; H10K 85/115
See application file for complete search history.

(56) References Cited

U.S. PATENT DOCUMENTS

| | | | | |
|---|---|---|---|---|
| 5,288,514 | A | 2/1994 | Ellman | |
| 5,384,261 | A | 1/1995 | Winkler et al. | |
| 5,424,186 | A | 6/1995 | Fodor et al. | |
| 5,478,741 | A * | 12/1995 | Maret | C07K 14/445 530/391.1 |
| 5,677,195 | A | 10/1997 | Winkler et al. | |
| 5,807,974 | A | 9/1998 | Kim | |
| 5,990,479 | A | 11/1999 | Weiss et al. | |
| 6,263,286 | B1 | 7/2001 | Gilmanshin et al. | |
| 6,280,933 | B1 | 8/2001 | Glazer et al. | |
| 6,350,431 | B1 | 2/2002 | Snow et al. | |
| 6,808,542 | B2 | 10/2004 | Nyguyen et al. | |
| 6,951,682 | B1 | 10/2005 | Zebala | |
| 6,998,241 | B2 | 2/2006 | Boga | |
| 7,141,437 | B2 | 11/2006 | Dvornic et al. | |
| 7,144,950 | B2 | 12/2006 | Bazan et al. | |
| 7,208,122 | B2 | 4/2007 | Swager et al. | |
| 7,214,489 | B2 | 5/2007 | Bazan | |
| 7,241,512 | B2 | 7/2007 | Li et al. | |
| 7,253,287 | B1 | 8/2007 | Belfield et al. | |
| 7,270,956 | B2 | 9/2007 | Bazan et al. | |
| 7,282,514 | B1 | 10/2007 | Belfield et al. | |
| 7,629,448 | B2 | 12/2009 | Bazan et al. | |
| 7,666,594 | B2 | 2/2010 | Bazan | |
| 7,811,755 | B2 | 10/2010 | Bazan et al. | |
| 7,897,684 | B2 | 3/2011 | Bazan et al. | |
| 7,914,984 | B2 | 3/2011 | Bazan et al. | |
| 8,101,416 | B2 | 1/2012 | Bazan et al. | |
| 8,110,673 | B2 | 2/2012 | Bazan et al. | |
| 8,158,444 | B2 | 4/2012 | Gaylord et al. | |
| 8,227,187 | B2 | 7/2012 | Bazan et al. | |
| 8,309,672 | B2 | 11/2012 | Bazan et al. | |
| 8,338,532 | B2 | 12/2012 | Bazan et al. | |
| 8,354,239 | B2 | 1/2013 | Gaylord et al. | |
| 8,362,193 | B2 | 1/2013 | Gaylord et al. | |
| 8,455,613 | B2 | 6/2013 | Gaylord et al. | |
| 8,546,081 | B2 | 10/2013 | Bazan et al. | |
| 8,575,303 | B2 | 11/2013 | Gaylord et al. | |
| 8,617,814 | B2 | 12/2013 | Bazan et al. | |
| 8,669,055 | B2 | 3/2014 | Bazan et al. | |
| 8,759,444 | B2 | 6/2014 | Bazan et al. | |
| 8,802,450 | B2 | 8/2014 | Gaylord et al. | |
| 8,835,113 | B2 | 9/2014 | Bazan et al. | |
| 8,841,072 | B2 | 9/2014 | Bazan et al. | |
| 8,969,509 | B2 | 3/2015 | Liu et al. | |
| 8,993,335 | B2 | 3/2015 | Bazan et al. | |
| 9,085,799 | B2 | 7/2015 | Bazan et al. | |
| 9,139,869 | B2 | 9/2015 | Gaylord et al. | |
| 9,159,465 | B2 | 10/2015 | Bazan et al. | |
| 9,371,559 | B2 | 6/2016 | Bazan et al. | |
| 9,383,353 | B2 | 7/2016 | Gaylord et al. | |
| 9,547,008 | B2 | 1/2017 | Gaylord et al. | |
| 9,722,252 | B2 | 8/2017 | Liu et al. | |
| 10,126,302 | B2 * | 11/2018 | Gaylord | C08G 61/12 |
| 10,288,620 | B2 | 5/2019 | Gaylord et al. | |
| 10,458,989 | B2 * | 10/2019 | Gaylord | C09D 165/00 |
| 10,481,161 | B2 * | 11/2019 | Gaylord | G01N 33/582 |
| 10,641,775 | B2 * | 5/2020 | Gaylord | G01N 33/582 |
| 10,641,777 | B2 * | 5/2020 | Gaylord | G01N 33/582 |
| 10,859,578 | B2 | 12/2020 | Gaylord et al. | |
| 10,955,417 | B2 * | 3/2021 | Gaylord | C12Q 1/6818 |
| 10,962,546 | B2 * | 3/2021 | Gaylord | G01N 33/582 |
| 11,209,438 | B2 * | 12/2021 | Gaylord | C08G 61/02 |
| 11,639,937 | B2 * | 5/2023 | Gaylord | G01N 33/582 528/322 |
| 2003/0087311 | A1 | 5/2003 | Wolf | |
| 2004/0009506 | A1 | 1/2004 | Stephan et al. | |
| 2004/0023248 | A1 | 2/2004 | O'Malley | |
| 2004/0023317 | A1 | 2/2004 | Motamedi et al. | |
| 2004/0142344 | A1 | 7/2004 | Bazan et al. | |
| 2004/0219556 | A1 | 11/2004 | Bazan et al. | |
| 2005/0003386 | A1 | 1/2005 | Bazan et al. | |
| 2005/0059168 | A1 | 3/2005 | Bazan et al. | |
| 2005/0196775 | A1 | 9/2005 | Swager et al. | |
| 2006/0073607 | A1 | 4/2006 | Rose et al. | |
| 2006/0127929 | A1 | 6/2006 | Swager et al. | |
| 2006/0160109 | A1 | 7/2006 | Macdonald et al. | |
| 2006/0175193 | A1 | 8/2006 | Inganas et al. | |
| 2006/0183140 | A1 | 8/2006 | Bazan et al. | |
| 2006/0204984 | A1 | 9/2006 | Bazan et al. | |
| 2006/0216734 | A1 | 9/2006 | Bazan et al. | |
| 2006/0216759 | A1 | 9/2006 | Naasani | |
| 2007/0178470 | A1 | 8/2007 | Bissonnette | |
| 2007/0281289 | A1 | 12/2007 | Moon | |
| 2008/0038751 | A1 | 2/2008 | Asberg et al. | |
| 2008/0064042 | A1 | 3/2008 | Bazan et al. | |
| 2008/0293164 | A1 | 11/2008 | Gaylord | |
| 2009/0230362 | A1 | 9/2009 | Bazan et al. | |
| 2010/0136702 | A1 | 6/2010 | Bazan et al. | |
| 2011/0256549 | A1 | 10/2011 | Gaylord et al. | |
| 2011/0256550 | A1 | 10/2011 | Gaylord et al. | |
| 2011/0257374 | A1 | 10/2011 | Gaylord et al. | |
| 2012/0028828 | A1 | 2/2012 | Gaylord et al. | |
| 2012/0029155 | A1 | 2/2012 | Gaylord et al. | |
| 2012/0252986 | A1 | 10/2012 | Liu et al. | |
| 2013/0190193 | A1 | 7/2013 | Bazan et al. | |
| 2015/0226746 | A1 | 8/2015 | Bazan et al. | |
| 2016/0266131 | A1 | 9/2016 | Liang et al. | |
| 2016/0266132 | A1 | 9/2016 | Gaylord et al. | |
| 2016/0341720 | A1 | 11/2016 | Bazan et al. | |
| 2016/0349267 | A1 | 12/2016 | Gaylord et al. | |
| 2017/0115298 | A1 | 4/2017 | Gaylord et al. | |
| 2022/0260578 | A1 * | 8/2022 | Gaylord | C08G 61/12 |

FOREIGN PATENT DOCUMENTS

| | | | |
|---|---|---|---|
| EP | 1281744 | A3 | 2/2003 |
| EP | 0708837 | B1 | 3/2006 |
| EP | 1279023 | B1 | 2/2007 |
| JP | 2006-510389 | | 3/2006 |
| JP | 2008-512523 | | 4/2008 |

(56) References Cited

FOREIGN PATENT DOCUMENTS

| | | | | |
|---|---|---|---|---|
| WO | WO 90/15070 | | 12/1990 | |
| WO | WO 92/10092 | A1 | 6/1992 | |
| WO | WO 93/09668 | A1 | 5/1993 | |
| WO | WO 93/10507 | A1 | 5/1993 | |
| WO | WO 93/22684 | A1 | 11/1993 | |
| WO | WO 94/09169 | A1 | 4/1994 | |
| WO | WO 97/33323 | A1 | 9/1997 | |
| WO | WO 99/26299 | A1 | 5/1999 | |
| WO | WO 00/66790 | A1 | 11/2000 | |
| WO | WO 02/081735 | A2 | 4/2003 | |
| WO | WO 02/081735 | A3 | 4/2003 | |
| WO | WO 02/079268 | A2 | 8/2003 | |
| WO | WO 02/079268 | A3 | 8/2003 | |
| WO | WO2003096016 | | 11/2003 | |
| WO | WO 2004/001379 | A2 | 12/2003 | |
| WO | WO 2004/037886 | | 5/2004 | |
| WO | WO 2004/077014 | A2 | 9/2004 | |
| WO | WO 2004/092324 | A2 | 10/2004 | |
| WO | WO 2005/086617 | A2 | 9/2005 | |
| WO | WO 2006/029231 | A1 | 3/2006 | |
| WO | WO-2006034081 | A2 * | 3/2006 | ........... G01N 33/542 |
| WO | WO2006040530 | | 4/2006 | |
| WO | WO 2006/034081 | A3 | 5/2006 | |
| WO | WO 2006/074471 | A2 | 7/2006 | |
| WO | WO 2006/074482 | A2 | 7/2006 | |
| WO | WO 2006/083932 | A2 | 8/2006 | |
| WO | WO 2006/092063 | A1 | 9/2006 | |
| WO | WO 2008/100344 | | 8/2008 | |
| WO | WO2009051560 | | 4/2009 | |
| WO | WO 2010/151807 | A1 | 12/2010 | |
| WO | WO 2011/091086 | | 7/2011 | |
| WO | WO 2016/144653 | A1 | 9/2016 | |

OTHER PUBLICATIONS

Thomas, et al. "Chemical Based on Amplifying Fluorescent Conjugated Polymers", Chem. Rev., 107:1339-1386, 2007.

Thompson, et al. Synthesis and applications of heterobifunctional poly(ethylene oxide) oligomers, Polymer, 49:345-373, 2007.

Wang, et al. "Size-Specific Interactions Between Single- and Double-Stranded Oligonucleotides and Cationic Water-Soluble Oligofluorenes", Adv. Func. Mater., 13(6):463-467, 2002.

Wang, et al. "Synthesis, characterization and selfassembly behavior in water as fluorescent sensors of cationic watersoluble conjugated polyfluorene-b-poly (N-isopropylacrylamide) diblock copolymers", Polymer, 50:1236-45, 2009.

Wang, et al. Conjugated polymer as a signal amplifier for novel silica nanoparticlebased fluoroimmunoassay, Biosens. Bioelectron., 24:3293-3298, 2009.

Xue, et al. "Synthesis of Highly Water-Soluble Fluorescent Conjugated Glycopoly(pphenylene) s for Lectin and *Escherichia coli*", Biomacromol., 7:2470-2474, 2006.

Xue, et al. Facile, Versatile Prepolymerization and PostpolymerizationFunctionalization Approaches for Well-Defined Fluorescent Conjugated Fluorene-Based Glycopolymers, Macromol., 39:5747-5752, 2006.

Xue, et al. Post-Polymerization Functionalization Approach for Highly Water-Soluble Dell-Defined Regioregular Head-to-Tail Glycopolythiophenes, Macromol., 40:6863-6870, 2007.

Xue, et al."Highly water-soluble, fluorescent, conjugated fluorene-based glycopolymers with poly(ethyleneglycol)-tethered spacers for sensitive detection of *Escherichia coli*", Chem. Eur. J., 15:2289-95, 2009.

Yeates, et al. "Ethylene glycol oligomers", Makromol. Chem., 185:1559-1563, 1984.

Yu, et al. "Synthesis of water-soluble dendritic conjugated polymers for fluorescent DNA assays", Macromol. Rapid Commun., 27:1739-45, 2006.

Zalipsky, et al. "Functionalized Poly(ethylene glycols) for Preparation of Biologically Relevant Conjugates", Bioconjugate Chem., 6:150-165, 1995.

Zheng, et al. "Biotinylated poly(p-phenylene ethynylene): unexpected energy transfer results in the detection of biological analytes", Chem. Commun. 2798-2799, 2004.

Zhou, et a;. "Methodology for Enhancing the Sensitivity of Fluorescent Chemosensors: Energy Migration in Conjugated Polymers", J. Am. Chem. Soc., 117:7017-7018.

Zhou, et a ;. "Fluorescent Chemosensors Based on Energy Migration in Conjugated Polymers: The Molecular Wire Approach to Increased Sensitivity", J. Am. Chem. Soc., 117:12593-12602, 1995.

Wosnick, et al."Synthesis and Application of Poly(phenylene Ethynylene)s for Bioconjugation: A Conjugated Polymer-Based Fluorogenic Probe for Proteases", J. Am. Chem. Soc. 2005, 127, 10, 3400-3405.

Abbel, et al. "Fluorene-based materials and their supramolecular properties", J. Polym. Sci. Part A, 47:4215-4223, 2009.

Becker, et al. "Optimisation of polyfluorenes for light emitting applications", Synthetic Metals, 125:73-80, 2002.

Bernius, et al."Progress with light-emitting polymers", Adv. Mater., 12(23):1737-1750, 2000.

Brinkley, et al. "A Brief Survey of Methods for Preparing Protein Conjugates with Dyes, Haptens, and Cross-Linking Reagents", Bioconjugate Chem., 3:2-13, 2002.

Canalle, et al. "Polypeptide-polymer bioconjugates", Chem. Soc. Rev., 39:329-353, 2010.

Disney, et a;. "Detection of Bacteria with Carbohydrate-Functionalized Fluorescent Polymers", J. Am. Chem. Soc., 126:13343-13346, 2004.

Ebewele, et al. "Polymer Science and Technology", CRC Press, 2000, 544 pages, 2000.

Eckelt, et al. "Solubility of Polymers", Encylopedia of Polymer Science & Technology, 4th Edition, 2009, Macromolecular Chemistry and Physics, 210, 1433-1439 (2009).

Ego, et al. "Attaching Perylene Dyes to Polyfluorene: Three Simple Efficient Methods for Facile Color Tuning of Light-Emitting Polymers", J. Am. Chem. Soc., 125:437-443, 2003.

Francke, et al. Synthesis of α,ω-Difunctionalized Oligo- and Poly(p-phenyleneethynylene) s, Macromol. 31:2447-2453, 1998.

Garti, et al. "Graft Copolymers as Emulsifiers: Part I: Grafted Polyethyleneglycol on Polymethylmetacrylate", J. Disperson Sci. & Tech., 14:47-70, 1993.

Gauthier, et al. "Peptide/protein-polymer conjugates:synthetic strategies and design concepts", Chem. Commun., 2591-2611, 2008.

Gordon, et al. "Synthesis of end-labeled multivalent ligands for exploring cell-surfacereceptor-ligand interactions", Chemistry & Biology, 7:9-16, 2000.

Stork, et al. "Energy Transfer in Mixtures of Water-Soluble Oligomers: Effect of Charge, Aggregation", and Surfactant Complexation, Adv. Mater., 14(5):361-366, 2002.

Grayson, et a;. "Convergent Dendrons and Dendrimers: from Synthesis to Applications", Chem. Rev., 101:3819-3867, 2001.

Hashida, et al. "More Useful Maleimide Compounds for the Conjugation of Fab' to Horseradish Perodise through Thiol Groups in the Hinge", J. Appl. Biochem., 6:56-63, 1984.

Haugland, et al. "Antibody Conjugates in Cell Biology", Current Protocols in Cell Biology, 16.5.1-16.5.22, 2000.

Haugland, et al. "Coupling of Monoclonal Antibodies with Fluorophores", Methods in Molecular Biology, 45:205-221, 1995.

Heeger, et al. "Making sense of polymer-based biosensors", PNAS, 96(22): 12219-12221, 1999.

Heredia, et al. "Synthesis of protein-polymer conjugates", Org. Biomol. Chem., 5:45-53, 2007.

Hermanson, et al. "Bioconjugate Techniques, Second Edition", 2008, 1233 pages, Elsevier Inc.

Hoffman, et a;. "Conjugates of stimuli-responsive polymers and proteins", Prog. Polym. Sci., 32:922-932, 2007.

Hou, et al. "Novel red-emitting fluorene-based copolymers", J. Mat. Chem. 12:2887-92, 2002.

Inbasekaran, et al. "Fluorene homopolymers and copolymers", Synthetic Metals 111-112:397-401, 2000.

Jones, et al. "Compendium of Polymer Terminology and Nomenclature", IUPAC Recommendations 2009.

(56) References Cited

OTHER PUBLICATIONS

Jenkins, et al."Glossary of Basic Terms in Polymer Science (IUPAC Recommendations 1996)", Pure & Appl. Chem., 68(12):2287-231, 1996.
Johnson, et al. "Fluorophores for optical imaging", Optical Imaging of Cancer 59-77, 2009.
Khan, et al. "Practical synthesis of an amphiphilic, non-ionic poly(paraphenyleneethynylene) derivative with a remarkable quantum yield in water", Chem. Commun.2005, 584-586, 2005.
Kikuchi, et al. "Recent advances in the design of smallmolecule-based FRET sensors for cell biology", Trends in Analytical Chemistry, 23:407-415, 2004.
Kim, et al. "Nonspecific Interactions of a Carboxylate-Substituted PPE with Proteins. A Cautionary Tale for Biosensor Applications", Langmuir, 21:7985-7989, 2005.
Kristensen, et al. "Behold Cytometrists: One Block Is Not Enough!", Cytometry, 99:265-268, 2020.
Kuroda, et al. "Synthesis of a nonionic water soluble semiconductive polymer", Chem.Commun., 2002, 2003:26-27.
Li, et al. "Generic strategy of preparing fluorescent conjugated-polymer-loaded poly(DL-lactide-co-glycolide) nanoparticles for targeted cell imaging", Adv. Funct. Mater., 19:3535-42, 2009.
Liu, et al. "Synthesis of a novel cationic watersoluble efficient blue photoluminescent conjugated polymer", Chem. Commun., 551-552, 2000.
Li, et al. "Water-soluble conjugated polymers as the platform for protein sensors", Polym. Chem., 1:252-259, 2010.
Shi, et al. "Synthesis and characterization of water-soluble conjugated glycopolymer for fluorescent sensing of concanavalin A", Chem. Asian J., 5:301-08, 2010.
Lou, et al. "Polymer-Based Elemental Tags for Sensitive Bioassays," Angew. Chem. Int. Ed., 46:6111-6114, 2007.
Lutz, et al. "Polymer Modifiers and Additives", 2000, CRC Press, 533 pages.
Maecker, et al. "Selecting fluorochrome conjugates for maximum sensitivity, Cytometry", 62A:169-173, 2004.
Meister, et al. "A review of polymer dissolution", Prog. Polym. Sci., 28:1223-1270, 2000.
Miller-Chou, et al. "review of polymer dissolution" , Prog.Polym. Sci., 28:1223-1270, 2003.
Minato, et al. "Polymerization of naphthalene and reactions of polynaphthalene", Chem. Soc'y of Japan, 42:779-81, 1969.
Morales, et al. "Amine-Reactive Fluorene Probes:Synthesis, Optical Characterization, Bioconjugation, and Two-Photon Fluorescence Imaging", Bioconjugate Chem., 19:2559-2567, 2008.
Odian, et al. "Principles of Polymerization", Fourth Edition, A John Wiley & Sons, Inc. 2004, 839 pages.
Panchuk-Voloshina, et al. "Alexa Dyes, a Series of New Fluorescent Dyes that Yield Exception Bright", Photostable Conjugates, J. Histochem. Cytochem., 47:1179-1188, 1996.
Phillips, et al. "Sugar-Substituted Poly(pphenyleneethynylene)s: Sensitivity Enhancement toward Lectins and Bacteria", Macromol., 41:7316-7320, 2008.
Prechtl, et al. "Precision and Purity of Conjugated Polymers—To be Ensured Before Processing", Solution-Processable Components for Organic Electronic Devices, pp. 1-55, 2019.
Sakamoto, et al. "Suzuki Polycondensation: Polyarylenes à la Carte", Macromol. Rapid Commun., 30:653-687, 2003.
Shapiro, et al. "Practical Flow Cytometry", Fourth Edition, John Wiley & Sons Inc, 2003.
Stockton, et al. "Hydrolysis of 3-carboxy-6,8-difluoro-7-hydroxycoumarin (Pacific BlueTM) succinimidyl ester under acidic and basic conditions", Dyes & Pigments, 97:148-151, 2012.
Barendt et al., "Supramolecular Assemblies for Electronic Materials", Chem. Eur. J., vol. 26, No. 17, pp. 3744-3748 (2020).
McQuade, et al., "Conjugated Polymer-Based Chemical Sensors", Chem. Rev., vol. 100, pp. 2537-2574 (2000).
Nobel Prize 2000 The Nobel Prize in Chemistry 2000, https://www.nobelprize.org/prizes/chemistry/2000/summary/ (last accessed Aug. 17, 2022).
An et al., "A fluorescence ratiometric protein asssay using light-harvesting conjugated polymers," Macromolecular Rapid Communications 27(13):993-997 (2006).
Ausebel et al., eds., Current Protocols in Molecular Biology, vols. I, II, and III. 1997.
Ausubel et al., eds., Short Protocols in Molecular Biology: A Compendium of Methods from Current Protocols in Molecular Biology, 5.sup.th ed., John Wiley & Sons, Inc., 2002, 1512 pages.
Bailey et al., "Masked Micheal Acceptors in Poly(phenyleneethynylene)s for Facile Conjugation," Macromolecules 39:2815-2818 (2006).
Bruchez et al., "Semiconductor nanocrystals as fluorescent biological labels," Science 281:2013-2016 (1998).
Chen et al., "Highly sensitive biological and chemical sensors based on reversible fluorescence quenching in a conjugated polymer," PNAS USA 96(220:12287-12292 (1999).
Delagrave et al., "Isolated mutants of cloned Aequorea victoria GFP that had red-shifted excitation spectra," Bio/Tech 13:151-154 (1995).
Fodor et al., "Light-directed, spatially addressable parallel chemical synthesis," Science 251(4995):767-773 (1991).
Gaylord et al., "DNA detection using water-soluble conjugated polymers and peptide nucleic acid probes," PNAS USA 99(17):10954-10957 (2002).
Gaylord et al., "DNA hybridization detection with water-soluble conjugated polymers and chromophore-labeled single-stranded DNA," J Am Chem Soc 124(4):896-900 (2003).
Gaylord et al., "SNP detection using peptide nucleic acid probes and conjugated polymers: application in neurodegenerative disease identification," PNAS USA 102(1):34-39 (2005).
Geierstanger and Wemmer, "Complexes of the minor groove of DNA," Annu Rev Biophys Biomol Struct 24:463-493 (1995).
Glumoff and Goldman, Nucleic Acids in Chemistry and Biology, 2.sup.nd ed., Blackburn and Gait, eds., Oxford University Press, Oxford, 1996, pp. 375-441.
Heeger et al., "Making sense of polymer-based biosensors," PNAS USA 96(22):12219-12221 (1999).
Heim et al., "Improved green fluorescence," Nature 373:663-664 (1995).
Heim et al., "Wavelength mutations and post-translational autoxidation of green fluorescent protein," PNAS USA 91:12501-12504 (1994).
Ho et al., "Colorimetric and fluorometric detection of nucleic acids using cationic polythiophene derivatives," Angewandte Chemie International Edition 41(9):1548-1551 (2002).
Ho et al., "Direct molecular detection of nucleic acids by fluorescence signal amplification," J Am Chem Soc 127(36):12673-12676 (2005).
Innis et al., eds., PCR Protocols: A Guide to Methods and Applications, Elsevier Science & Technology Books 1990, 482 pages.
Invitrogen—available at www.invitrogen.com, accessed Dec. 19, 2007.
Invitrogen—Molecular Probes, available at www.probes.com, accessed Dec. 19, 2007.
Kanehisa, "Use of statistical criteria for screening potential homologies in nucleic acid sequences," Nucleic Acids Research 12(1 Pt 1):203-213 (1984).
Kreuzer et al., "LightCycler technology fo rthe quantitation of bcr/abl fusion transcripts," Cancer Research 59(13):3171-3174 (1999).
Kreyenschmidt et al., "A New Soluble poly(p-phenylene) with Tetrahydropryrene Repeating Units," Macromolecules 28:4577-4582 (1995).
Larson and Verdine, Bioorganic Chemistry: Nucleic Acids, Hecht ed., Oxford University Press: New York 1996 pp. 324-346.
Laurendeau et al., "Quantitation of MYC gene expression in sporadic breast tumors with a real-time reverse transcription PCR assay," Cancer Res 59(12):2759-2765 (1999).
Laurendeau et al., "TaqMan PCR-based gene dosage assay for predictive testing in individuals from a cancer family with INK4 locus haploinsufficiency," Clin Chem 45(7):982-986 (1999).
Leclerc, "Polyfluorenes: Twenty Years of Progress," Polym Sci Part A: Polym Chem 39:2867-2873 (2001).
Lee et al., "Synthesis and Characterization of Oligo(9,9-dihyexyl-2,7-fluorene ethynylene)s: for Application as Blue Light-Emitting Diode," Org Lett 3:2005-2007 (2001).

(56) References Cited

OTHER PUBLICATIONS

Lee, Kangwon. "Functionalized Conjugated Polymers for Signal Amplifying Biosensors and Sensor Arrays." Dissertation, The University of Michigan, 2008, 266 pages.
Leonard et al. "Epratuzumab, a humanized anti-CD22 antibody, in aggressive non-hodgkin's lymphoma: phase I/II clinical trial results," Clinical Cancer Research 2004, vol. 10, pp. 5327-5334.
Liu et al., "Interpolyelectrolyte complexes of conjugated copolymers and DNA: platforms for multicolor biosensors," J Am Chem Soc 126(7):1942-1943 (2004).
Liu et al., "Methods for strand-specific DNA detection with cationic conjugated polymers suitable for incorporation into DNA chips and microarrays," PNAS USA 102(3):589-593 (2005).
Liu et al., "Optimization of the molecular orbital energies of conjugated polymers for optical amplification of fluorescent sensors," J Am Chem Soc 128:1188-1196 (2006).
Liu et al., "Shape-adaptable water-soluble conjugated polymers," J Am Chem Soc 124(44):13306-13307 (2003).
Liu et al., Characterization of tectoRNA assembly with cationic conjugated polymers, J Am Chem Soc 126(13):4076-4077 (2004).
Mikroyannidis et al., "Alternating copolyfluorenevinyles with polynuclear aromatic moieties: Synthesis, photophysics, and electroluminescence," J Polym Sci Part A:Polym Chem 45:4661-4670 (2007).
Mikroyannidis et al.; New highly luminescent—neutral precursors; John Wiley & Sons, Inc.; 2007, Chem Abstract 147:10286.
Mikroyannidis et al.; Novel electroluminescent—and its precursor; John Wiley & Sons, Inc.; 2007; Chem abstract 146:462600.
Pei et al., "Efficient Photoluminescence and Electroluminescence from a Soluble Polyfluorene," J Am Chem Soc 118:7416-7417 (1996).
Pierce, Biotechnology, available at www.piercenet.com, accessed Dec. 19, 2007.
Sambrook et al., Molecular Cloning: A Laboratory Manual, 3.sup.rd ed., Cold Spring Harbor Laboratory Press, 2000.
Sekar et al., "Phycobiliproteins as a commodity: trends in applied research, patents and commercialization," J Appl Phycol 20:113-136 (2008).
Sonogashira et al., "A convenient synthesis of acetylenes: catalytic substitutions of acetylenic hydrogen with bromoalkenes, iodoarenes and bromopyridines," Tetra Lett 16:4467-4470 (1975).
Wang et al., "Biosensors from conjugated polyelectrolyte complexes," PNAS USA 99(1):49-53 (2002).
Wang et al., "Collective optical behavior of cationic water-soluble dendrimers," Advanced Materials 16(23-24):2127-2132 (2004).
Wang et al., "Fluorescein provides a resonance gate for FRET from conjugated polymers to DNA intercalated dyes," J Am Chem Soc 126(17):5446-5451 (2004).
Wang et al., "Optimally amplified RNA-protein detection methods using light-harvesting conjugated polymers," Advanced Materials 15(17):1425-1428 (2003).
Wang, "From DNA biosensors to gene chips," Nucl Acids Res 28(16):3011-3016 (2000).
Wosnick et al., "Synthesis and application of poly(phenylen ethynylene)s for bioconjugation: a conjugated polymer-based fluorogenic proble for proteases," J Am Chm Soc 127:3400-3405 (2005).
Xu et al., "Magnetically assisted DNA assays: high selectivity using conjugated polymers for amplified fluorescent transduction," Nucl Acids Res 33(9):e83 (2005).
Yamamoto et al., "Preparation of .pi.-Conjugated Poly(thiophene-2,5-diyl), Poly(p-phenylene), and Related Polymers Using Zerovalent Nickel Complexes. Linear Structure and Properties of the .pi.-Conjugated Polymers," Macromolecules 25:1214-1223 (1992).
Zhou et al., "Polyfluorenes with phosphonate groups in the side chains as chemosensors and electroluminescent materials," Macromolecules 38:5416-5424 (2005).
U.S. Appl. No. 07/624,120 (AB), filed Dec. 6, 1990, Fodor.
U.S. Appl. No. 60/642,901, filed Jan. 10, 2005, Bazan.
PCT/US07/80734 Search Report dated Oct. 28, 2008.
PCT/US11/21775 Search Report and Written Opinion dated May 19, 2011.
PCT/US2010/40051 International Search Report dated Sep. 30, 2010.
EP 07873316 Supplemental Search Report dated Aug. 3, 2010.
JP2009-531642 Office Action dated Mar. 22, 2012.
Pradhan, Swapna "Ionic, Water-Soluble Polyfluorene-Type Copolymers," Doctoral Dissertation, Bergische Universitat Wuppertal, Elektronische Publikationen Universitatsbibliothek Wuppertal, URN (NBN) urn:nbn:de:hbz:468-20040539, October.
Tapia et al. "Interaction between the Water Soluble Poly{1,4-phenylene-[9,9-bis(4-phenoxybutylsulfonate)]fluorene-2,7-diyl} Copolymer and Ionic Surfactants Followed by Spectroscopic and Conductivity Measurements," J. Phys. Chem. B 2005, vol. 109.
Wang et al. "Size-specific interactions between single- and double-stranded oligonucleotides and cationic water soluble oligofluorenes," Adv. Funct. Mater 2003, vol. 6, No. 13, pp. 463-467.
Wang et al. "Solvent-dependent aggregation of water-soluble poly(fluorene) controls energy transfer to chromophore labeled DNA," Chem. Commun. 2004, pp. 2508-2509.
Schafer-Hales, et al. "Fluorene-based fluorescent probes with high two-photon action cross-sections for biological multiphoton imaging applications", J Biomed Opt., Sep-Oct. 2005;10(5):051402.
USPTO Petitioner's Reply Inter Partes Review IPR2022-01207 U.S. Pat. No. 10,288,620, Jul. 14, 2023, 32 pages.
USPTO Petitioner's Reply Inter Partes Review IPR2022-01206 U.S. Pat. No. 10,302,648, Jul. 14, 2023, 32 pages.
USPTO Petitioner's Reply Inter Partes Review IPR2022-01205 U.S. Pat. No. 10,955,417, Jul. 14, 2023, 19 pages.
USPTO Petitioner's Reply Inter Partes Review IPR2022-01204 U.S. Pat. No. 10,365,285, Jul. 14, 2023, 32 pages.
USPTO Petitioner's Reply Inter Partes Review IPR2022-01203 U.S. Pat. No. 10,458,989, Jul. 14, 2023, 32 pages.
Wang, et al. "A Water-Soluble Π-Conjugated Polymer with up to 100 mg mL-1 Solubility", Macro Molecular Rapid Communications, vol. 28, Issue16, Aug. 14, 2007, pp. 1645-1650.
USPTO Judgment—Final Written Decision Determining All Claims Unpatentable Granting Motions to Seal 35 U.S.C. § 318(a), Inter Partes Review IPR2022-01203 U.S. Pat. No. 10,458,989, Dec. 21, 2023, 79 pages.
USPTO Judgment—Final Written Decision Determining All Claims Unpatentable Granting Motions to Seal 35 U.S.C. § 318(a), Inter Partes Review IPR2022-01204 U.S. Pat. No. 10,365,285, Dec. 21, 2023, 82 pages.
USPTO Judgment—Final Written Decision Determining All Claims Unpatentable Granting Motions to Seal 35 U.S.C. § 318(a), Inter Partes Review IPR2022-01205 U.S. Pat. No. 10,955,417, Dec. 21, 2023, 68 pages.
USPTO Judgment—Final Written Decision Determining All Claims Unpatentable Granting Motions to Seal 35 U.S.C. § 318(a), Inter Partes Review IPR2022-01206 U.S. Pat. No. 10,302,648, Dec. 21, 2023, 77 pages.
USPTO Judgment—Final Written Decision Determining All Claims Unpatentable Granting Motions to Seal 35 U.S.C. § 318(a), Inter Partes Review IPR2022-01206 U.S. Pat. No. 10,288,620, Dec. 21, 2023, 87 pages.

* cited by examiner $R_1$ = solubilizing group, such as $(CH_2)_n\overset{\oplus}{N}Me_3\overset{\ominus}{Br}$
$R_2$ = H, F, alkoxy, or solubilizing group $R^1$ = solubilizing group, such as $(CH_2)_n\overset{\oplus}{N}Me_3\overset{\ominus}{Br}$ $R^1$ = solubilizing group, such as $(CH_2)_n\overset{\oplus}{N}Me_3\overset{\ominus}{Br}$ $R_2 = (CH_2)_6NMe_3Br$
Negative control polymer $R_2 = (CH_2)_6NMe_3Br$
Biotinyl-polymer FIG. 30A
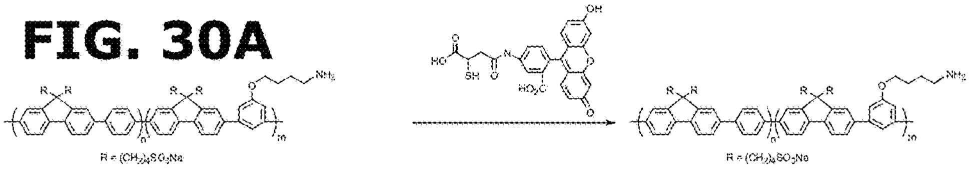
Negative control polymer
FIG. 30B
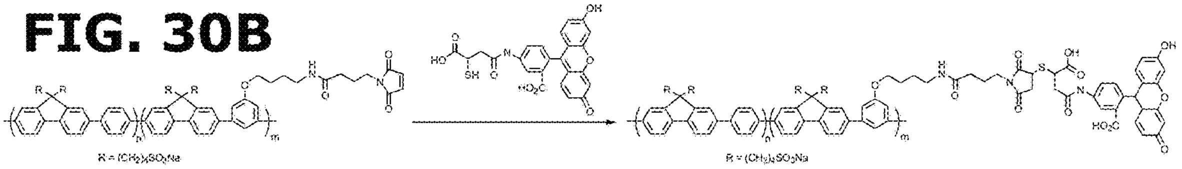
Maleimide-functionalized polymer
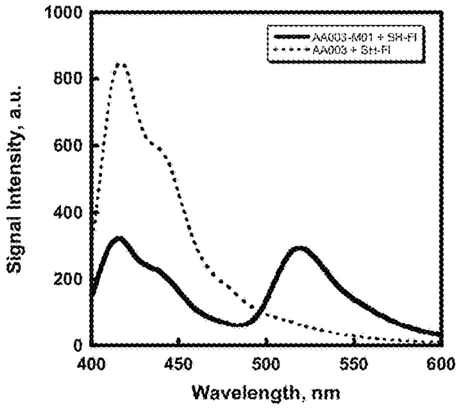
FIG. 30C Negative control polymer Biotinyl polymer R = $(CH_2)_6NMe_3Br$

FLUORESCENT METHODS AND MATERIALS FOR DIRECTED BIOMARKER SIGNAL AMPLIFICATION

CROSS-REFERENCE

This application claims the benefit of U.S. Provisional Application No. 60/828,615, filed Oct. 6, 2006, which application is incorporated herein by reference.

BACKGROUND OF THE INVENTION

Fluorescent hybridization probes have developed into an important tool in the sequence-specific detection of DNA and RNA. The signals generated by the appended fluorescent labels (or dyes) can be monitored in real time, and provide simple, rapid, and robust methods for the detection of biological targets and events. Utility has been seen in applications ranging from micro arrays and real time PCR to fluorescence in situ hybridization (FISH).

Recent work in the area of multichromophores, particularly regarding conjugated polymers (CPs) has highlighted the potential these materials have in significantly improving the detection sensitivity of such methods (Liu and Bazan, Chem. Mater., 2004). The light harvesting structures of these materials can be made water soluble and adapted to amplify the fluorescent output of various probe labels (See U.S. patent application Ser. No. 10/600,286, filed Jun. 20, 2003 and Gaylord, Heeger, and Bazan, Proc. Natl., Acad. Sci., 2002, both of which are incorporated herein by reference in their entirety).

In particular, cationic CPs have shown strong affinity for oppositely charged nucleic acids, ensuring the distances required to transfer energy from a photo-excited polymer (a light harvesting donor) to a fluorescently labeled probe/target pair. The light output can be increased by 75-fold relative to the directly excited dye alone (Liu and Bazan, J. Am. Chem. Soc., 2005). The signal amplification adds a variety of benefits in both homogeneous and heterogeneous detection formats.

Results such as these indicate CPs to be highly promising in the field of nucleic acid diagnostics, particularly where sample quantities are scarce. However, there exist methods for the amplification (or replication) of nucleic acid targets, i.e., PCR. Comparatively, in the field of protein recognition, there are no such simple methods for amplifying the targeted materials. As such, signal enhancement arising from CP application is of high consequence in this area.

Dye-labeled antibodies are regularly used for the detection of protein targets in applications such as immunohistochemistry, protein arrays, ELISA tests, and flow cytometry. Integrating CP materials into such methodologies promise to provide a dramatic boost in the performance of such assays, enabling detection levels previously unattainable with conventional dyes.

SUMMARY OF THE INVENTION

In general, in one aspect, an assay method includes providing a sample that is suspected of containing a target biomolecule, providing a sensor conjugated to a signaling chromophore and capable of interacting with the target biomolecule, providing a conjugated polymer including but not limited to

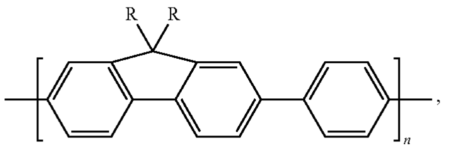

$R = (CH_2)_6\overset{\oplus}{N}Me_3\overset{\ominus}{Br}$

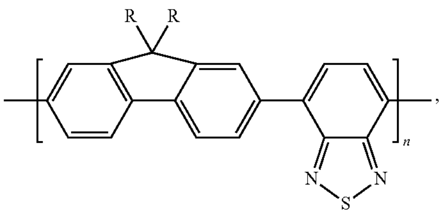

$R = (CH_2)_6\overset{\oplus}{N}Me_3\overset{\ominus}{Br}$

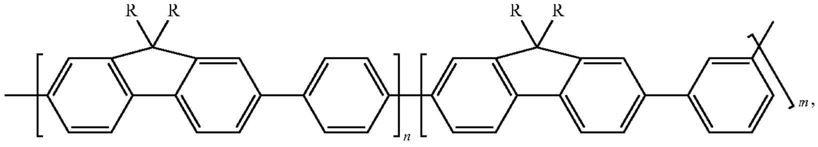

$R = (CH_2)_6\overset{\oplus}{N}Me_3\overset{\ominus}{Br}$ and

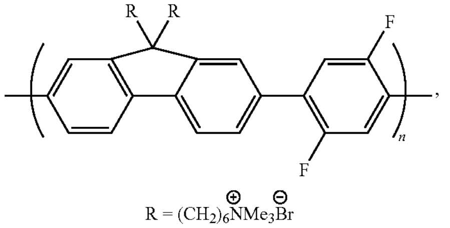

$R = (CH_2)_6\overset{\oplus}{N}Me_3\overset{\ominus}{Br}$ wherein the polymer electrostatically interacts with the sensor and upon excitation is capable of transferring energy to the sensor signaling chromophore, contacting the sample with the sensor and the multichromophore in a solution under conditions in which the sensor can bind to the target biomolecule if present, applying a light source to the sample that can excite the multichromophore, and detecting whether light is emitted from the signaling chromophore.

In one embodiment the R group is sulfonate. In another embodiment the sensor is a biomolecule, for example protein, nucleic acid or an antibody.

In another embodiment the sensor can include a plurality of sensors conjugated to a plurality of signaling chromophores, wherein at least two of the plurality of chromophores cilia different wavelengths of light upon energy transfer from the multichromophore.

In general, in another aspect a multichromophore complex including a multichromophore coupled to at least one biomolecule is provided. The biomolecule can include but is not limited to a sensor biomolecule, a bioconjugate and a target biomolecule. The multichromophore of the complex is further coupled to a signaling chromophore and includes the following structure:

$$-(((-[CP_1]_a-[CP_2]_b)_m[CP_1]_a-[CP_3]_c)_n[CP_1]_a-[CP_4]_d)_p-$$

wherein CP1, CP2, CP3, and CP4 are optionally substituted conjugated polymer segments or oligomeric structures, that are the same or different from one another. In one embodiment the conjugated polymer is a cationic conjugated polymer. In another embodiment the conjugated polymer is an anionic conjugated polymer. In a further embodiment the conjugated polymer is a charge-neutral conjugated polymer. In one embodiment $CP_1$, $CP_2$, $CP_3$, and $CP_4$ are aromatic repeat units, selected from the group consisting of benzene, naphthalene, anthracene, fluorene, thiophene, furan, pyridine, and oxadiazole, each optionally substituted, and wherein $CP_3$ and $CP_4$ can contain one or more unique bioconjugation sites, linked by a linker.

In an alternative embodiment multichromophore includes bioconjugation sites including but not limited to maleimide, thiol, succimidylester (NHS ester), amine, azide chemistry, carboxy/EDC (1-Ethyl-3-[3-dimethylaminopropyl]carbodiimide Hydrochloride, Sulfo-SMCC (Sulfosuccinimidyl 4-[N-maleimidornethyl]cyclohexane-1-carboxylate), amine/BMPH (N-[β-Maleimidopropionic acid]hydrazide·TFA), and Sulfo-SBED Sulfosuccinimidyl[2-6-(biotinamido)-2-(p-azidobenzamido)-hexanoamido]-ethyl-1,3'-dithiopropionate.

The multichromophore of the complex has the structure:

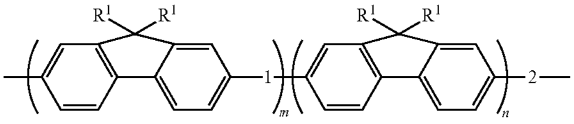

wherein $R^1$ is a solubilizing group including but not limited to ethylene glycol oligomers, ethyleneglycol polymers, ω-ammonium alkoxy sails, and ω-sulfonate, alkoxy salts.

Alternatively, in another embodiment, the multichromophore of the complex has the structure:

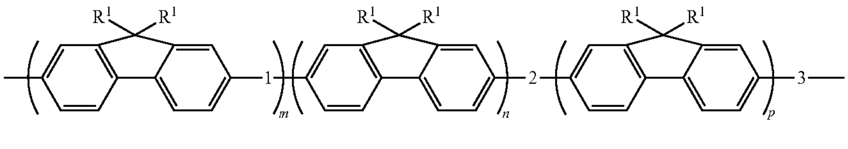

wherein $R^1$ is a solubilizing group selected from the group consisting of ethylene glycol oligomers, ethylene glycol polymers, ω-ammonium alkoxy salts, and ω-sulfonate alkoxy salts. In particular embodiments the 1, and 2 can include a-g linking groups having the structure:

a

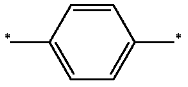

b

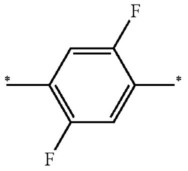

c

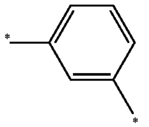

d

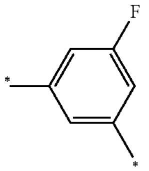

e

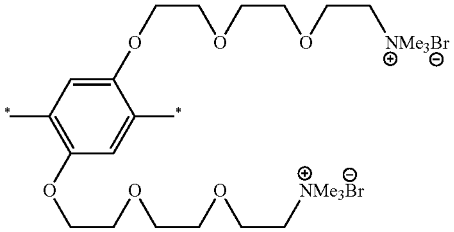

f

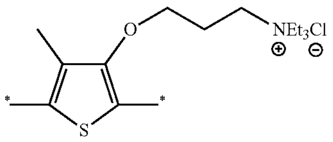

g

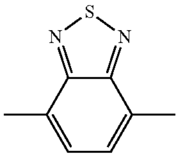

* = site for covalent attachment to unsaturated backbone

Additionally, 3 can be group h having the structure:

h

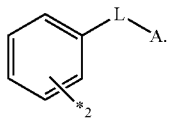

L = linker
A = bioconjugation site
* = site for covalent attachment to unsaturated backbone In another embodiment multichromophore of the complex can have the structure:

wherein $R^1$ is a solubilizing group, including ethylene glycol oligomers, ethylene glycol polymers, ω-ammonium alkoxy sails, and ω-sulfonate alkoxy salts.

In general, in another aspect a multichromophore complex for identifying a target biomolecule is provided that includes a multichromophore, a sensor biomolecule covalently linked to the multichromophore, a signaling chromophore covalently linked to the multichromophore, wherein the signaling chromophore is capable of receiving energy from the multichromophore upon excitation of the multichromophore and the sensor biomolecule is capable of interacting with the target biomolecule. In one embodiment

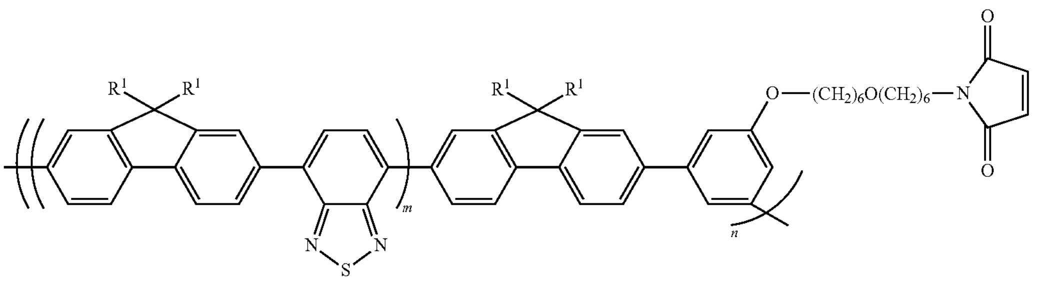

wherein $R^1$ is a solubilizing group including but not limited to ethylene glycol oligomers, ethylene glycol polymers, ω-ammonium alkoxy salts, and ω-sulfonate alkoxy salts.

In still another embodiment multichromophore of the complex can have the structure:

both the signaling chromophore and the sensor biomolecule are covalently linked to the multichromophore through a plurality of linkers. In an alternative embodiment both the signaling chromophore and the sensor biomolecule are covalently linked to the multichromophore through a tri-func-

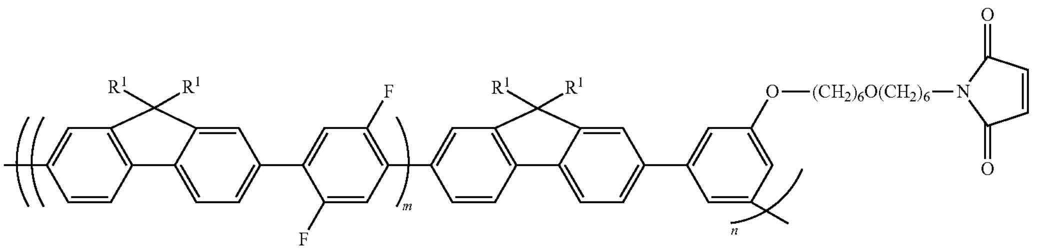

wherein $R^1$ is a solubilizing group selected from the group consisting of ethylene glycol oligomers, ethylene glycol polymers, ω-ammonium alkoxy salts, and ω-sulfonate alkoxy salts.

In yet another embodiment multichromophore of the complex can have the structure:

tionalized linker that covalently binds the multichromophore, the signaling chromophore and the sensor biomolecule.

In one embodiment the linker has a linking chemistry including but not limited to maleimidelthiol, succimidylester (NHS ester)/amine, azide chemistry, carboxy/EDC (1-Ethyl-

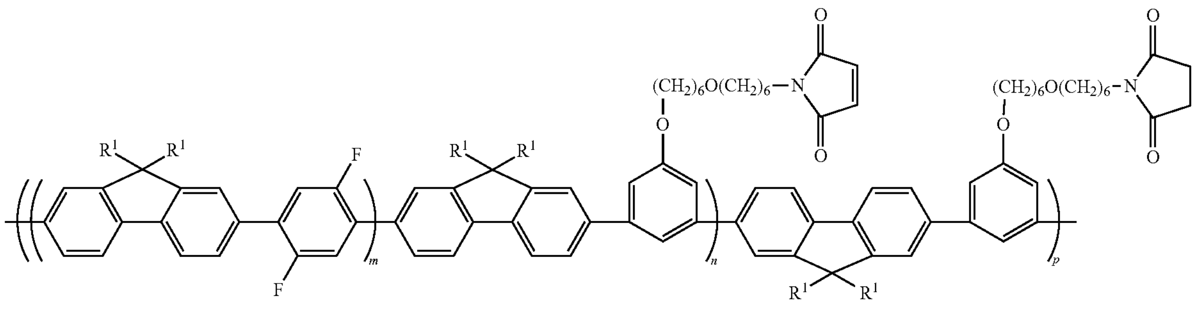

3-[3-dimethylaminopropyl]carbothimide Hydrochloride)/amine, amine/Sulfo-SMCC (Sulfosuccinimidyl 4-[N-maleimidomethyl]cyclohexane-1-carboxylate)/thiol, and amine/BMPH (N-[β-Maleimidopropionic acid]hydrazide·TFA)/thiol. In a particular embodiment the multichromophore is a conjugated polymer, for example a polycationic conjugated polymer.

In general, in another aspect an assay method provided includes the steps of providing a sample that is suspected of containing a target biomolecule, providing a multichromophore complex comprising a multichromophore, a covalently linked signaling chromophore and a covalently linked sensor biomolecule, wherein the signaling chromophore is capable of receiving energy from the multichromophore upon excitation of the multichromophore and the sensor biomolecule is capable of interacting with the target biomolecule, contacting the sample with the multichromophore complex in a solution under conditions in which the sensor biomolecule can bind to the target biomolecule if present, applying a light source to the sample that can excite the multichromophore, and detecting whether light is emitted from the signaling chromophore. In a particular embodiment the multichromophore is a conjugated polymer, for example a polycationic conjugated polymer.

In general, in another aspect an assay method is provided including the steps of providing a sample that is suspected of containing a target biomolecule, providing a first bioconjugate conjugated to a signaling chromophore and capable of interacting with the target biomolecule, providing a second bioconjugate conjugated to a multichromophore, wherein the chromophore includes the structure $$-\left[\left[\left[[CP_1]_a-[CP_2]_b\right]_m[CP_1]_a-[CP_3]_c\right]_n[CP_1]_a-[CP_4]_d\right]_p-$$

wherein CP1, CP2, CP3, and CP4 are optionally substituted conjugated polymer segments or oligomer structures, that are the same or different from one another, wherein the second bioconjugate can bind to the first bioconjugate and wherein upon such binding excitation of the multichromophore is capable of transferring energy to the signaling chromophore, contacting the sample with the first bioconjugate in a solution under conditions in which the first bioconjugate can bind to the target biomolecule if present, contacting the solution with the second bioconjugate, applying a light source to the sample that can excite the multichromophore, and detecting; whether light is emitted from the signaling chromophore. In one embodiment $CP_1$, $CP_2$, $CP_3$, and $CP_4$ are aromatic repeat units, including; but not limited to benzene, naphthalene, anthracene, fluorene, thiophene, furan, pyridine, and oxadiazole, each optionally substituted, and wherein $CP_3$ and $CP_4$ can contain one or more unique bioconjugation sites, linked by a linker. In a particular embodiment the multichromophore is a conjugated polymer, for example a polycationic conjugated polymer, an anionic conjugated polymer and/or a charge-neutral conjugated polymer.

In a related embodiment the multichromophore has bioconjugation sites including but not limited to maleimide, thiol, succimidylester (NHS ester), amine, azide chemistry, carboxy/EDC (1-Ethyl-3-[3-dimethylaminopropyl]carbodiimide Hydrochloride. Sulfo-SMCC (Sulfosuccinimidyl 4-[N-maleimidomethyl]cyclohexane-1-carboxylate), amine/BMPH (N-[β-Maleimidopropionic acid]hydrazide·TFA), and Sulfo-SBED Sulfosuccinimidyl[2-6-(biotinamido)-2-(p-azidobenzamido)-hexanoamidol]-ethyl-1,3'-dithiopropionate.

In a particular embodiment the multichromophore has the structure:

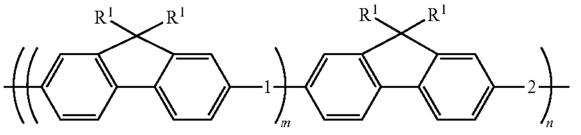

wherein $R^1$ is a solubilizing group selected from the group consisting of ethylene glycol oligomers, ethylene glycol polymers, ω-ammonium alkoxy salts, and ω-sulfonate alkoxy salts.

In yet another embodiment the multichromophore has the structure:

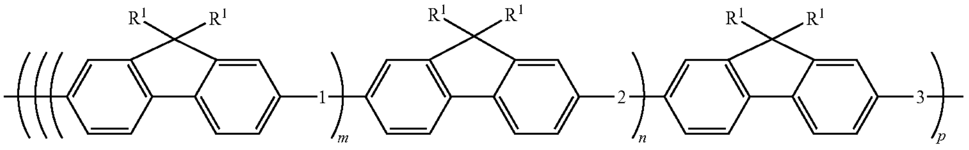

wherein $R^1$ is a solubilizing group selected from the group consisting of ethylene glycol oligomers, ethylene glycol polymers, ω-ammonium alkoxy salts, and ω-sulfonate alkoxy salts.

In a further embodiment 1, and 2 can include one or more a-g linking groups having the structure:

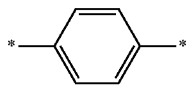

a

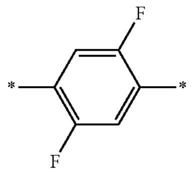

b

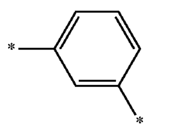

c d

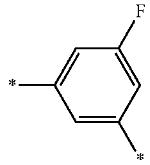

e

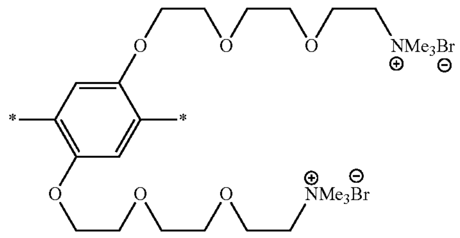

f

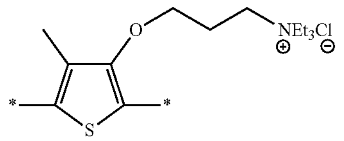

g

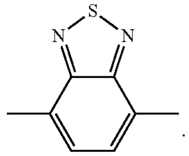

* = site for covalent attachment to unsaturated backbone

In one embodiment 3 is group h and has the structure:

h

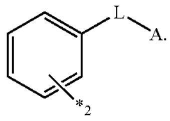

L = linker
A = bioconjugation site
* = site for covalent attachment to unsaturated backbone In another embodiment multichromophore, of the complex can have the structure:

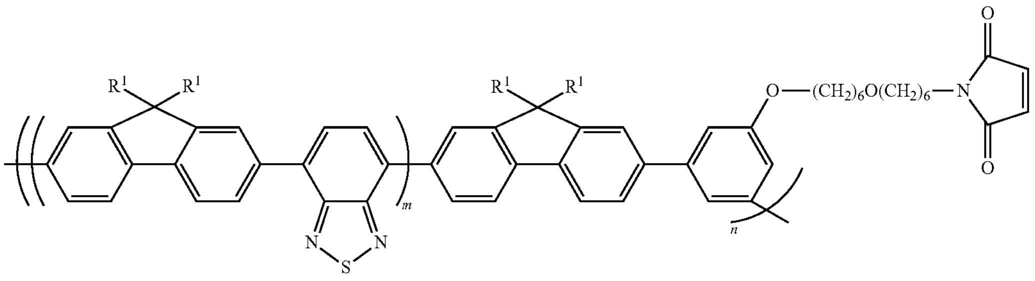

wherein $R^1$ is a solubilizing group including but not limited to ethylene glycol oligomers, ethylene glycol polymers, ω-ammonium alkoxy salts, and ω-sulfonate alkoxy salts.

In yet another embodiment multichromophore of the complex can have the structure:

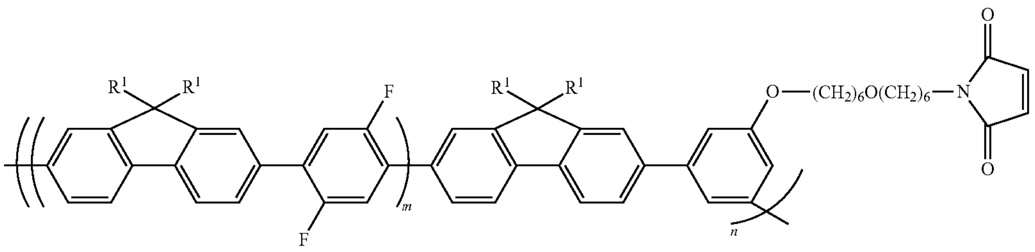

wherein $R^1$ is a solubilizing group including but not limited to ethylene glycol oligomers, ethylene glycol polymers, ω-ammonium alkoxy salts, and ω-sulfonate alkoxy salts.

In another embodiment multichromophore of the complex can have the structure:

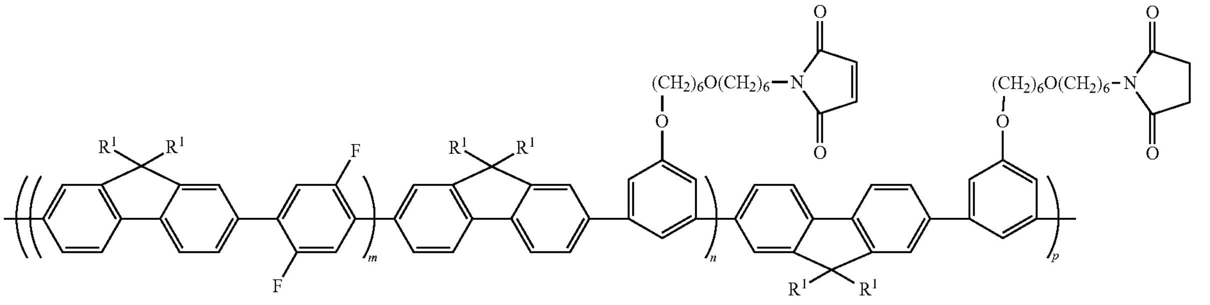

wherein $R^1$ is a solubilizing group, including but not limited to ethylene glycol oligomers, ethylene glycol polymers, ω-ammonium alkoxy salts, and ω-sulfonate alkoxy salts. In a particular embodiment the multichromophore is a conjugated polymer, for example a polycationic conjugated polymer, an anionic conjugated polymer and/or a charge-neutral conjugated polymer.

In one embodiment at least one of the first and second bioconjugate is an antibody. In a particular embodiment the first and second bioconjugates are antibodies.

In general, in another aspect an assay method provided includes the steps of providing a sample that is suspected of containing a target biomolecule, providing a multichromophore, comprising a covalently linked first bioconjugate, providing a sensor biomolecule, complex comprising a sensor biomolecule capable of interacting with the target molecule, a signaling chromophore, and a covalently linked second bioconjugate capable of binding with the first bioconjugate, wherein upon such binding excitation of the multichromophore is capable of transferring energy to the signaling chromophore, contacting the sample with the sensor biomolecule complex in a solution under conditions in which the sensor biomolecule can bind to the target biomolecule if present, contacting; the solution with the multichromophore, applying a light source to the sample that can excite the multichromophore, and detecting whether light is emitted from the signaling chromophore. In a particular embodiment the multichromophore is a conjugated polymer, for example a polycationic conjugated polymer, an anionic conjugated polymer and/or a charge-neutral conjugated polymer.

In one embodiment the first and second bioconjugates include but are not limited to a protein, an antibody and a nucleic acid. In a related embodiment the first bioconjugate is streptavidin or biotin, the sensor biomolecule is an antibody, and the second bioconjugate is biotin where the first bioconjugate is streptavidin or biotin where the first bioconjugate is streptavidin. In another embodiment the first bioconjugate is streptavidin or biotin, the sensor biomolecule is a nucleic acid, and the second bioconjugate is biotin where the first bioconjugate is streptavidin or biotin where the first bioconjugate is streptavidin.

In general, in another aspect a biorecognition complex for identifying a biomolecule is provided. The complex can include a bioconjugate, a signaling chromophore covalently linked to the bioconjugate, a multichromophore covalently linked to the bioconjugate, wherein excitation of the multichromophore is capable of transferring energy to the signaling chromophore.

In one embodiment the bioconjugate can include but is not limited to an antibody or streptavidin. In a particular embodiment the multichromophore is a conjugated polymer, for example a polycationic conjugated polymer, an anionic conjugated polymer and/or a charge-neutral conjugated polymer.

In general, in one aspect an assay method is provided including the steps of providing a sample that is suspected of containing a target biomolecule, providing a biorecognition complex comprising a bioconjugate, a signaling chromophore covalently linked to the bioconjugate and a multichromophore covalently linked to the bioconjugate, wherein excitation of the multichromophore is capable of transferring energy to the signaling chromophore, contacting the sample with the biorecognition complex in a solution under conditions in which the bioconjugate can bind to the target biomolecule or a target-associated biomolecule if present, applying a light source to the solution that can excite the multichromophore, and detecting whether light is emitted from the signaling chromophore. In a particular embodiment the multichromophore is a conjugated polymer, for example a polycationic conjugated polymer, an anionic conjugated polymer and/or a charge-neutral conjugated polymer.

In general in another aspect, a biorecognition complex for identifying a target biomolecule is provided that includes a bioconjugate, a multichromophore covalently linked to the bioconjugate, and a signaling chromophore covalently linked to the multichromophore, wherein excitation of the multichromophore is capable of transferring energy to the signaling chromophore. In one embodiment the bioconjugate is an antibody. In another embodiment the bioconjugate, is streptavidin. In a particular embodiment the multichromophore is a conjugated polymer, for example a poly at conjugated polymer, an anionic conjugated polymer and/or a charge-neutral conjugated polymer.

In general in another aspect an assay method is provided including the steps of providing a sample that is suspected of containing a target biomolecule, providing a biorecognition complex comprising bioconjugate complex comprising bioconjugate, a multichromophore covalently linked to the bioconjugate, and a signaling; chromophore covalently linked to the multichromophore, wherein excitation of the multichromophore is capable of transferring energy to the signaling chromophore, contacting the sample with the biorecognition complex in a solution under conditions in which the bioconjugate can bind to the target biomolecule or a target-associated biomolecule if present, applying a light source to the solution that can excite the multichromophore, and detecting whether light is emitted from the signaling chromophore. In a particular embodiment the multichromophore is a conjugated polymer, for example a polycationic conjugated polymer, an anionic conjugated polymer and/or a charge-neutral conjugated polymer.

In another aspect methods are provided as in any of a number of the methods disclosed herein wherein expression of a gene is detected upon detection of the target biomolecule.

In another aspect methods are provided as in any of a number of the methods disclosed herein wherein detection of the target biomolecule provides a result used to diagnose a disease state of a patient. In one embodiment the method of diagnosing a disease includes the steps of reviewing or analyzing data relating to the presence of a target biomolecule in a sample; and providing a conclusion to a patient, a health care provider or a health care manager, the conclusion being based on the review or analysis of data regarding a disease diagnosis. In a related embodiment providing a conclusion includes transmission of the data over a network.

In general, in another aspect kits for identifying a target biomolecule are provided. In one embodiment a kit includes a multichromophore, a sensor biomolecule covalently linked to the multichromophore, a signaling chromophore covalently linked to the multichromophore, wherein the signaling chromophore is capable of receiving energy from the multichromophore upon excitation of the multichromophore and the sensor biomolecule is capable of interacting with the target biomolecule. In a particular embodiment the kit further includes a substrate.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 30A. Schematic of a control polymer structure.

FIG. 30B. Schematic of an experimental polymer structure relating, to one embodiment of the invention, FIG. 30C. Plot of the fluorescence spectra relating to said control and an experimental polymer.

DETAILED DESCRIPTION OF THE INVENTION

Figure 1:
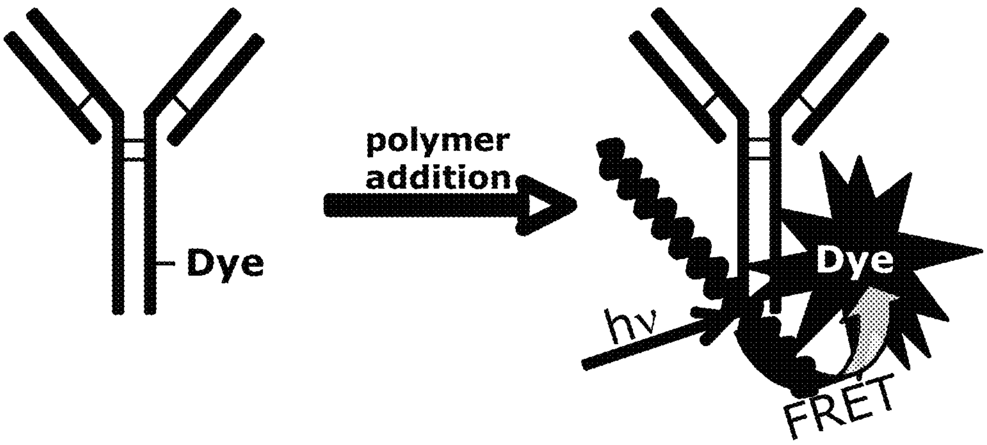
FIG. 1. Schematic of electrostatic binding of a multichromophore in one embodiment of the invention.

Although charged multichromophore structures and basic electrostatic interactions can be effective in the amplification of dye labeled antibodies, more directed methods of multichromophore association can ensure lower backgrounds and improved signaling. The multichromophore materials can be directly conjugated (covalently linked) to antibodies and/or dyes providing added control (multichromophore-dye distances) in the assay. Essentially, the signaling dye is closely coupled with the amplifying polymer. Furthermore, the conjugation of multichromophores is not limited to dyes or antibodies; rather, the multichromophores can be conjugated to any variety of biomolecules, including proteins (such as avidin/streptavidin), nucleic acids, affinity ligands, sugars, lipids, peptides, and substrates for enzymes. These formats are applicable to a wide variety of applications such as DNA microarrays, FISH assays, PCR assays, and also include the protein-based detection applications described above. The properties of the polymer materials further allow for the amplification of more than one dye using a single excitation wavelength (laser, filter, etc). This enables simultaneous detection of multiple targets (multiplexing). Further details relating to multichromophores and their uses are disclosed the following, each of which is incorporated herein by reference: U.S. patent application Ser. No. 11/329,495, filed Jan. 10, 2006, published as US 2006-0183140 A1; U.S. patent application Ser. No. 11/329,861, filed Jan. 10, 2006, published as US 2006-0216734 A1; U.S. patent application Ser. No. 11/344,942, filed Jan. 31, 2006, published as US 2006-0204984 A1; U.S. patent application Ser. No. 10/648,945, filed Aug. 26, 2003, published as US 2004-0142344 A1; U.S. patent application Ser. No. 10/600,286, filed Jun. 20, 2003, published as US 2004-0219556 A1; U.S. patent application Ser. No. 10/666,333, filed Sep. 17, 2003, published as US 2005-0059168 A1; and U.S. patent application Ser. No. 10/779,412, filed Feb. 13, 2004, published as US 2005-0003386 A1.

Before the present invention is described in further detail, it is to be understood that this invention is not limited to the particular methodology, devices, solutions or apparatuses described, as such methods, devices, solutions or apparatuses can, of course, vary. It is also to be understood that the terminology used herein is for the purpose of describing particular embodiments only, and is not intended to limit the scope of the present invention.

Use of the singular forms "a," "an," and "the" include plural references unless the context clearly dictates otherwise. Thus, for example, reference to "an aggregation sensor" includes a plurality of aggregation sensors, reference to "a probe" includes a plurality of probes, and the like. Additionally, use of specific plural references, such as "two," "three," etc., read on larger numbers of the same subject less the context clearly dictates otherwise.

Terms such as "connected," "attached," "conjugated" and "linked" are used interchangeably herein and encompass direct as well as indirect connection, attachment, linkage or conjugation unless the context clearly dictates otherwise; in one example, the phrase "conjugated polymer" is used in accordance with its ordinary meaning in the art and refers to a polymer containing an extended series of unsaturated bonds, and that context dictates that the term "conjugated" should be interpreted as something more than simply a direct or indirect connection, attachment or linkage.

Where a range of values is recited, it is to be understood that each intervening integer value, and each fraction thereof, between the recited upper and lower limits of that range is also specifically disclosed, along with each subrange between such values. The upper and lower limits of any range can independently be included in or excluded from the range, and each range where either, neither or both limits are included is also encompassed within the invention. Where a value being discussed has inherent limits, for example where a component can be present at a concentration of from 0 to 100%, or where the pH of an aqueous solution can range from 1 to 14, those inherent limits are specifically disclosed. Where a value is explicitly recited, it is to be understood that values which are about the same quantity or amount as the recited value are also within the scope of the invention, as are ranges based thereon. Where a combination is disclosed, each subcombination of the elements of that combination is also specifically disclosed and is within the scope of the invention. Conversely, where different elements or groups of elements are disclosed, combinations thereof are also disclosed. Where any element of an invention is disclosed as having a plurality of alternatives, examples of that invention in which each alternative is excluded singly or in any combination with the other alternatives are also hereby disclosed; more than one element of an invention can have such exclusions, and all combinations of elements having such exclusions are hereby disclosed.

Unless defined otherwise or the context clearly dictates otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

All publications mentioned herein are hereby incorporated by reference for the purpose of disclosing and describing the particular materials and methodologies for which the reference was cited. The publications discussed herein are provided solely for their disclosure prior to the filing date of the present application. Nothing herein is to be construed as an admission that the invention is not entitled to antedate such disclosure by virtue of prior invention.

Definitions

In describing the present invention, the following terms will be employed, and are intended to be defined as indicated below.

“Alkyl” refers to a branched, unbranched or cyclic saturated hydrocarbon group of 1 to 24 carbon atoms optionally substituted at one or more positions, and includes polycyclic compounds. Examples of alkyl groups include optionally substituted methyl, ethyl, n-propyl, isopropyl, n-butyl, s-butyl, t-butyl, n-pentyl, isopentyl, neopentyl, n-hexyl, n-heptyl, n-octyl, n-decyl, hexyloctyl, tetradecyl, hexadecyl, eicosyl, tetracosyl and the like, as well as cycloalkyl groups such as cyclopropyl, cyclobutyl, cyclopentyl, cyclohexyl, cycloheptyl, cyclooctyl, adamantyl, and norbornyl. The term “lower alkyl” refers to an alkyl group of 1 to 6 carbon atoms, preferably 1 to 4 carbon atoms. Exemplary substituents on substituted alkyl groups include hydroxyl, cyano, alkoxy, =O, =S, —$NO_2$, halogen, haloalkyl, heteroalkyl, carboxyalkyl, amine, amide, thioether and —SH.

“Alkoxy” refers to an “—Oalkyl” group, where alkyl is as defined above. A “lower alkoxy” group it tends an alkoxy group containing one to six, more preferably one to four, carbon atoms.

“Alkenyl” refers to a branched, unbranched or cyclic hydrocarbon group of 2 to 24 carbon atoms containing at least one carbon-carbon double bond optionally substituted at one or more positions. Examples of alkenyl groups include ethenyl, 1-propenyl, 2-propenyl (allyl), 1-methylvinyl, cyclopropenyl, 1-butenyl, 2-butenyl, isobutenyl, 1,4-butadienyl, cyclobutenyl, 1-methylbut-2-enyl, 2-methylbut-2-en-4-yl, prenyl, pent-1-enyl, pent-3-enyl, 1,1-dimethylallyl, cyclopentenyl, hex-2-enyl, 1-methyl-1-ethylallyl, cyclohexenyl, heptenyl, cycloheptenyl, octenyl, cyclooctenyl, decenyl, tetradecenyl, hexadecenyl, eicosenyl, tetracosenyl and the like. Preferred alkenyl groups herein contain 2 to 12 carbon atoms. The term “lower alkenyl” intends an alkenyl group of 2 to 6 carbon atoms, preferably 2 to 4 carbon atoms. The term “cycloalkenyl” intends a cyclic alkenyl group of 3 to 8, preferably 5 or 6, carbon atoms. Exemplary substituents on substituted alkenyl groups include hydroxyl, cyano, alkoxy, =O, =S, —$NO_2$, halogen, haloalkyl, heteroalkyl, amine, thioether and —SH.

“Alkenyloxy” refers to an “—Oalkenyl” group, wherein alkenyl is as defined above.

“Alkylaryl” refers to an alkyl group that is covalently joined to an aryl group. Preferably, the alkyl is a lower alkyl. Exemplary alkylaryl groups include benzyl, phenethyl, phenopropyl, 1-benzylethyl, phenobutyl, 2-benzylpropyl and the like.

“Alkylaryloxy” refers to an “—Oalkylaryl” group, where alkylaryl is as defined above.

“Alkenyl” refers to a branched or unbranched hydrocarbon group of 2 to 24 carbon atoms containing at least one —C/C— triple bond, optionally substituted at one or more positions. Examples of alkynyl groups include ethynyl, n-propynyl, isopropynyl, propargyl, but-2-ynyl, 3-methylbut-1-ynyl, octynyl, decynyl and the like. Preferred alkynyl groups herein contain 2 to 12 carbon atoms. The term “lower alkynyl” intends an alkynyl group of 2 to 6, preferably 2 to 4, carbon atoms, and one —C=C— triple bond. Exemplary substituents on substituted alkynyl groups include hydroxyl, cyano, alkoxy, =O, =S, —$NO_2$, halogen, haloalkyl, heteroalkyl, amine, thioether and —SH.

“Antibody” as referenced herein is used in the broadest sense, and specifically covers monoclonal antibodies (including full length monoclonal antibodies), polyclonal antibodies, multispecific antibodies (e.g., bispecific antibodies), and antibody fragments (e.g., Fab, $F(ab')_2$ and Fv) so long as they exhibit binding activity or affinity for a selected antigen.

“Antigen” as used herein refers to any substance capable of eliciting an immune response.

“Amide” refers to —C(O)NR'R", where R' and R" are independently selected from hydrogen, alkyl, aryl, and alkylaryl.

“Amine” refers to an —N(R')R" group, where R' and R" are independently selected from hydrogen, alkyl, aryl, and alkylaryl.

“Aryl” refers to an aromatic group that has at least one ring having a conjugated pi electron system and includes carbocyclic, heterocyclic, bridged and/or polycyclic aryl groups, and can be optionally substituted at one or more positions. Typical aryl groups contain 1 to 5 aromatic rings, which may be fused and/or linked. Exemplary aryl groups include phenyl, furaryl, azolyl, thiofuranyl, pyridyl, pyrimidyl, pyrazinyl, triazinyl, biphenyl, indenyl, benzofuranyl, indolyl, naphthyl, quinolinyl, isoquinolinyl, quinazolinyl, pyridopyridinyl, pyrrolopyridinyl, purinyl, tetralinyl and the like. Exemplary substituents on optionally substituted aryl groups include alkyl, alkoxy, alkylcarboxy, alkenyl, alkenyloxy, alkenylcarboxy, aryl, aryloxy, alkylaryl, alkylaryloxy, fused saturated or unsaturated optionally substituted rings, halogen, haloalkyl, heteroalkyl, —S(O)R, sulfonyl, —$SO_3R$, —SR, —$NO_2$, —NRR', —OH, —CN, —C(O)R, —OC(O)R, —NHC(O)R, —$(CH_2)_nCO_2R$ or —$(CH_2)_n$CONRR' where n is 0-4, and wherein R and R' are independently H, alkyl, aryl or alkylaryl.

“Aryloxy” refers to an “—Oaryl” group, where aryl is as defined above.

“Carbocyclic” refers to an optionally substituted compound containing at least one ring and wherein all ring atoms are carbon, and can be saturated or unsaturated.

“Carbocyclic aryl” refers to an optionally substituted aryl group wherein the ring atoms are carbon.

“Halo” or “halogen” refers to fluoro, chloro, aroma or iodo. “Halide” refers to the anionic form of the halogens.

“Haloalkyl” refers to an alkyl group substituted at one or more positions with a halogen, and includes alkyl groups substituted with only one type of halogen atom as well as alkyl groups substituted with a mixture of different types of halogen atoms. Exemplary haloalkyl groups include trihalomethyl groups, for example trifluoromemyl.

“Heteroalkyl” refers to an alkyl group wherein one or more carbon atoms and associated hydrogen atom(s) are replaced by an optionally substituted heteroatom, and includes alkyl groups substituted with only one type of heteroatom as well as alkyl groups substituted with a mixture of different types of heteroatoms. Heteroatoms include oxygen, sulfur, and nitrogen. As used herein, nitrogen heteroatoms and sulfur heteroatoms include any oxidized form of nitrogen and sulfur, and any form of nitrogen having four covalent bonds including protonated forms. An optionally substituted heteroatom refers to replacement of one or more hydrogens attached to a nitrogen atom with alkyl, aryl, alkylaryl or hydroxyl.

“Heterocyclic” refers to a compound containing at least one saturated or unsaturated ring having at least one heteroatom and optionally substituted at one or more positions. Typical heterocyclic groups contain 1 to 5 rings, which may be fused and/or linked, where the rings each contain five or six atoms. Examples of heterocyclic groups include piperidinyl, morpholinyl and pyrrolidinyl. Exemplary substituents for optionally substituted heterocyclic groups are as for alkyl and aryl at ring carbons and as for heteroalkyl at heteroatoms.

“Heterocyclic aryl” refers to an aryl group having at least 1 heteroatom in at least one aromatic ring. Exemplary heterocyclic aryl groups include furanyl, thienyl, pyridyl, pyridazinyl, pyrrolyl, N-lower alkyl-pyrrolo, pyrimidyl, pyrazinyl, triazinyl, tetrazinyl, triazolyl, tetrazolyl, imidazolyl, bipyridyl, tripyridyl, tetrapyridyl, phenazinyl, phenanthrolinyl, purinyl and the like.

"Hydrocarbyl" refers to hydrocarbyl substituents containing 1 to about 20 carbon atoms, including branched, unbranched and cyclic species as well as saturated and unsaturated species, for example alkyl groups, alkylidenyl groups, alkenyl groups, alkylaryl groups, aryl groups, and the like. The term "lower hydrocarbyl" intends a hydrocarbyl group of one to six carbon atoms, preferably one to four carbon atoms.

A "substituent" refers to a group that replaces one or mare hydrogens attached to a carbon or nitrogen. Exemplary substituents include alkyl, alkylidenyl, alkylcarboxy, alkoxy, alkenyl, alkenylcarboxy, alkenyloxy, aryl, aryloxy, alkylaryl, alkylaryloxy, —OH, amide, carboxamide, carboxy, sulfonyl, =O, =S, $—NO_2$, halogen, haloalkyl, fused saturated or unsaturated optionally substituted rings, —S(O)R, $—SO_3R$, —SR, —NRR', —OH, —CN, —C(O)R, —OC(O)R, —NHC(O)R, $—(CH2)_nCO_2R$ or $—(CH2)_nCONRR'$ where n is 0-4, and wherein R and R' are independently H, alkyl, aryl or alkylaryl. Substituents also include replacement of a carbon atom and one or mare associated hydrogen atoms with an optionally substituted heteroatom.

"Sulfonyl" refers to $—S(O)_2R$, where R is alkyl, aryl, —C(CN)=C-aryl, $—H_2CN$, alkylaryl, or amine.

"Thioamide" refers to —C(S)NR'R", where R' and R" are independently selected from hydrogen, alkyl, aryl, and alkylaryl.

"Thioether" refers to —SR, where R is alkyl, aryl, or alkylaryl.

As used herein, the term "binding pair" refers to first and second molecules that bind specifically to each other with greater affinity than to other components in the sample. The binding between the members of the binding pair is typically noncovalent. Exemplary binding pairs include immunological binding pairs (e.g. any haptenic or antigenic compound in combination with a corresponding antibody or binding portion or fragment thereof, for example digoxigenin and anti-digoxigenin, fluorescein and anti-fluorescein, dinitrophenol and anti-dinitrophenol, bromodeoxyuridine and anti-bromodeoxyuridine, mouse immunoglobulin and goat anti-mouse immunoglobulin) and nonimmunological binding pairs (e.g., biotin-avidin, biotin-streptavidin, hormone [e.g., thyroxine, and cortisol]-hormone binding protein, receptor-receptor agonist or antagonist (e.g., acetylcholine receptor-acetylcholine, or an analog thereof) IgG-protein A, lectin-carbohydrate, enzyme-enzyme cofactor, enzyme-enzyme-inhibitor, and complementary polynucleotide pairs capable of forming nucleic acid duplexes) and the like. One or both member of the binding pair can be conjugated to additional molecules.

The terms "polynucleotide," "oligonucleotide," "nucleic acid" and "nucleic acid molecule" are used interchangeably herein to refer to a polymeric form of nucleotides of any length, and may comprise ribonucleotides, deoxyribonucleotides, analogs thereof, or mixtures thereof. These terms refer only to the primary structure of the molecule. Thus, the terms includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. Additional details for these terms as well as for details of base pair formation can be found in U.S. application Ser. No. 11/344,942, filed Jan. 31, 2006 which is incorporate herein by reference in its entirety.

"Complementary" or "substantially complementary" refers to the ability to hybridize or base pair between nucleotides or nucleic acids, such as, for instance, between a sensor peptide nucleic acid and a target polynucleotide. Complementary nucleotides are, generally, A and T (or A and U), or C and G. Two single-stranded polynucleotides or PNAs are said to be substantially complementary when the bases of one strand, optimally aligned and compared and with appropriate insertions or deletions, pair with at least about 80% of the bases of the other strand, usually at least about 90% to 95%, and more preferably from about 98 to 100%.

Alternatively, substantial complementarity exists when a polynucleotide or PNA will hybridize under selective hybridization conditions to its complement. Typically, selective hybridization will occur when there is at least about 65% complementary over a stretch of at least 14 to 25 bases, preferably at least about 75%, more preferably at least about 90% complementary. See, M. Kanehisa Nucleic Acids Res. 12:203(11984).

"Preferential binding" or "preferential hybridization" refers to the increased propensity of one polynucleotide or PNA to bind to its complement in a sample as compared to a noncomplementary polymer in the sample.

Hybridization conditions for polynucleotides will typically include salt concentrations of less than about 1M, more usually less than about 500 mM and preferably less than about 200 mM. In the case of hybridization between a peptide nucleic acid and a polynucleotide, the hybridization can be done in solutions containing little or no salt. Hybridization temperatures can be as low as 5° C., but are typically greater than 22° C., more typically greater than about 30° C., and preferably in excess of about 37° C. Longer fragments may require higher hybridization temperatures for specific hybridization. Other factors may affect the stringency of hybridization, including base composition and length of the complementary strands, presence of organic solvents and extent of base mismatching, and the combination of parameters used is more important than the absolute measure of any one alone. Other hybridization conditions which may be controlled include buffer type, and concentration, solution pH, presence and concentration of blocking reagents to decrease background binding such as repeat sequences or blocking protein solutions, detergent type(s) and concentrations, molecules such as polymers which increase the relative concentration of the polynucleotides, metal ion(s) and their concentration(s), chelator(s) and their concentrations, and other conditions known in the art.

"Multiplexing" herein refers to an assay or other analytical method which multiple analytes can be assayed simultaneously.

"Having" is an open ended phrase like "comprising" and "including," and includes circumstances where additional elements are included and circumstances where they are not.

"Optional" or "optionally" means that the subsequently described event or circumstance may or may not occur, and that the description includes instances where the event or circumstance occurs and instances in which it does not.

The invention disclosed herein relates generally to assays and complexes including multichromophores, and signaling chromophores useful for the identification of target biomolecules or biomolecules associated with target molecules through enhanced signal amplifications.

In general, in one aspect the invention includes multi-chromophore energy transfer to a dye on a sensor which can be a biomolecule including a bioconjugate (e.g., an antibody).

In one embodiment an approach modifying a format as followed in relation to nucleic acid sensor assays as described in Gaylord, Heeger. and Bazaar, J. Am. Chem. Soc., 2003 can be followed. Specifically, signal amplification of multichromophore can be based on nonspecific elecostatic binding events to indicate a hybridization event. Any established multichromophore can be chosen as the donor, and one or more dye, preferably a dye with a history of efficient energy transfer, for example, fluorescein and Cy3, can be chosen as the acceptors. It is envisioned that the dye can be directly conjugated to a sensor molecule. As shown schematically in FIG. 1, the sensor can be a biomolecule (e.g., an antibody) in a solution or on a substrate, to which multichromophore can be added. In the embodiment shown in FIG. 1, a dye can be covalently linked (bioconjugated) to an antibody (Y-shaped structure), which possesses a net negative charge. Addition of cationic multichromophore (shown as wavy lines) can result in electrostatic binding between the multichromophore and the antibody, bringing the multichromophore and dye into close proximity. Distance requirements for fluorescence resonance energy transfer (FRET) can thus be met, and excitation of the polymer with light (shown as hv) results in amplified dye emission. It is envisioned that the multichromophore can be excited at a wavelength where the dye does not have significant absorbance. In one embodiment the dye emission can be at a longer wavelength than the multichromophore emission. In use it is envisioned that an assay method can include the steps of providing a sample that is suspected of containing a target biomolecule, providing a sensor conjugated to a signaling chromophore and capable of interacting with the target biomolecule, providing a multichromophore that electrostatically interacts with the sensor and upon excitation is capable of transferring energy to the sensor signaling chromophore and contacting the sample with the sensor and the multichromophore in a solution under conditions in which the sensor can bind to the target biomolecule if present. Next, the method can include applying a light source to the sample that can excite the multichromophore, and detecting whether light is emitted from the signaling chromophore.

Figure 2:
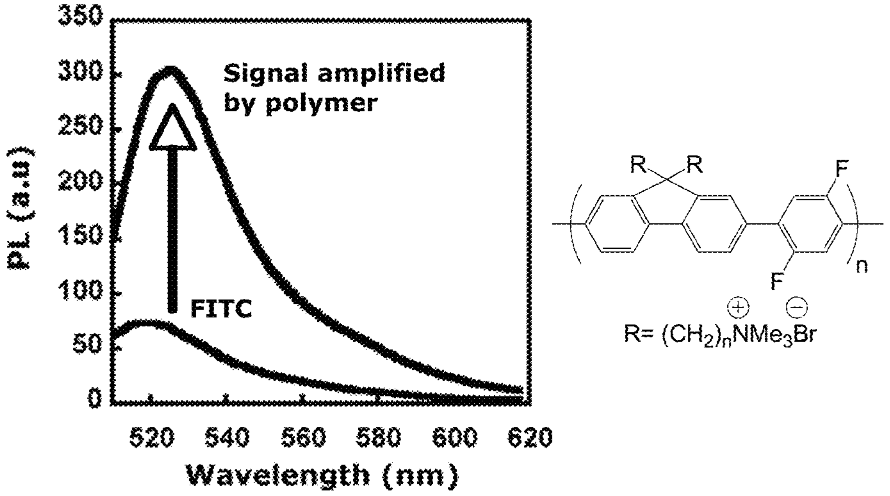
FIG. 2. Plot of direct excitation of a FITC-labeled antibody illustrating amplified dye emission (left) and a schematic of the structure of a multichromophore of one embodiment of the invention (right).

An example of data produced from the embodiment shown in FIG. 1 is presented in FIG. 2. As shown in the graph a FITC-labeled mouse-anti-human CD22 antibody can be excited both directly (lower line, labeled FITC) or indirectly through excitation of and electrostatically bound multichromophore (structure shown in FIG. 2, right) and subsequent energy transfer via FRET (upper line, labeled Signal amplified by polymer). The particulars of the experiment included direct excitation of a FITC-labeled mouse-anti-human CD22 antibody (lower line, labeled FITC, 496 nm excitation, [FITC-labeled mouse-anti-human CD22]=1 ng/mL) and multichromophore-amplified dye emission (upper line, 380 nm excitation, [multichromophore]=$1\times10^{-6}$ M in repeat units, RU) in 2 mL of 1×SSPE. The structure of the donor multichromophore is illustrated to the right of the graph. Advantageously, energy transfer in the presence of multichromophore resulted in 5-fold amplification of the dye signal intensity, as compared with direct excitation.

Figure 3:
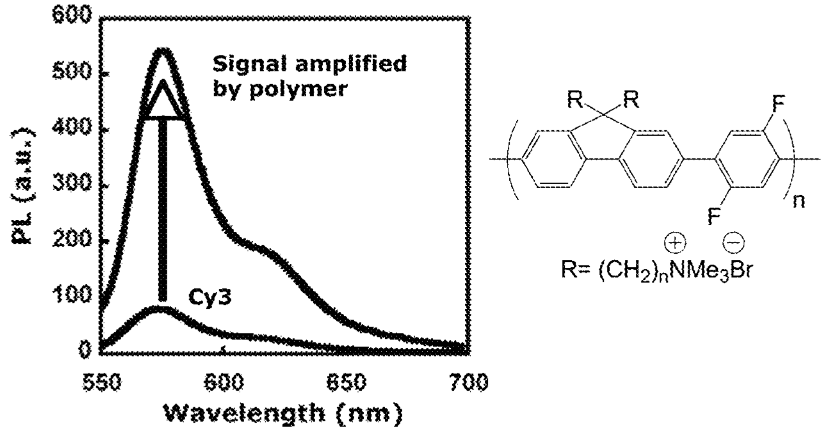
FIG. 3. Plot of direct excitation of a Cy3, labeled antibody illustrating amplified dye emission (left) and a schematic of the structure of a multichromophore of one embodiment of the invention (right).

FIG. 3 illustrates a second example of data produced from the embodiment shown in FIG. 1. Here, the graph shows a comparison of optical reporting signals for direct (lower line, labeled Cy3, 540 nm excitation) and indirect (upper line, 380 nm excitation) excitation of a Cy3-labeled donkey-anti-mouse secondary antibody. Experimental conditions were similar to those for the prior experiment, but with half the volume. The donor multichromophore structure is shown in FIG. 3, right side. Multichromophore-amplified dye intensities were 10-fold more intense when compared with direct excitation of the dye.

As disclosed herein, electrostatic binding between charged multichromophores and dye-labeled antibodies can be a viable approach for increasing detection sensitivities, for example of a biomolecule target. In a further embodiment, covalently attaching the multichromophore to a dye/biomolecule (e.g., an antibody complex offers several advantages including reduced background and improved energy transfer. In the case of direct linkage to a biomolecule, biorecognition events, rather than electrostatic binding events, should govern multichromophore presence. In this manner, nonspecific binding of multichromophore to biomolecules can be eliminated, reducing any background emission resulting from the multichromophore itself. The abovementioned biomolecules include but are not limited to proteins, peptides, affinity ligands, antibodies, antibody fragments, sugars, lipids, and nucleic acids (as hybridization probes and/or aptamers).

In the case of direct linkage to a dye or biomolecule/dye complex, donor-acceptor distances can be fixed, rather than dependent on the strength of electrostatic binding, and energy transfer efficiency can be significantly increased. This has significant consequences in the context of improving dye signaling and reducing background fluorescence associated with donor-acceptor cross-talk. Cross-talk in this case refers to the overlap between multichromophore (donor) and dye (acceptor) emission peaks. Multichromophores which bind non-specifically at distances too great for energy transfer can contribute to the background fluorescence (or crosstalk). Shorter (fixed) distances between the donor and acceptor can not only facilitate direct dye amplification, but also can greatly quench the donor emission. This results in less donor emission at the acceptor emission wavelengths, which subsequently reduces or even eliminates the need for cross-talk correction.

Figure 4:
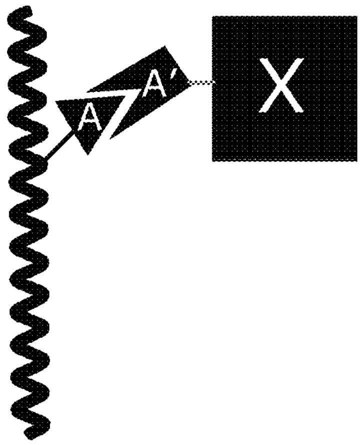
FIG. 4. Schematic of a bioconjugated multichromophore of one embodiment of the invention.

In general, in another aspect the invention includes the bioconjugation of multichromophore to affinity ligands (affinity ligands describing a biomolecule that has an affinity for another biomolecule). FIG. 4 illustrates a class of materials in which a multichromophore (shown as a wavy line) is linked to a dye, biomolecule, or biomolecule/dye complex (labeled X). Linking to the multichromophore can be via a first functionality linker A on the multichromophore that serves as a bioconjugation site capable of covalently linking with a second functionality linker A' linked to a biomolecule and/or dye (see X). This arrangement can fix the distance between the multichromophore and X, thereby ensuring only specific interactions between multichromophore and X. It is envisioned that a biomolecule component X in this embodiment can be any of the various biomolecules disclosed herein, including but not limited to an antibody, protein, affinity ligand, or nucleic acid.

It is envisioned that the X in this context can be, but is not limited to, a dye, fluorescence protein, nanomaterial Quantum Dot), a conjugate between dye and chemluminescence-generating molecule, a conjugate between fluorescence protein and chemluminescence-generating molecule, a conjugate between nanomaterial (e.g., Quantum Dot) and chemluminescence-generating molecule, streptavidin, avidin, enzyme, substrate for an enzyme, substrate analog for an enzyme, receptor, ligand for a receptor, ligand analog for a receptor, DNA, RNA, modified nucleic acid, DNA aptamer, RNA aptamer, modified nucleic aptamer, peptide aptamer, antibody, antigen, phage, bacterium or conjugate of any two of the items described above.

The linking chemistry for A-A' and B-B' can include, but not limited to, maleimidelthiol, succimidylester (NHS ester)/amine, azide chemistry, carboxy/EDC (1-Ethyl-3-[3-dimethylaminopropyl]carbodiimide Hydrochloride)/amine, amine/Sulfo-SMCC (Sulfosuccinimidyl 4-[N-maleimidomethyl]cyclohexane-1-carboxylate)/thiol, and amine/BMPH (N-[β-Maleimidopropionic acid]hydrazide·TFA)/thiol.

Figure 5:
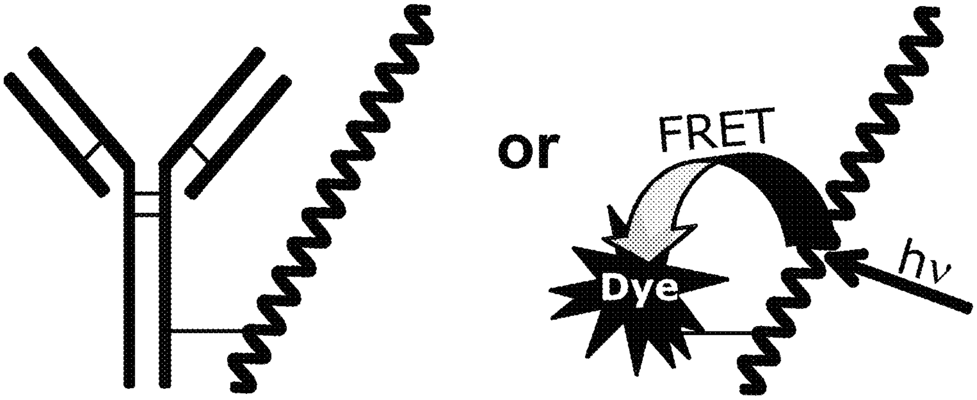
FIG. 5. Schematic of a multichromophore conjugated to an antibody (left) or a dye (right).

In another aspect, the invention includes labeled multichromophores. FIG. 5 shows two examples of labeled multichromophores. In one embodiment, on the left, a multichromophore (shown as a wavy line) is shown conjugated to an antibody which can be, for example, a 1° or 2° antibody. The conjugate of the multichromophore and the antibody can be used as a reporter, for example, in a assay. Excitation of the multichromophore with light (not shown) can result in multichromophore emission, indicating the presence of the antibody (1° or 2°). In another embodiment shown in FIG. 5 on the right, the multichromophore is labeled with a dye, for example, a chromophore. In this case, the multichromophore can act as a donor and the dye can act as an acceptor in a FRET process as shown. Here, the multichromophore can act as a light harvester, and excitation of the multichromophore is followed by the channeling of the excitations to the dye via a FRET process. This results in amplified dye emission (as compared to direct excitation of the dye). The fluorescence of the donor multichromophore, in one embodiment, can be quenched (e.g., >90% quenching).

Figure 6:
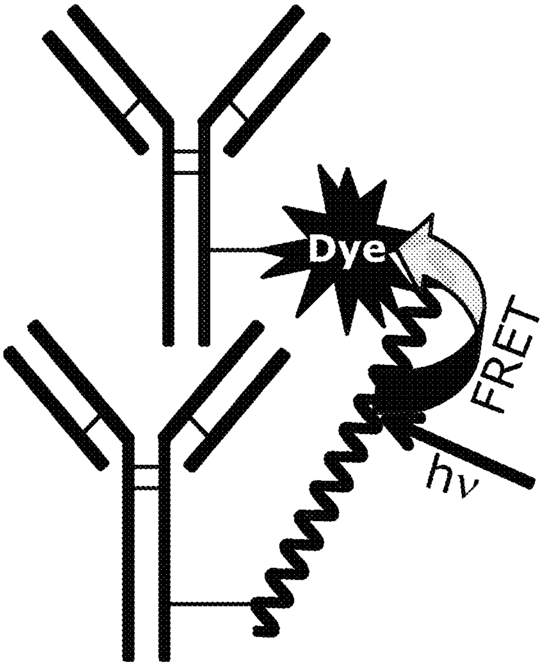
FIG. 6. Schematic of a multichromophore conjugated to a secondary antibody binding to a primary antibody labeled with dye.

In general, in another aspect the invention includes a method of assaying for a target biomolecule or a tagged target biomolecule. As shown in FIG. 6 in one embodiment a multichromophore (shown as a wavy line) can be linked to a first bioconjugate (shown as a Y-shaped object), for example, a 2° antibody that is specific for second a dye-labeled bioconjugate, for example, a 1° antibody. Here, the recognition event between the 1° and 2° antibody will result in the reduction of distance between the donor multichromophore and acceptor dye. After this recognition event, excitation of the donor multichromophore with light (shown as hv) will result in FRET to the acceptor dye (shown as curved arrow), and amplified dye emission (in comparison with direct excitation of the dye) will be observed. In use it is envisioned that an assay method could include providing a sample that is suspected of containing a target biomolecule by the steps of providing a first bioconjugate, for example, a 1° antibody conjugated to a signaling chromophore and capable of interacting with the target biomolecule. This is followed by providing a second bioconjugate, for example, a 2° antibody, conjugated to a multichromophore, wherein the second bioconjugate can bind to the first bioconjugate and wherein upon such binding excitation of the multichromophore is capable of transferring energy to the signaling chromophore. Next, the method includes contacting the sample with the first bioconjugate in a solution under conditions in which the first bioconjugate can bind to the target biomolecule if present and contacting the solution with the second bioconjugate. The method then includes applying a light source to the target biomolecule or tagged target biomolecule, wherein the light source can excite the multichromophore and subsequently detecting whether light is emitted from the signaling chromophore.

Figure 7:
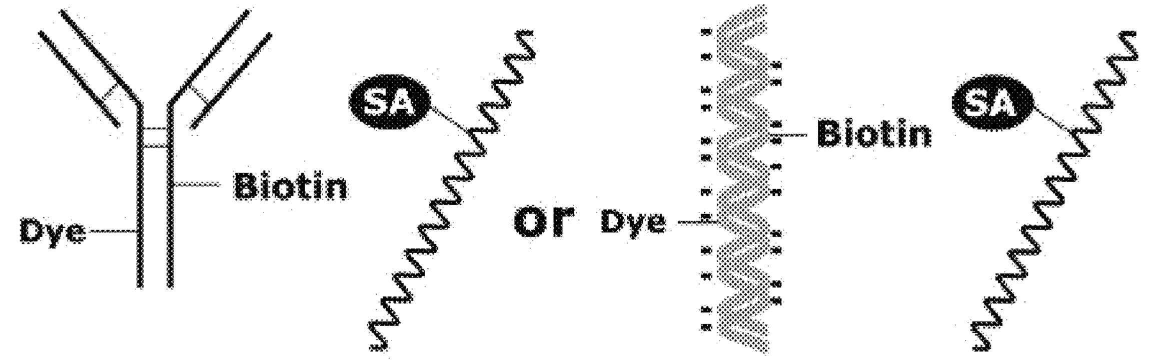
FIG. 7. Schematic of a multichromophore conjugated to streptavidin for binding to a dye- and biotin-labeled primary antibody (left) or a dye- and biotin-labeled nucleic acid (right).

In general in another aspect, the invention includes a method of assaying a sample using a multichromophore and a sensor biomolecule complex. As shown in FIG. 7, left side, a multichromophore (shown as a wavy line) can be conjugated to a first bioconjugate, for example, streptavidin (SA) which has a strong affinity for biotin. In FIG. 7 on the left, a sensor biomolecule (e.g., an antibody which can be a 1° or 2° antibody), is conjugated to both a dye and a second bioconjugate (e.g., a biotin moiety). After a biorecognition event between the first and second bioconjugates (e.g. between SA and biotin), the multichromophore and dye will be brought into close proximity, and excitation of the donor multichromophore will result in FRET to the acceptor dye. Dye emission will indicate the presence of the first bioconjugate (e.g., the antibody). In comparison with direct excitation of the dye, amplification of the dye signal intensity will be observed when excited indirectly through FRET.

In another embodiment as shown in FIG. 7, right, a sensor biomolecule, for example, a nucleic acid, is conjugated to both a dye and a first bioconjugate (e.g., a biotin moiety). After a biorecognition event between a second bioconjugate SA) and the first bioconjugate (e.g., biotin), the multichromophore and dye will be brought into close proximity, and excitation of the donor multichromophore will result in FRET to the acceptor dye. In comparison with direct excitation of the dye, amplification of the dye signal intensity will be observed when excited indirectly through FRET. Dye emission will indicate the presence of the sensor biomolecule (e.g., a nucleic acid).

A method of using the embodiment shown in FIG. 7 can include the steps of providing a sample that is suspected of containing a target biomolecule, providing a multichromophore comprising a covalently linked first bioconjugate (e.g., SA), providing a sensor biomolecule complex comprising a sensor biomolecule capable of interacting with the target molecule, a signaling chromophore, and covalently linked second bioconjugate capable of binding with the first bioconjugate, wherein upon such binding excitation of the multichromophore is capable of transferring energy to the signaling chromophore. The method can further include the steps of contacting the sample with the sensor biomolecule complex in a solution under conditions in which the sensor biomolecule can bind to the target biomolecule if present, contacting the solution with the multichromophore, applying a light source to the sample that can excite the multichromophore, and detecting whether light is emitted from the signaling chromophore.

Figure 8:
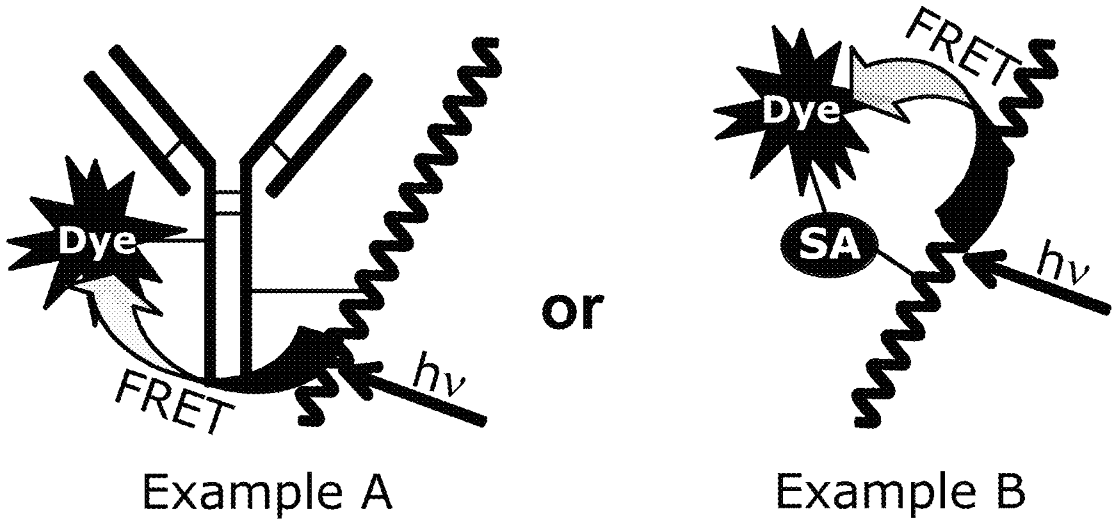
FIG. 8. Schematic of multichromophore conjugated to an antibody that is conjugated to a dye (left) and a multichromophore conjugated to streptavidin that is conjugated to a dye (right).

In general in another aspect, the invention provides a biorecognition complex for identifying a biomolecule including a bioconjugate a signaling chromophore and a multichromophore. FIG. 8 shows a multichromophore conjugated directly to a dye-labeled bioconjugate, e.g., an antibody (left). FIG. 8 further shows an alternative embodiment wherein a multichromophore is conjugated to a dye-labeled SA (right). In the embodiment illustrated on the left, covalent linkages between the bioconjugate (shown as Y-shaped) and the dye and multichromophore ensure the close proximity of the donor multichromophore and acceptor dye. Upon a biorecognition event between the bioconjugate, for example, an antibody, and its target, for example an antigen, excitation of the donor multichromophore will result in FRET to the acceptor dye. In one alternative embodiment, illustrated in FIG. 8 on the right, the multichromophore and dye remain in fixed, close proximity. As such, upon a binding event, for example, between the SA and a biotin moiety, excitation of the donor multichromophore will result in FRET to the acceptor dye. In either embodiment illustrated in FIG. 8, amplified dye emission should result from multichromophore excitation.

Figure 9:
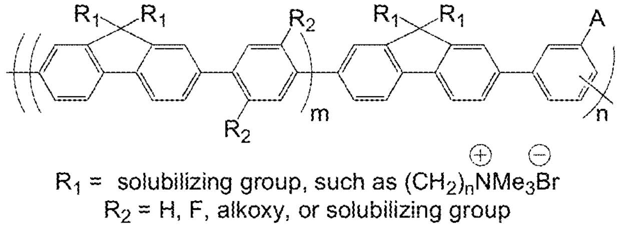
FIG. 9. Schematic of the structure of a multichromophore of one embodiment of the invention.

A non-limiting example of a CP structure is shown in FIG. 9. The backbone can consists mainly of fluorene-phenylene repeat units and serves as the donor in the FRET process. The CP is functionalized with R1 and R2 groups. Both can serve to solubilize the CP with hydrophilic groups, including but not limited to quaternary amines or PEG-type functionalities, while R2 can also serve to tune the optical properties via energy level modifications. A third co-monomer phenyl group functionalized with a site A allows for bioconjugation to a dye or biomolecule. The linker A can be but is not limited to a maleimide, thiol, succimidyl ester (or NHS-ester), amine, azide, biotin, avidin/streptavidin, or some other ligand-receptor that will react with an A' linker that is available on a biomolecule or dye (see e.g., as in FIG. 4).

Figure 10:
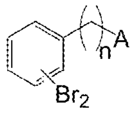
FIG. 10. Schematic of a monomer having a bioconjugation site of one embodiment of the invention.

A unique monomer that allows for the synthesis of the exemplary polymer of FIG. 9 is shown in FIG. 10. This monomer has two sites for Suzuki couplings (see Liu and Bazan. J. Am. Chem. Soc., 2005; Liu and Bazan, Proc. Natl. Acad. Sci., U.S.A., 2005; Bazan, Liu, U.S. Provisional Application No. 60/666,333, filed Sep. 17, 2000, and importantly, a site A that allows for bioconjugation. Site A can be a bioconjugation site self, or a precursor, such as a phthalimide protected amine).

Figure 11:
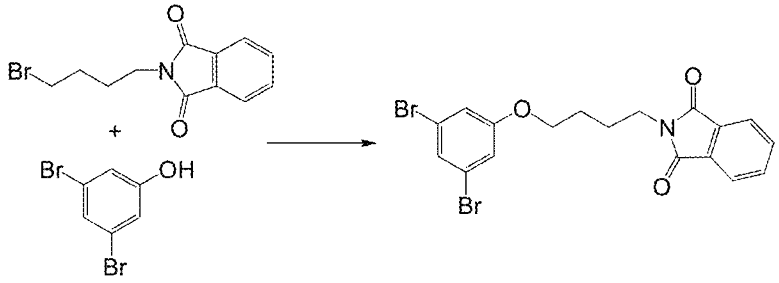
FIG. 11. Schematic of a synthetic route to a monomer of one embodiment of the invention.
Figure 12:
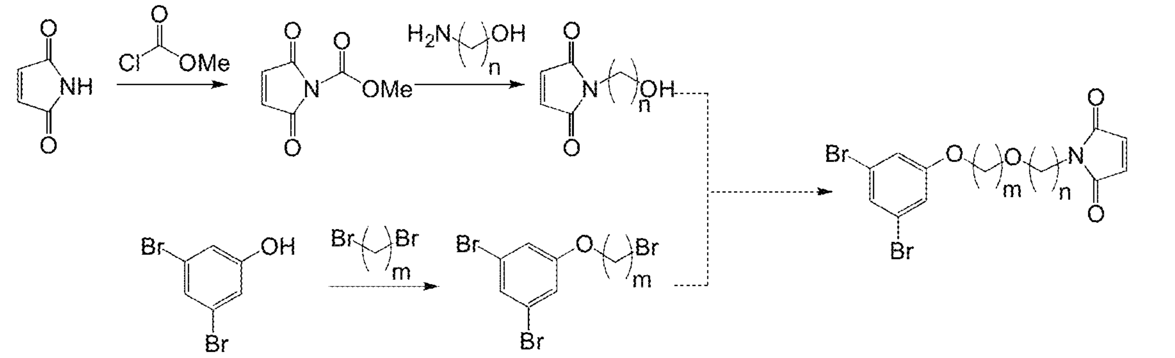
FIG. 12. Schematic of a synthetic route to a monomer of another embodiment of the invention.

Several examples of suitable monomer syntheses are illustrated in FIGS. 11 and 12. FIG. 11 schematically shows the synthesis of a monomer with a phthalimide functionality, which serves as a protected amine. FIG. 12 describes the synthesis of a monomer with a maleimide, which can be bioconjugated to thiols.

Examples for the syntheses of two monomeric structures for polymerization follow. The first is a one-step synthesis for a monomer functionalized with a protected amine (in the form of a phthalimide) for bioconjugation to succimidyl esters, and the second is a four-step synthesis for a monomer functionalized with a maleimide for bioconjugation to thiols.

N-4'-(3",5"-dibromophenoxy)butylphthalimide or 1-(4'-phthalimidobutoxy)3,5-dibromobenzene. 3,5-dibromophenol (970 mg, 3.85 mmol) was recrystallized from hexanes. After removal of solvent, N-(4-bromobutyl)phthalimide (1.38 g, 4.89 mmol), $K_2CO_3$ (1.88 g, 13.6 mmol), 18-crown-6 (53 mg, 0.20 mmol), and acetone (20 mL) were added. This was refluxed for 1 hour, and then poured into 100 mL of water. The aqueous layer was extracted with dichloromethane (4×30 mL). The organic layers were combined, washed with water, saturated $NaHCO_3$, and brine, then dried over $MgSO_4$ and filtered. Removal of solvent yielded a white solid, which was purified by column chromatography (4:1 hexanes:$CH_2Cl_2$) followed by recrystallization in hexanes to yield colorless needles (650 mg, 87%).

N-Methoxycarbonylmaleimide. Maleimide (2.00 g, 20.6 mmol) and N-methyl morpholine (2.08 g, 20.6 mmol) in ethyl acetate were cooled to 0° C. Dropwise addition of methylchloroformate (1.4 mL, 20.7 mmol) produced white precipitate. The solution was stirred for 1 hour at 0° C., after which the solids were removed by filtration. Concentration of filtrate yielded a pink oil, which was purified by column chromatography (eluant 3:1 hexanes:ethyl acetate) to yield pale yellow crystals.

N-(ω-hydroxyhexyl)maleimide. 6-amino-1-hexanol and saturated $NaHCO_3$ (20 mL) were cooled to 0° C. N-Methoxycarbonylmaleimide was added in portions with stirring. Solids did not fully dissolve. This was stirred for 30 minutes at 0° C. (most solids dissolved after 20 minutes), then the ice bath removed and solution stirred for an additional 30 minutes, at which point the solution was pale pink. This was diluted 3-fold with water and washed with chloroform (3×40 mL), dried over $MgSO_4$, filtered, and the solvent removed via rotary evaporation.

1-(6'-Bromohexyloxy)-3,5-dibromobenzene. 3,5-Dibromophenol was recrystallized from hexanes. After removal of solvent, 1,6-dibromohexane, $K_2CO_3$, 18-crown-6, and acetone were added. This was refluxed for 1 hour, and then poured into 100 mL of water. The aqueous layer was extracted with dichloromethane (4×30 mL). The organic layers were combined, washed with water, saturated $NaHCO_3$, and brine, then dried over $MgSO_4$ and filtered. Removal of solvent yielded an off-white solid, which was purified by column chromatography to yield a white solid.

1-(6'-(6"Maleimidohexyloxy)hexyloxy)-3,5-dibromobenzene. N-(ω-hydroxyhexyl)maleimide, 1-(6'-Bromohexyloxy)-3,5-dibromobenzene, $K_2CO_3$, 18-crown-6, and acetone will be refluxed for 1 hour, and then poured into 100 mL of water. The aqueous layer will be extracted with dichloromethane (4×30 mL). The organic layers will be combined, washed with water, saturated $NaHCO_3$, and brine, then dried over $MgSO_4$ and filtered. Removal of solvent will yield crude material, which will be purified by column chromatography to yield purified product.

Figure 13:
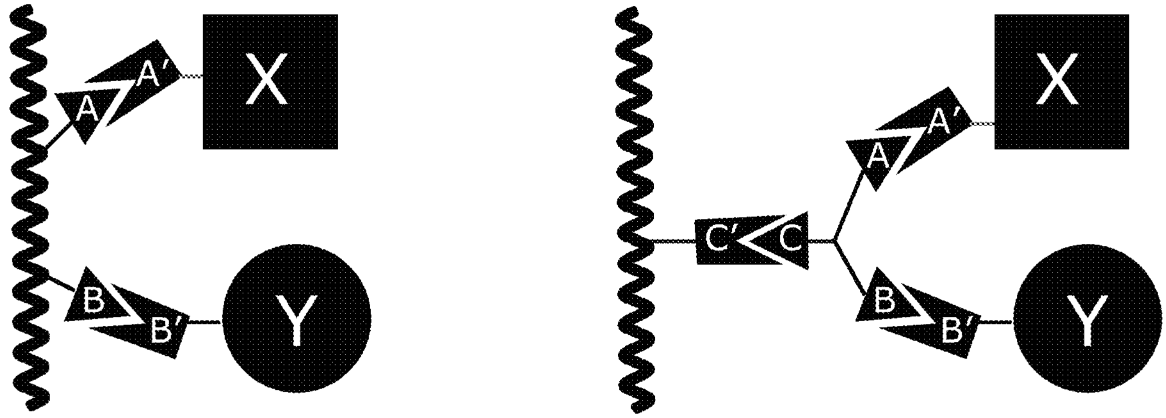
FIG. 13. Schematic of a multichromophore bioconjugated to a dye and a biomolecule via linkers (left) or via a tri-functionalized linker (right).

In general, in another aspect the invention provides a multichromophore complex including a multichromophore, sensor biomolecule and a signaling chromophore for identifying a target biomolecule. As depicted in FIG. 13, in one embodiment a multichromophore can be bioconjugated to both a dye and a biomolecule, for example a biorecognition molecule. Useful biomolecules can include but are not limited to antibodies, affinity ligands, nucleic acids, proteins, nanoparticles or substrates for enzymes. The benefits of covalently linking a dye in proximity to a multichromophore have been described above. By affixing both an acceptor dye and a biorecognition molecule to a multichromophore, the benefits are two fold, by both fixing donor-acceptor distances, such that an acceptor is guaranteed to be within the vicinity of a donor multichromophore (and vice versa), and also increasing the specificity of multichromophore binding to indicate a biorecognition event. These covalent complexes can be made via the monomer and linking chemistries described herein.

As shown in FIG. 13, left, in one embodiment a multichromophore (wavy line) can be bioconjugated to a dye X via linker functionalities A-A' and a biomolecule Y via linker functionalities B-B'. In an alternative embodiment shown in FIG. 13, right, a multichromophore can be bioconjugated to a dye X and a biomolecule Y by a trifunctionalized linker via linker functionalities A-A', B-B', and C-C'. In the embodiment illustrated in FIG. 13, the X can be, but is not limited to, a dye, fluorescence protein, nanomaterial (e.g., Quantum Dot), a conjugate between dye and chemluminescence-generating molecule, a conjugate between fluorescence protein and chemluminescence-generating molecule, or a conjugate between nanomaterial (e.g., Quantum Dot) and chemluminescence-generating molecule. The Y can be, but is not limited to, a streptavidin, avidin, enzyme, substrate for an enzyme, substrate analog for an enzyme, receptor, ligand for a receptor, ligand analog for a receptor, DNA, RNA, modified nucleic acid. DNA aptamer, RNA aptamer, modified nucleic aptamer, peptide aptamer, antibody, antigen, phage, bacterium or conjugate of any two of the items described above.

The linking chemistry for A-A', B-B' and C-C' can include, but is not limited to, maleimide/thiol, succimidylester (NHS ester)/amine, azide chemistry, carboxy/EDC (1-Ethyl-3-[3-dimethylaminopropyl]carbodiimide Hydrochloride)/amine, amine/Sulfo-SMCC (Sulfosuccinimidyl 4-[N-maleimidomethyl]cyclohexane-1-carboxylate)/thiol, and amine/BMPH (N-[β-Maleimidopropionic acid] hydrazide·TFA)/thiol. A tri-functional linker such as the commercially available Sulfo-SBED Sulfosuccinimidyl[2-6-(biotinamido)-2-(p-azidobenzamido)-hexanoamido]-ethyl-1,3'-dithiopropionate can serve well in the three way linkage among X, Y, and multichromophore.

In use, the embodiments shown in FIG. 13 can be a multichromophore, complex for identifying a target biomolecule wherein the complex includes a multichromophore, a signaling chromophore covalently linked to the multichromophore, and a sensor biomolecule covalently linked to the multichromophore. The signaling chromophore, of the complex is capable of receiving energy from the multichromophore upon excitation of the multichromophore and the sensor biomolecule is capable of interacting with the target biomolecule. It is envisioned that the biomolecules can include but are not limited to an antibody, protein, affinity ligand, peptide, or nucleic acid.

Figure 14:
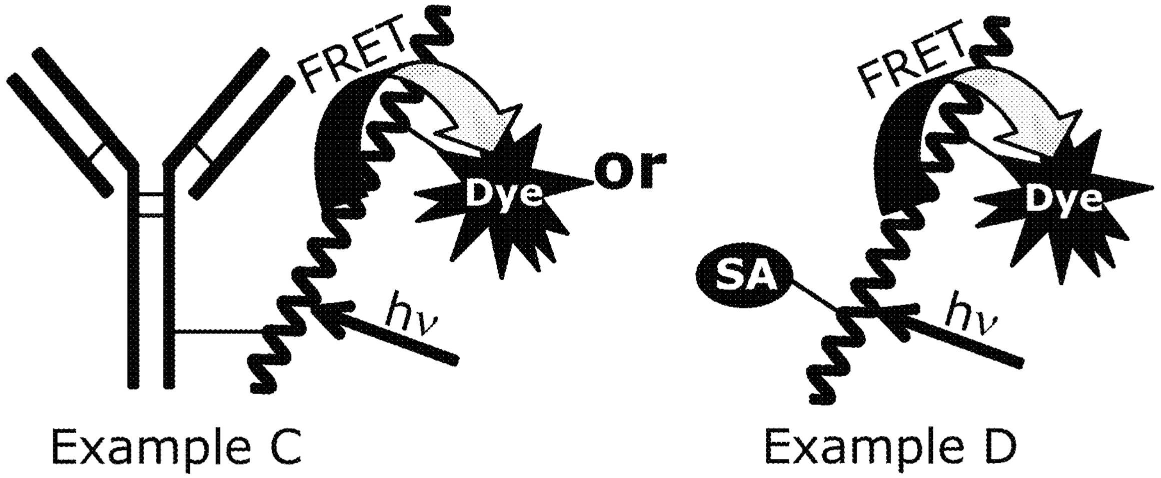
FIG. 14. Schematic of a multichromophore conjugated to both a dye and an antibody (left) and a multichromophore conjugated to both a dye and a protein (right).

In general, in another aspect the invention provides a biorecognition complex for identifying a biomolecule wherein the complex includes a bioconjugate, a multichromophore and a signaling chromophore. In one embodiment shown in FIG. 14, left, a multichromophore is conjugated to both a bioconjugate, for example, an antibody (1° or 2°) and a dye. Covalent linkage between the donor multichromophore and acceptor dye ensures close proximity. Excitation of the donor multichromophore results in FRET to the acceptor dye. Where the bioconjugate is an antibody, if the antibody binds to its target (e.g., antigen), this will be indicated by dye emission upon donor multichromophore excitation. In an alternative embodiment, as shown in FIG. 14, right, a multichromophore can be conjugated to both a SA and a dye. Again, covalent linkage between the donor multichromophore and acceptor dye ensure close proximity, and excitation of the donor multichromophore results in FRET to the acceptor dye. The SA complex can be used to label or detect a biotin-labeled biomolecule such as a biotinylated antibody or nucleic acid. Multichromophore excitation followed by FRET to the dye label will result in greatly enhanced detection signals (i.e., greater sensitivity).

Figure 16:
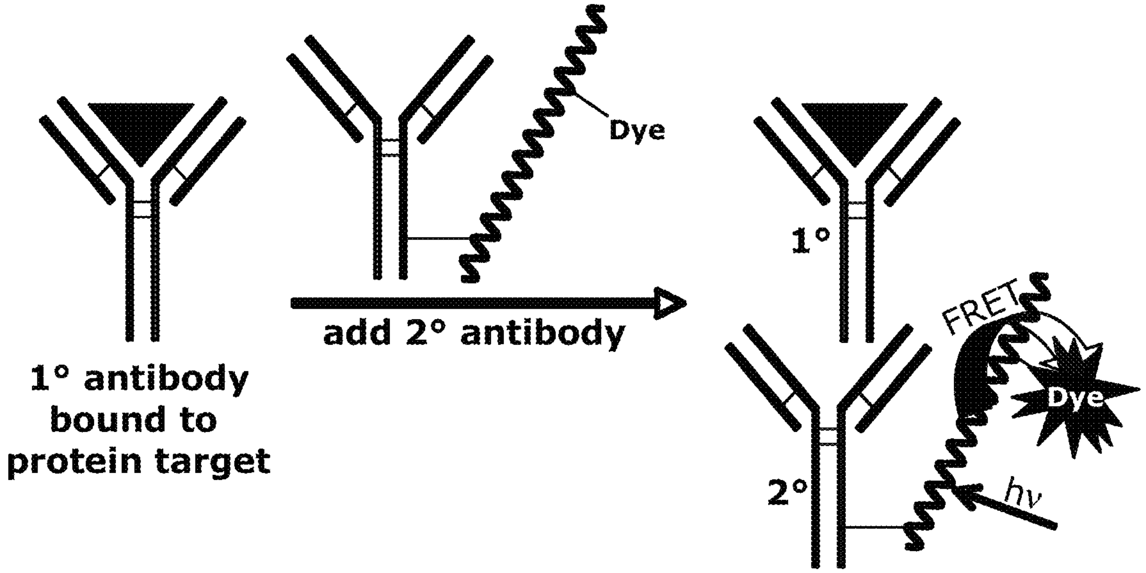
FIG. 16. Schematic of a multichromophore linked to a dye and a secondary antibody specific for a primary antibody targeting a protein.

FIG. 16 shows an example of a dual-labeled multichromophore (shown as wavy line), bioconjugated to both a reporter dye and a 2° antibody (Y-shaped structure). In an assay, an unlabeled 1° antibody can bind to a an antigen, for example, a target protein (shown as a black triangle). Addition of the 2° antibody, which is conjugated to a multichromophore, and further conjugated to a dye, can bind specifically to the 1° antibody. Optical excitation of the multichromophore can result in energy transfer to the dye, and amplified dye emission, in comparison to direct excitation results.

Figure 17:
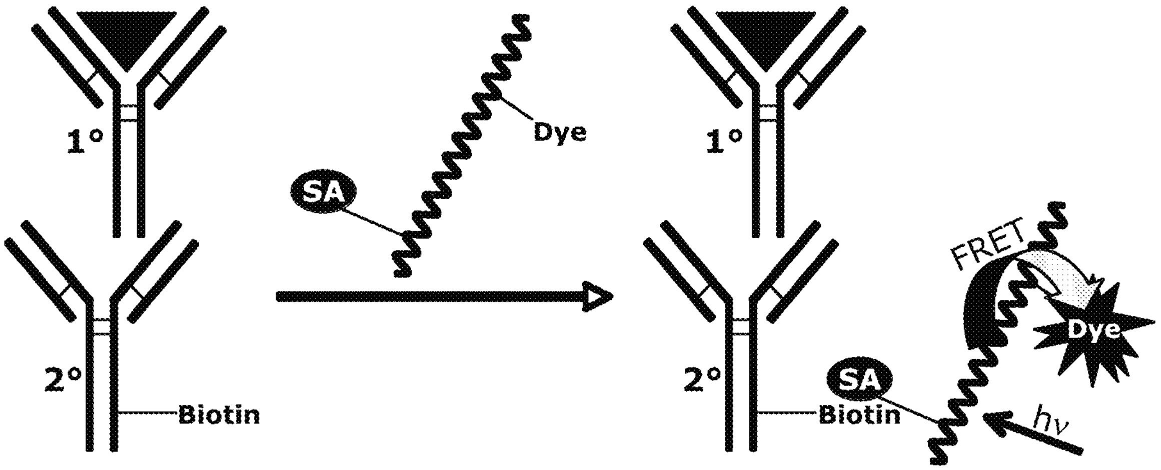
FIG. 17. Schematic of a multichromophore linked to a dye and streptavidin for binding with biotin on a secondary antibody. The secondary antibody is shown as specific for a primary antibody that targets a protein.

FIG. 17 shows an example of a sandwich-type complex of one embodiment of the invention. Here, the multichromophore complex is composed of a multichromophore (shown as wavy line) that is bioconjugated to both a dye and a biomolecule, for example, streptavidin (SA). After an unlabeled 1° antibody binds the target protein, shown as a black triangle, a biotin-labeled 2° antibody binds specifically to the 1° antibody. In a separate step, addition of the multichromophore complex will result in specific binding between the biotin and streptavidin, and excitation of the multichromophore will result in amplified dye emission, as compared to direct excitation of the dye. Signals arising from dye emission will indicate the presence of the target protein.

In a further aspect, the invention provides for the multiplexing of donor energy transfer to multiple acceptors. By using a multichromophore as a donor in a FRET system, benefits also include the ability to multiplex. A single donor can transfer energy to several dyes; thus with a single excitation source, the intensity of multiple dyes can be monitored. This is useful for applications including but not limited to cell imaging (i.e. immunohistochemistry), where the different types of cells can be monitored by protein-antibody recognition events.

In one embodiment, two dye-labeled antibodies can be incubated with a biological material, for example, a cultured cell line. Antibodies are able to recognize cells with a target protein expressed on its surface and specifically bind only to those proteins. By labeling the two antibodies with different dyes, it is possible to monitor for the expression of two different proteins or different cell types simultaneously. Typically, this would require two scans or images, once each with the correct excitation wavelength. As a final step prior to analysis, these two images would have to be overlaid. By using antibodies conjugated to both a dye and a multichromophore, one excitation wavelength can be used for boat dyes, and a single image will include data sets from each of the two antibodies.

Figure 15:
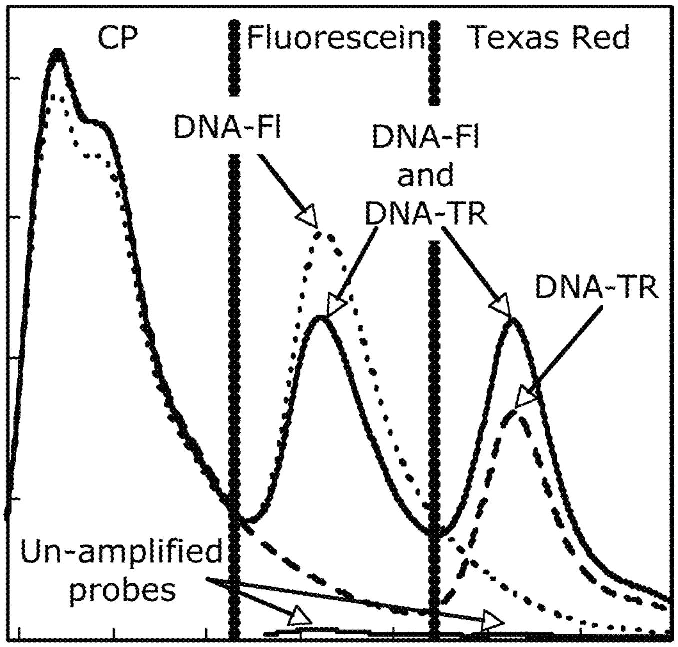
FIG. 15. Plot of single and multiple detection of DNA probes labeled with two dyes.

A relevant example of this embodiment is shown in FIG. 15, which shows the emission spectra for a single donor multichromophore with energy transfer to a fluorescein labeled DNA probe (dotted line), energy transfer to a Texas red-labeled DNA probe (dashed line), and energy transfer to both probes (solid line). Additionally, spectra arising from direct excitation of the two dyes are shown as solid lines towards the bottom of FIG. 15. Significant amplification of the dyes is seen in all three cases. Additionally, intense signals are observed for each dye, regardless of the presence or absence of the other dye, indicating good potential for multiplexing. Parallel results with protein diagnostics are envisioned.

Given the potential for multiplexing analysis, it is envisioned that the multichromophore can be linked to a number of dyes, including, but not limited to, fluorescein, 6-FAM, rhodamine, Texas Red, tetramethylrhodamine, a carboxyrhodamine, carboxyrhodamine 6G, carboxyrhodol, carboxyrhodamine 110, Cascade Blue, Cascade Yellow, coumarin, Cy2®, Cy3®, Cy3.5®, Cy5®, Cy5.5®, Cy-Chrome, phycoerythrin, PerCP (peridinin chlorophyll-a Protein), PerCP-Cy5.5, JOE (6-carboxy-4',5'-dichloro-2',7-dimethoxyfluorescein), NED, ROX (5-(and-6)-carboxy-X-rhodamine), HEX, Lucifer Yellow, Marina Blue, Oregon Green 488, Oregon Green 500, Oregon Green 514, Alexa Fluor® 350, Alexa Fluor®30-Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcoumarin-3-acetic acid, BODIPY® FL, BODIPY® FL-Br.sub.2, BODIPY® 530/550, BODIPY® 558/568, BODIPY® 564/570, BODIPY® 576/589, BODIPY® 581/591, BODIPY® 630/650, BODIPY® 650/665, BODIPY® R6G, BODIPY® TMR, BODIPY® TR, conjugates thereof, and combinations thereof.

It is envisioned that the invention described herein can be used to increase the sensitivity of any of a number of commercially available tests including but not limited to the OraQuick Rapid HIV-1/2 Antibody Test, manufactured by OraSure Technologies, Inc. (Bethlehem, PA), which is a FDA-approved HIV diagnostic test for oral fluid samples. This test can provide screening results with over 99 percent accuracy in as little as 20 minutes.

Multichromophores

Light harvesting multichromophore systems can efficiently transfer energy to nearby luminescent species. Mechanisms for energy transfer include, for example, resonant energy transfer (Forster (or fluorescence) resonance energy transfer, FRET), quantum charge exchange (Dexter energy transfer) and the like. Typically, however, these energy transfer mechanisms are relatively short range, and close proximity of the light harvesting multichromophore system to the signaling chromophore is required for efficient energy transfer. Amplification of the emission can occur when the number of individual chromophores in the light harvesting multichromophore system is large; emission from a fluorophore can be more intense when the incident light (the "pump light") is at a wavelength which is absorbed by the light harvesting multichromophore system and transferred to the fluorophore than when the fluorophore is directly excited by the pump light.

The multichromophores used in the present invention can be charge neutral, cationic or anionic. In some embodiments the multichromophores are polycationic multichromophores.

In embodiments wherein the multichromophore is polycationic they can interact with a biomolecule comprising multiple anionic groups, e.g. polysaccharides, polynucleotides, peptides, proteins, antibodies, etc. In some embodiments, the multichromophore can interact with a target antibody or polynucleotide electrostatically and thereby bring a signaling chromophore on an uncharged sensor polynucleotide into energy-receiving proximity by virtue of antibody-antigen recognition or hybridization between a sensor polynucleotide and a target polynucleotide. Any polycationic multichromophore that can absorb light and preferably emit or transfer energy can be used in the methods described. Exemplary multichromophores that can be used include conjugated polymers (CP), saturated polymers or dendrimers incorporating multiple chromophores in any viable manner, and semiconductor nanocrystals (SCNCs). The CP, saturated polymers and dendrimers can be prepared to incorporate multiple cationic species or can be derivatized to render them polycationic after synthesis; semiconductor nanocrystals can be rendered polycationic by addition of cationic species to their surface. In some embodiments, the polycationic multichromophore is not detected by its ability to transfer energy when excited, and thus methods involving such detection schemes do not require the multichromophore to emit or transfer energy.

In some embodiments, the multichromophore is a CP. In a particular embodiment, the CP is one that comprises "low bandgap repeat units" of a type and in an amount that contribute an absorption to the polymer in the range of about 450 nm to about 1000 nm. The low bandgap repeat units may or may not exhibit such an absorption prior to polymerization, but does introduce that absorption when incorporated into the conjugated polymer. Such absorption characteristics allow the polymer to be excited at wavelengths that produce less background fluorescence in a variety of settings, including in analyzing biological samples and imaging and/or detecting molecules. Shifting the absorbance of the CP to a lower energy and longer wavelength thus allows for more sensitive and robust methods. Additionally, many commercially available instruments incorporate imaging components that operate at such wavelengths at least in part to avoid such issues. For example, thermal cyders that perform real-time detection during amplification reactions and microarray readers are available which operate in this region. Providing polymers that absorb in this region allows for the adaptation of detection methods to such formats, and also allows entirely new methods to be performed.

Incorporation of repeat units that decrease the band gap can produce conjugated polymers with such characteristics. Exemplary optionally substituted species which result in polymers that absorb light at such wavelengths include 2,1,3-benzothiadiazole, benzoselenadiazole, benzotellurodiazole, naphthoselenadiazole, 4,7-di(thien-2-yl)-2,1,3-benzothiadiazole, squaraine dyes, quinoxalines, low bandgap commercial dyes, olefins, and cyano-substituted olefins and isomers thereof. Further details relating to the composition, structure, properties and synthesis of suitable multichromophores can be found in U.S. Provisional Application No. 60/642,901, filed Jan. 10, 2005 and U.S. patent application Ser. No. 11/329,495, filed Jan. 10, 2006, now published as US 2006-0183140 A1, which are both incorporated herein by reference.

Multichromophores can be described as a set of covalently bound chromophoric units or a covalent collection of chromophores. Multichromophores can include, but are not limited to, linear structures, such as, conjugated polymers (CPs) and dendritic structures (Wang, Gaylord, and Bazan, Adv. Mater., 2004, Wang, Hong, and Bazan, Org. Lett., 2005).

Figure 18:
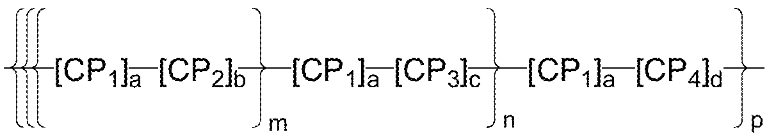
FIG. 18. Schematic of the structure of a conjugated polymer multichromophore of one embodiment of the invention.

FIG. 18 illustrates a general structure for a CP as a linear multichromophore. In one embodiment such a CP could be comprised of those units described in Tables 1 and 2 or Scheme 1 of U.S. patent application Ser. No. 10/666,333: Conformationally Flexible Cationic Conjugated Polymers, by Liu and Bazan, and also include monomers containing one or more unique bioconjugation sites as depicted in FIG. 10 herein. The CP preferably contains at least about 0.01 mol % of the bioconjugation site, and may contain at least about 0.02 mol %, at least about 0.05 mol %, at least about 0.1 mol %, at least about 0.2 mol %, at least about 0.5 mol %, at least about 1 mol %, at least about 2 mol %, at least about 5 mol %, at least about 10 mol %, at least about 20 mol %, or at least about 30 mol %. The CCP may contain up to 100 mol % of the bioconjugation site, and may contain about 99 mol % or less, about: 90 mol % or less, about 80 mol % or less, about 70 mol % or less, about: 60 mol % or less, about 50 mol % or less, or about 40 mol % or less.

In FIG. 18, the units CP1, CP2, CP3, and CP4 are optionally substituted conjugated polymer segments or oligomeric structures, and may be the same or different from one another. CP1, CP2, CP3, and CP4 may be aromatic repeat units, and may be selected from the group consisting of benzene, naphthalene, anthracene, fluorene, thiophene, furan, pyridine, and oxadiazole, each optionally substituted. Additionally, CP3 and CP4 can contain one or more unique bioconjugation sites, linked by a linker L as in FIG. **3*h*. These bioconjugation sites can be, but are nor limited to, maleimide, thiol, succimidylester (NHS ester), amine, azide chemistry, carboxy/EDC (1-Ethyl-3-[3-dimethylaminopropyl]carbodiimide Hydrochloride, Sulfo-SMCC (Sulfosuccinimidyl 4-[N-maleimidomethyl]cyclohexane-1-carboxylate), amine/BMPH (N-[β-Maleimidopropionic acid] hydrazide·TFA), or Sulfo-SBED Sulfosuccinimidyl[2-6-(biotinamido)-2-(p-azidobenzamido)-hexanoamido]-ethyl-1,3'-dithiopropionate, which can serve as a three way linkage among X, Y, and CP in FIG. 13**.

Typical aromatic repeat units are shown in Table 1, and representative polymeric segments and oligomeric structures are shown in Table 2 of U.S. patent application Ser. No. 10/666,333: Conformationally Flexible Cationic Conjugated Polymers by Liu and Bazan.

FIG. 18 contains CP3 and CP4, which can be angled linkers (meta fashion), and can be mono- or polycyclic optionally substituted aryl groups having 5 to 20 atoms. The CP3 and CP4 units may be evenly or randomly distributed along the polymer main chain.

CP1, CP2, CP3 and CP4 are each optionally substituted at one or more positions with one, or more groups selected from —R1-A, —R2-B, —R3-C and —R4-D, which may be attached through bridging functional groups -E- and —F—, with the proviso that the polymer as a whole must be substituted with a plurality of cationic, anionic, or charge neutral water-soluble groups.

R1, R2, R3 and R4 are independently selected from alkyl, alkenyl, alkoxy, alkynyl, and aryl, alkylaryl, arylalkyl, and polyalkylene oxide, each optionally substituted, which may contain one or more heteroatoms, or may be not present. R1, R2, R3 and R4 can be independently selected from C1-22 alkyl, C1-22 alkoxy, C1-22 ester, polyalkylene oxide having from 1 to about 22 carbon atoms, cyclic crown ether having from 1 to about 22 carbon atoms, or not present. Preferably, R1, R2, R3 and R4 may be selected from straight or branched alkyl groups having 1 to about 12 carbon atoms, or alkoxy groups with 1 to about 12 carbon atoms. It is to be understood that more than one functional group may be appended to the rings as indicated in the formulas at one or more positions.

A, B, C and D are independently selected from H, —SiR'R"R'", —$N^+$R'R"R'", a guanidinium group, histidine, polyamine, a pyridinium group, and a sulfonium group. R', R" and R'" are independently selected from the group consisting of hydrogen, $C_{1-12}$ alkyl and $C_{1-12}$ alkoxy and $C_{3-12}$ cycloalkyl. It is preferred that R, R" and R" are lower alkyl or lower alkoxy groups.

E and F are independently selected from not present, —O—, —S—, —C(O)—, —C(O)O—, —C(R)(R')—, —N(R')—, and —Si(R')(R"), wherein R' and R" are as defined above.

X is O, S, Se, —N(R')— or —C(R')(R")—, and Y and Z are independently selected from —C(R)= and —N=, where R, R' and R" are as defined above.

Figure 19:
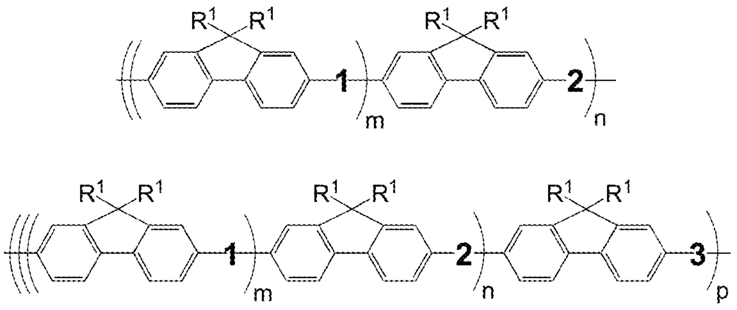
FIG. 19. Schematic of the structure of conjugated polymer multichromophores of additional embodiments of the invention.

FIG. 19 shows a CP composed of a backbone containing fluorene units and aromatic units 1, 2, and 3. The units 1, and 2 may be, but are not limited to, the structures shown in FIG. 20. Unit 3 contains a bioconjugation site. The R1 functionality is noted as a solubilizing group, and can be, but is not limited to, charged alkyl functionalities (CH2)nNMe3Br, or (CH2)bSO3Na) or hydrophilic groups ethylene glycol units, (OCH2CH2)n).

Figure 20:
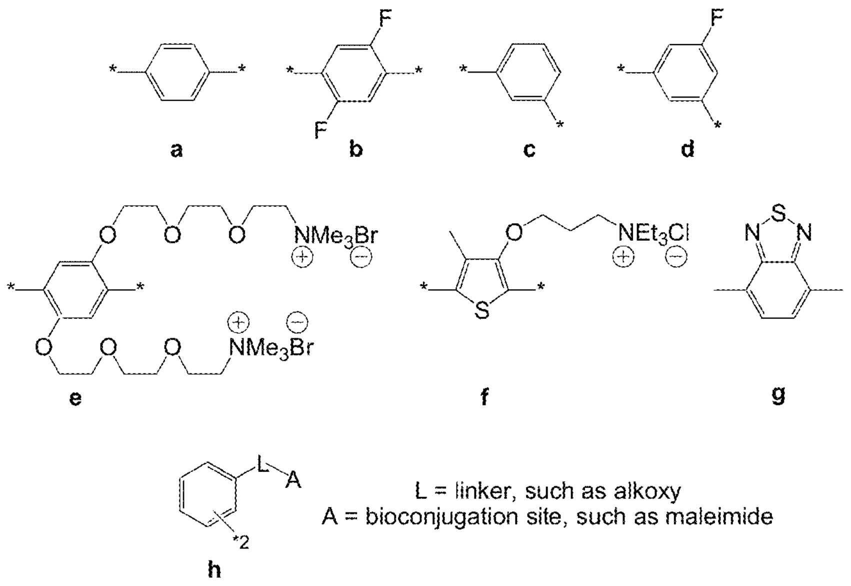
FIG. 20. Schematic of the structure of various aromatic units of embodiments of the invention.

The π-conjugated units 1, 2, and 3 from FIG. 19 include those described in Tables 1 and 2 and Scheme 1 of Liu and Bazan, U.S. patent application Ser. No. 10/666,333: Conformationally flexible Cationic Conjugated Polymers. FIG. 20 shows several specific examples of π-conjugated units that may be contained within a general CP structure, depicted in FIG. 19, with asterisks depicting points of covalent binding to the CP backbone. These units include benzene units connected to the CP backbone in a typical para fashion (a, b, and e) or connected in a meta fashion, which allows for more flexibility within the CP backbone (c and d). These units can be functionalized with moieties that alter the electronic structure (b, d, and e), including donating groups (alkoxy or ethylene glycol units) and withdrawing groups (fluorine) or improve water solubility (e) with hydrophilic ethylene glycol units or charged groups, such as quaternary amines or sulfonates. Also included are units such as thiophenes (f) and benzothiadiazole groups (g), which serve as a means to alter electronic structure. These units can be also be functionalized as described above. The unit h is contains a specific bioconjugation site A, for example, maleimide, which is covalently bound to the π-conjugated segment via a linker L, for example, an alkoxy group, and may be incorporated into the backbone of a CP in a ortho, para, or meta fashion.

Figure 21:
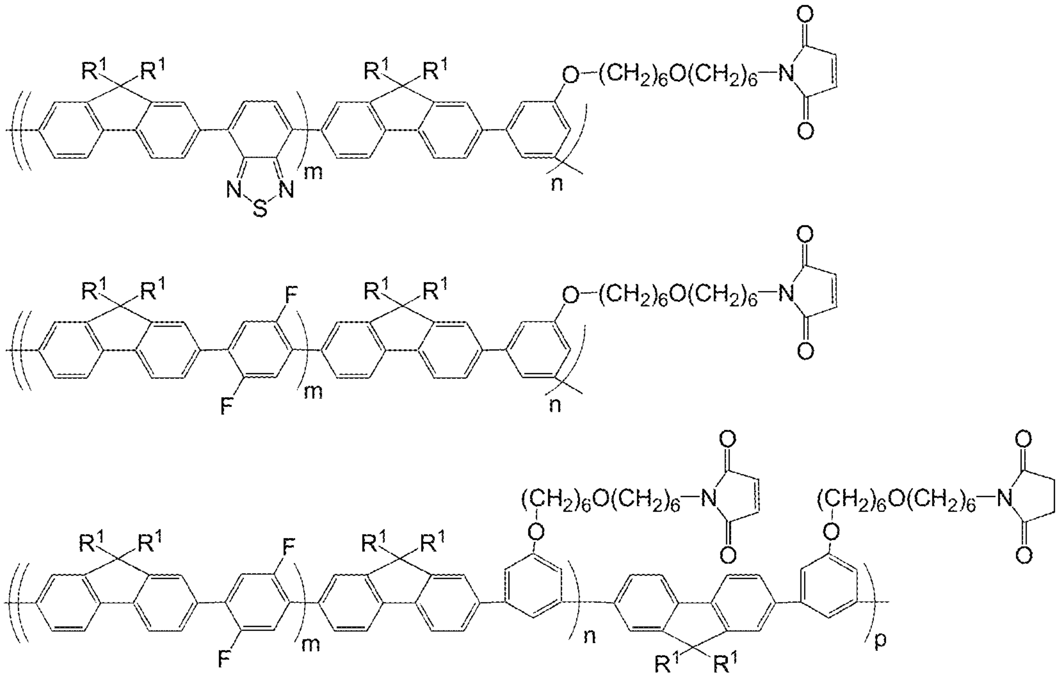
FIG. 21. Schematic of the structure of conjugated polymer multichromophores having maleimide bioconjugation sites.

Several variations of specific polymeric structures include those shown in FIG. 21, which contain a percentage of units with a maleimide or succimidyl ester bioconjugation site linked via ether and alkoxy linkages.

Conjugated polymers useful in the present invention include but are not limited to the following:

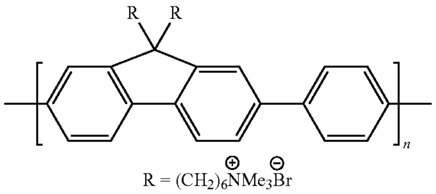

$R = (CH_2)_6N^{\oplus}Me_3Br^{\ominus}$

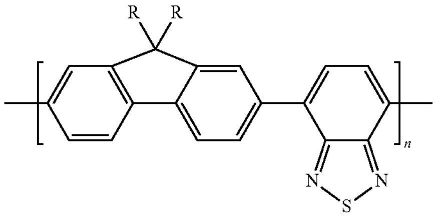

$R = (CH_2)_6N^{\oplus}Me_3Br^{\ominus}$

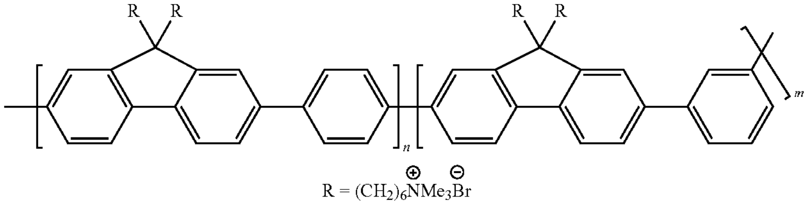

$R = (CH_2)_6N^{\oplus}Me_3Br^{\ominus}$

-continued

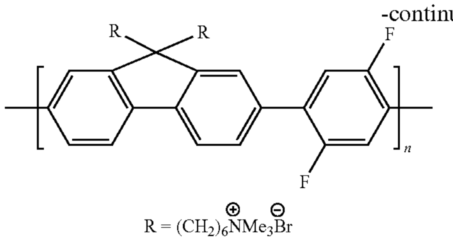

Antigen-Antibody Interactions

The interactions between antigens and antibodies are the same as for other non-covalent protein-protein interactions. In general, four types of binding interactions exist between antigens and antibodies: (i) hydrogen bonds, (ii) dispersion forces, (iii) electrostatic forces between Lewis acids and Lewis bases, and (iv) hydrophobic interactions. Certain physical forces contribute to antigen-antibody binding, for example, the fit or complimentary of epitope shapes with different antibody binding sites. Moreover, other materials and antigens may cross-react with an antibody, thereby competing for available free antibody.

Measurement of the affinity constant and specificity of binding between antigen and antibody is a pivotal element in determining the efficacy of an immunoassay, not only for assessing the best antigen and antibody preparations to use but also for maintaining quality control once the basic immunoassay design is in place.

Antibodies

Antibody molecules belong to a family of plasma proteins called immunoglobulins, whose basic building block, the immunoglobulin fold or domain, is used in various forms in many molecules of the immune system and other biological recognition systems. A typical immunoglobulin has four polypeptide chains, containing an antigen binding region known as a variable region and a non-varying region known as the constant region.

Native antibodies and immunoglobulins are usually heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain.

Depending on the amino acid sequences of the constant domain of their heavy chains, immunoglobulins can be assigned to different classes. There are at least five (5) major classes of immunoglobulins: IgA, IgD, IgE, IgG and IgM, and several of these may be further divided into subclasses (isotypes), e.g. IgG-1, IgG-3 and IgG-4; IgA-1 and IgA-2. The subunit structures and three-dimensional configurations of different classes of immunoglobulins are well known. Further details regarding antibody structure, function, use and preparation are discussed in U.S. Pat. No. 6,998,241, issued Feb. 14, 2006, the entire contents of which are incorporated herein by reference.

Sandwich Assays

Antibody or multiple antibody sandwich assays are well known to those skilled in the art including a disclosed in U.S. Pat. No. 4,486,530, issued Dec. 4, 1984, and references noted therein. The structures described in FIGS. 6, 7, 8 and 14 can be used directly as described or in various sandwich configurations. A sandwich configuration or a sandwich assay refers to the use of successive recognition events to build up layers of various biomolecules and reporting elements to signal the presence of a particular biomolecule, for example a target biomolecule or a target-associated biomolecule. A standard example of this would be the successive use of antibodies. In these assays, a primary antibody binds the target, the secondary antibody binds the primary, a third antibody can bind the secondary and so on. With each successive layer additional reporting groups can be added. Another strategy is using a repetitive addition of alternating layers of two (or more) mutually-recognizable components, or more than two components in a chain-recognition relationship, which comprise one or both of the components in a form of multimeric structure. In such a setup, one or more of the functional group(s) in each of the multimeric structure can be labeled with reporting group(s) and the unoccupied functional group(s) can serve as the recognition site for the other component(s), and this system will subsequently provide a platform for signal amplification. A typical example of this approach is the use of streptavidin-reporter conjugate and biotinylated anti-streptavidin antibody. In such assays, a biotinylated sensor molecule (nucleic acid or antibody) can be used to bind a target biomolecule, which is subsequently recognized by a detection system containing a streptavidin-reporter conjugate and biotinylated anti-streptavidin antibody. The sandwich structure in this case can be built up by successive rounds of biotinylated antibodies and labeled streptavidin complexes interaction to achieve the signal amplification. With an additional conjugation of a multichromophore to either the biotinylated antibody or the streptavidin-reporter complex, it is possible to further increase the signal output. In essence, the integration of a multichromophore in this type of signal amplification system can further amplify signals to a higher level.

The bioconjugated polymer complexes described in FIGS. 6, 7, 8, 14, 16 and 17 can be used to create optically enhanced sandwich assays by directly integrating a light harvesting multichromophore into commonly utilized recognition elements. The benefits of the multichromophore conjugated structures can also be applied directly to the primary target recognition elements without the need for successive recognition elements. For example, a primary antibody can be directly conjugated to multichromophore-dye complex such as shown in FIG. 14. Such a complex can be used to directly probe the presence of a target biomolecule, Polynucleotides Amplified target polynucleotides may be subjected to post amplification treatments. For example, in some cases, it may be desirable to fragment the target polynucleotide prior to hybridization in order to provide segments which are more readily accessible. Fragmentation of the nucleic acids can be carried out by any method producing fragments of a size useful in the assay being performed; suitable physical, chemical and enzymatic methods are known in the art.

An amplification reaction can be performed under conditions which allow the sensor polynucleotide to hybridize to the amplification product during at least part of an amplification cycle. When the assay is performed in this manner, real-time detection of this hybridization event can take place by monitoring for light emission during amplification.

Real time PCR product analysis (and related real time reverse-transcription PCR) provides a well-known technique for real dine PCR monitoring that has been used in a variety of contexts, which can be adapted for use with the methods described herein (see, Laurendeau et al. (1999) "TaqMan PCR-based gene dosage assay for predictive testing in individuals from a cancer family with INK4 locus haploinsufficiency" Clin Chem 45(7):982-6 Laurendeau et al. (1999) "Quantitation of MYC gene expression in sporadic breast tumors with a real-time reverse transcription-PCR assay" Clin Chem 59(12):2759-65; and Kreuter et al. (1999) "LightCycler technology for the quantitation of bcr/ahl fusion transcripts" Cancer Research 59(13):3171-4, all of which are incorporated by reference).

The Sample

In principle, the sample can be any material suspected of containing an aggregant capable of causing aggregation of the aggregation sensor. In some embodiments, the sample can be any source of biological material which comprises polynucleotides that can be obtained from a living organism directly or indirectly, including cells, tissue or fluid, and the deposits left by that organism, including viruses, mycoplasma, and fossils. The sample may comprise an aggregant prepared through synthetic means, in whole or in part. Typically, the sample is obtained as or dispersed in a predominantly aqueous medium. Nonlimiting examples of the sample include blood, urine, semen, milk, sputum, mucus, a buccal swab, a vaginal swab, a rectal swab, an aspirate, a needle biopsy, a section of tissue obtained for example by surgery or autopsy, plasma, serum, spinal fluid, lymph fluid, the external secretions of the skin, respiratory, intestinal, and genitourinary tracts, tears, saliva, rumors, organs, samples of in vitro cell culture constituents (including but not limited to conditioned medium resulting from the growth of cells in cell culture medium, putatively virally infected cells, recombinant cells, and cell components), and a recombinant library comprising polynucleotide sequences.

The sample can be a positive control sample which is known to contain the aggregant or a surrogate therefore. A negative control sample can also be used which, although not expected to contain the aggregant, is suspected of containing it (via contamination of one or more of the reagents) or another component capable of producing a false positive, and is tested in order to confirm the lack of contamination by the target polynucleotide of the reagents used in a given assay, as well as to determine whether a given set of assay conditions produces false positives (a positive signal even in the absence of target polynucleotide in the sample).

The sample can be diluted, dissolved, suspended, extracted or otherwise treated to solubilize and/or purify any target polynucleotide present or to render it accessible to reagents which are used in an amplification scheme or to detection reagents. Where the sample contains cells, the cells can be lysed or permeabilized to release the polynucleotides within the cells. One step permeabilization buffers can be used to lyse cells which allow further steps to be performed directly after lysis, for example a polymerase chain reaction.

Signaling Chromophores

In some embodiments, a signaling chromophore or fluorophore may be employed, for example to receive energy transferred from an excited state of an optically active unit, or to exchange energy with a labeled probe, or in multiple energy transfer schemes. Fluorophores useful in the inventions described herein include any substance which can absorb energy of an appropriate wavelength and emit or transfer energy. For multiplexed assays, a plurality of different fluorophores can be used with detectably different emission spectra. Typical fluorophores include fluorescent dyes, semiconductor nanocrystals, lanthanide chelates, and green fluorescent protein.

Exemplary fluorescent dyes include fluorescein, 6-FAM, rliodamine, Texas Red, tetramethylrhodamine, carboxyrhodamine, carboxyrhodatnine 6G, carboxyrhodol, carboxyrhodamine 110, Cascade Blue, Cascade Yellow, coumarin, Cy2®, Cy3®, Cy3.5®, Cy5®, Cy5.5®, Cy-Chrome, phycoerythrin, PerCP (peridinin chlorophyll-a Protein), PerCP-Cy5.5. JOE (6-carboxy-4',5'-dichloro-2',7'-dimelhoxyfluorescein), NED, ROX (5-(and-6)-carboxy-X-rhodamine), HEX, Lucifer Yellow, Marina Blue, Oregon Green 488, Oregon Green 500. Oregon Green 514, Alexa Fluor® 350, Alexa Fluor® 430, Alexa Fluor® 488, Alexa Fluor® 532, Alexa Fluor® 546, Alexa Fluor® 568, Alexa Fluor® 594, Alexa Fluor® 633, Alexa Fluor® 647, Alexa Fluor® 660, Alexa Fluor® 680, 7-amino-4-methylcournarin-3-acetic acid, BODIPY® FL, BODIPY® FL-$Br_2$, BODIPY® 530/550, BODIPY® 558/568, BODIPY® 564/570, BODIPY® 576/589, BOLYIPY® 581/591, BODIPY® 630/650, BODIPY® 650/665, BODPY® R6G, BODIPY® TMR, BODIPY® TR, conjugates thereof, and combinations thereof. Exemplary lanthanide chelates include europium chelates, terbium chelates and samarium chelates.

A wide variety of fluorescent semiconductor nanocrystals ("SCNCs") are known in the art; methods of producing and utilizing semiconductor nanocrystals are described in: PCT Publ. No. WO 99/26299 published May 27, 1999, inventors Bawendi et al.; U.S. Pat. No. 5,990,479 issued Nov. 23, 1999 to Weiss et al.; and Bwchez et al., Science 281:2013, 1998. Semiconductor nanocrystals can be obtained with very narrow emission bands with well-defined peak emission wavelengths, allowing for a large number of different SCNCs to be used as signaling chromophores in the same assay, optionally in combination with other non-SCNC types of signaling chromophores.

Exemplary polynucleotide-specific dyes include acridine orange, acridine homodimer, actinomycin D, 7-aminoactmomycin D (7-AAD), 9-amino-6-chlor-2-methoxyacridine (ACMA), BOBO™-1 iodide (462/481), BOBO™-3 iodide (570/602), BO-PRO™-1 iodide (462/481), BO-PRO™-3 iodide (575/599), 4',6-diamidino-2-phenylindole, dihydrochloride (DAPI), 4',6-diamidino-2-phenytindole, dihydrochloride (DAPI), 4',6-diamidino-2-phenylindole, dilactate (DAPI, dilactate), dihydroethidium (hydroethidine), dihydroethidium (hydroethidine), dihydroethidium (hydroethidine), ethidium bromide, ethidium diazide chloride, ethidium homodimer-1 (EthD-1), ethidium homodimer-2 (EthD-2), ethidium monoazide bromide (EMA), hexidium iodide, Hoechst 33258, Hoechst 33342, Hoechst 34580, Hoechst 5769121, hydroxystilbamidine, methanesulfonate, JOJO™-1 iodide (529/545), JO-PRO™-1 iodide (530/546), LOLO™-1 iodide (565/579), LO-PRO™-1 iodide (567/580), NeuroTrace™ 435/455, NeuroTrace™ 500/525, NeuroTrace™ 515/535, NeuroTrace™ 530/615, NeuroTrace™ 640/660, OliGreen, PicoGreen® ssDNA, PicoGreen® dsDNA, POPO™-1 iodide (434/456), POPO™-3 iodide (534/570), PO-PRO™-1 iodide (435/455), PO-PRO™-3 iodide (539/567), propidium iodide, RiboGreen®, SlowFade®, SlowFade® Light, SYBR® Green 1, SYBR® Green II, SYBR® Gold, SYBR® 101, SYBR® 102, SYBR® 103, SYBR® DX, TO-PRO®-1, TO-PRO®-3, TO-PRO®-5, TOTO®-1, TOTO®-3, YO-PRO®-1 (oxazole yellow), YO-PRO®-3, YOYO®-1, YOYO®-3, TO, SYTOX® Blue, SYTOX® Green, SYTOX® Orange, SYTO® 9, SYTO® BC, SYTO® 40, SYTO® 41, SYTO® 42, SYTO® 43, SYTO® 44, SYTO® 45, SYTO® Blue, SYTO® 11, SYTO® 12, SYTO® 13, SYTO® 14, SYTO® 15, SYTO® 16, SYTO® 20, SYTO® 21, SYTO® 22, SYTO® 23, SYTO® 24, SYTO® 25, SYTO® Green, SYTO® 80, SYTO® 81, SYTO® 82, SYTO® 83, SYTO® 84, SYTO® 85, SYTO® Orange, SYTO® 17, SYTO® 59, SYTO® 60, SYTO® 61, SYTO® 62, SYTO® 63, SYTO® 64, SYTO® Red, netropsin, distamycin, acridine orange, 3,4-benzopyrene, thiazole orange, TOMEHE, daunomycin, acridine, pentyl-TOTAB, and butyl-TOTIN. Asymmetric cyanine dyes may be used as the polynucleotide-specific dye. Other dyes of interest include those described by Geierstanger, B. H. and Wemmer, D. E., Annu. Rev. Vioshys. Biomol. Struct. 1995, 24, 463-493, by Larson, C. J. and Verdine, G. L., Bioorganic Chemistry: Nucleic Acids, Hecht, S. M., Ed., Oxford University Press: New York, 1996; pp 324-346, and by Glumoff, T. and Goldman, A. Nucleic Acids in Chemistry and Biology, 2nd ed., Blackburn, G. M. and Gait, M. J., Eds., Oxford University Press: Oxford, 1996, pp 375-441. The polynucleotide-specific dye may be an intercalating dye, and may be specific for double-stranded polynucleotides. Other dyes and fluorophores are described at www.probes.com (Molecular Probes, Inc.).

The term "green fluorescent protein" refers to both native *Aequorea* green fluorescent protein and mutated versions that have been identified as exhibiting altered fluorescence characteristics, including altered excitation and emission maxima, as well as excitation and emission spectra of different shapes (Delagrave, S. et al. (1995) Bio/Technology 13:151-154; Heim, R. et al. (1994) Proc. Natl, Acad. Sci. USA 91:12501-12504; Heim, R. et al, (1995) Nature 373: 663-664). Delgrave et al. isolated mutants of cloned *Aequorea victoria* GEP that had red-shifted excitation spectra. Bio/Technology 13:151-154 (1995), Heim, R. et al. reported a mutant (Tyr66 to His) having a blue fluorescence (Proc. Natl. Acad. Sci, (1994) USA 91:12501-12504).

The Substrate

In some embodiments, an assay component can be located upon a substrate. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), polyethylene-co-vinyl acetate), polysiloxanes, polymeric silica, latexes, dextran polymers, epoxies, polycarbonates, or combinations thereof. Conducting polymers and photoconductive materials can be used.

Substrates can be planar crystalline substrates such as silica based substrates (e.g. glass, quartz, or the like), or crystalline substrates used in, e.g., the semiconductor and microprocessor industries, such as silicon, gallium arsenide, indium doped GaN and the like, and includes semiconductor nanocrystals.

The substrate can take the form of a photodiode, an optoelectronic sensor such as an optoelectronic semiconductor chip or optoelectronic thin-film semiconductor, or a biochip. The location(s) of probe(s) on the substrate can be addressable; this can be done in highly dense formats, and the location(s) can be microaddressable or nanoaddressable.

Silica aerogels can also be used as substrates, and can be prepared by methods known in the art. Aerogel substrates may be used as free standing substrates or as a surface coating for another substrate material.

The substrate can take any form and typically is a plate, slide, bead, pellet, disk, particle, microparticle, nanoparticle, strand, precipitate, optionally porous gel, sheets, tube, sphere, container, capillary, pad, slice, film, chip, multiwell plate or dish, optical fiber, etc. The substrate can be any form that is rigid or semi-rigid. The substrate may contain raised or depressed regions on which an assay component is located. The surface of the substrate can be etched using well known techniques to provide for desired surface features, for example trenches, v-grooves, mesa structures, or the like.

Surfaces on the substrate can be composed of the same material as the substrate or can be made from a different material, and can be coupled to the substrate by chemical or physical means. Such coupled surfaces may be composed of any of a wide variety of materials, for example, polymers, plastics, resins, polysaccharides, silica or silica-based materials, carbon, metals, inorganic glasses, membranes, or any of the above-listed substrate materials. The surface can be optically transparent and can have surface Si—OH functionalities, such as those found on silica surfaces.

The substrate and/or its optional surface can be chosen to provide appropriate characteristics for the synthetic and/or detection methods used. The substrate and/or surface can be transparent to allow the exposure of the substrate by light applied from multiple directions. The substrate and/or surface may be provided with reflective "mirror" structures to increase the recovery of light.

The substrate and/or its surface is generally resistant to, or is treated to resist, the conditions to which it is to be exposed in use, and can be optionally treated to remove any resistant material after exposure to such conditions.

Polynucleotide probes can be fabricated on or attached to the substrate by any suitable method, for example the methods described in U.S. Pat. No. 5,143,854, PCT Publ. No. WO 92/10092, U.S. patent application Ser. No. 07/624,120, filed Dec. 6, 1990 (now abandoned), Fodor et al., Science, 251: 767-777 (1991), and PCT Publ. No. WO 90/15070), Techniques for the synthesis of these arrays using mechanical synthesis strategies are described in, e.g., PCT Publication No. WO 93/09668 and U.S. Pat. No. 5,384,261.

Still further techniques include bead based techniques such as those described in PCT Appl, No. PCT/US93/04145 and pin based methods such as those described in U.S. Pat. No. 5,288,514.

Additional flow channel or spotting methods applicable to attachment of sensor polynucleotides to the substrate are described in U.S. patent application Ser. No. 07/980,523, filed Nov. 20, 1992, and U.S. Pat. No. 5,384,261. Reagents are delivered to the substrate by either (1) flowing within a channel defined on predefined regions or (2) "spotting" on predefined regions. A protective coating such as a hydrophilic or hydrophobic coating (depending upon the nature of the solvent) can be used over portions of the substrate to be protected, sometimes in combination with materials that facilitate wetting by the reactant solution in other regions. In this manner, the flowing solutions are further prevented from passing outside of their designated flow paths.

Typical dispensers include a micropipette optionally robotically controlled, an ink-jet printer, a series of tubes, a manifold, an array of pipettes, or the like so that various reagents can be delivered to the reaction regions sequentially or simultaneously.

The substrate or a region thereof may be encoded so that the identity of the sensor located in the substrate or region being queried may be determined. Any suitable coding scheme can be used, for example optical codes, RFID tags, magnetic codes, physical codes, fluorescent codes, and combinations of codes.

Excitation and Detection

Any instrument that provides a wavelength that can excite the aggregation sensor and is shorter than the emission wavelength(s) to be detected can be used for excitation. Commercially available devices can provide suitable excitation wavelengths as well as suitable detection components.

Exemplary excitation sources include a broadband UV light source such as a deuterium lamp with an appropriate filter, the output of a white light source such as a xenon lamp or a deuterium lamp after passing through a monochromator to extract out the desired wavelengths, a continuous wave (cw) gas laser, a solid state diode laser, or any of the pulsed lasers. Emitted light can be detected through any suitable device or technique; many suitable approaches are known in the art. For example, a fluorimeter or spectrophotometer may be used to detect whether the test sample emits light of a wavelength characteristic of the signaling chromophore upon excitation of the multichromophore.

Compositions of Matter

Also provided are compositions of matter of any of the molecules described herein in any of various forms. The multichromophores and complexes including multichromophores as described herein may be provided in purified and/or isolated form. The multichromophores and complexes including multichromophores may be provided in crystalline form.

The multichromophores and complexes including multichromophores may be provided in solution, which may be a predominantly aqueous solution, which may comprise one or more of the additional solution components described herein, including without limitation additional solvents, buffers, biomolecules, polynucleotides, fluorophores, etc. The multichromophores and complexes including multichromophores can be present in solution at a concentration at which a first emission from the first optically active units can be detected in the absence of biomolecule target or a biomolecule associated therewith. The solution may comprise additional components as described herein, including labeled probes such as fluorescently labeled antibodies or polynucleotides, specific for a species of a class of biomolecule target or a biomolecule associated therewith for the multichromophores and complexes including multichromophores.

The multichromophores and complexes including multichromophores may be provided in the form of a film. The compositions of matter may be claimed by any property described herein, including by proposed structure, by method of synthesis, by absorption and/or emission spectrum, by elemental analysis, by NMR spectra, or by any other property or characteristic.

In some embodiments expression of a gene is detected in a sample. In a further embodiment, a measured result of detecting a biomolecule target or a biomolecule associated therewith can be used to diagnose a disease state of a patient. In yet another embodiment the detection method of the invention can further include a method of diagnosing a disease state. In a related embodiment, the method of diagnosing a disease can include reviewing or analyzing data relating to the presence of a biomolecule target or a biomolecule associated therewith and providing a conclusion to a patient, a health care provider or a health care manager, the conclusion being based on the review or analysis of data regarding a disease diagnosis. Reviewing or analyzing such data can be facilitated using a computer or other digital device and a network as described herein. It is envisioned that information relating to such data can be transmitted over the network.

In practicing the methods of the present invention, many conventional techniques in molecular biology are optionally utilized. These techniques are well known and are explained in, for example, Ausubel et al. (Eds.) Current Protocols in Molecular Biology, Volumes I, II, and III, (1997), Ausubel et al. (Eds.), Short Protocols in Molecular Biology: A Compendium of Methods from Current Protocols in Molecular Biology, 5$^{th}$ Ed., John Wiley & Sons, Inc. (2002), Sambrook et al., Molecular Cloning: A Laboratory Manual, 3rd Ed., Cold Spring Harbor Laboratory Press (2000), and Innis et al. (Eds.) PCR Protocols: A Guide to Methods and Applications, Elsevier Science & Technology Books (1990), all of which are incorporated herein by reference.

Figure 22:
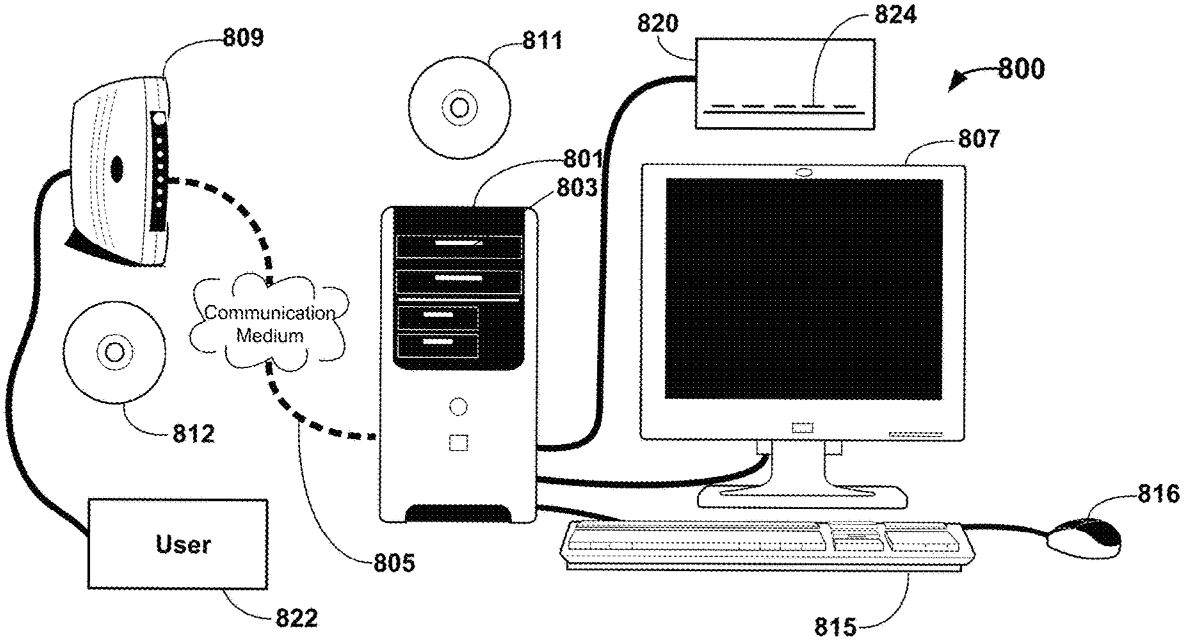
FIG. 22. Block diagram showing a representative example logic device.

FIG. 22 is a block diagram showing a representative example logic device through which reviewing or analyzing data relating to the present invention can be achieved. Such data can be in relation to a disease, disorder or condition in a subject. FIG. 22 shows a computer system (or digital device) 800 connected to an apparatus 820 for use with the multichromophore or multichromophore complexes 824 to, for example, produce a result. The computer system 800 may be understood as a logical apparatus that can read instructions from media 811 and/or network port 805, which can optionally be connected to server 809 having fixed media 812. The system shown in FIG. 22 includes CPU 801, disk drives 803, optional input devices such as keyboard 815 and/or mouse 816 and optional monitor 807. Data communication can be achieved through the indicated communication medium to a server 809 at a local or a remote location. The communication medium can include any means of transmitting and/or receiving data. For example, the communication medium can be a network connection, a wireless connection or an internet connection. It is envisioned that data relating to the present invention can be transmitted over such networks or connections.

In one embodiment, a computer-readable medium includes a medium suitable for transmission of a result of an analysis of a biological sample. The medium can include a result regarding a disease condition or state of a subject, wherein such a result is derived using the methods described herein.

Kits

Kits comprising reagents useful for performing described methods are also provided.

In some embodiments, a kit comprises reagents including multichromophore or multichromophore complexes, bioconjugates, for example, antibodies, and other components as described herein.

The kit may optionally contain one or more of the following: one or more labels that can be incorporated into multichromophore or multichromophore complexes, and one or more substrates which may or may not contain an array, etc.

The components of a kit can be retained by a housing. Instructions for using the kit to perform a described method can be provided with the housing, and can be provided in any fixed medium. The instructions may be located inside the housing or outside the housing, and may be printed on the interior or exterior of any surface forming the housing that renders the instructions legible. A kit may be in multiplex form for detection of one or more different target biomolecules or biomolecules associated therewith.

Figure 23:
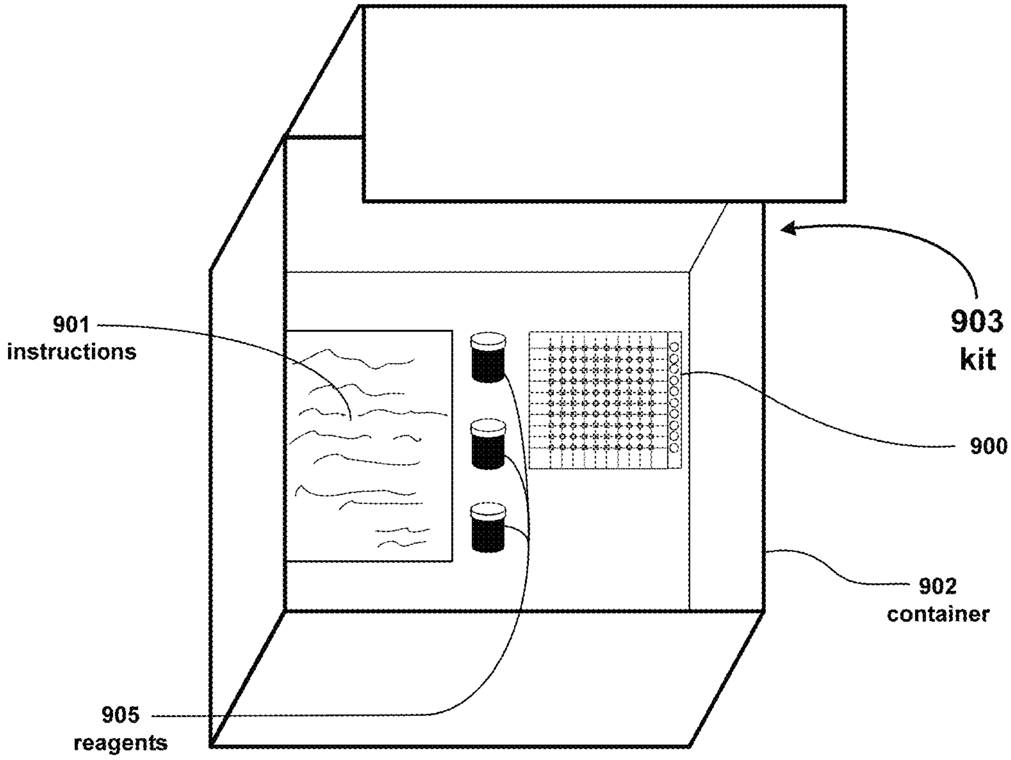
FIG. 23. Block diagram showing a representative example of a kit.

As described herein and shown in FIG. 23, in certain embodiments a kit 903 can include a container or housing 902 for housing various components. As shown in FIG. 23, and described herein, in one embodiment a kit 903 comprising one or more multichromophore or multichromophore complexes reagents 905, and optionally a substrate 900 is provided. As shown in FIG. 23, and described herein, the kit 903 can optionally include instructions 901. Other embodiments of the kit 903 are envisioned wherein the components include various additional features described herein.

EXAMPLES

Example 1

General Protocol for the Sandwich ELISA Method with Polymer-Dye Conjugated Antibody:

1. Bind the unlabeled antibody to the bottom of each well by adding approximately 50 μL of antibody solution to each well (20 μg/mL: in PBS) in a 96 wells polyvinylchloride (PVC) microliter plate. PVC will bind approximately 100 ng/well. (300 ng/cm2). The amount of antibody used will depend on the individual assay.
2. Incubate the plate overnight at 4° C. to allow complete binding.
3. Wash the wells twice with PBS.
4. The remaining sites for protein binding on the microtiter plate must be saturated by incubating with blocking buffer. Fill the wells to the top with 3% BSA/PBS with 0.02% sodium azide. Incubate for 2 hrs. to overnight in a humid atmosphere at room temperature.
5. Wash wells twice with PBS.
6. Add 50 μL of the antigen (or sample) solution to the wells (the antigen solution should be titrated). All dilutions should be done in the blocking buffer (3% BSA/PBS). Incubate for at least 2 hrs. at room temperature in a humid atmosphere.
7. Wash the plate four times with PBS.
8. Add access amount of the either polymer-dye-second antibody conjugates (Example A or C) or biotin-labeled antibody.
9. Incubate for 2 hrs, or more at room temperature in a humid atmosphere.
10. Wash with several changes of PBS,
11. When the biotin-labeled antibody is used in Step 8, add streptavidin-polymer-dye conjugate (Example B or D, in PBS containing 1 M NaCl) and incubate for 2 hrs. or more at room temperature in a humid atmosphere
12. Measure optical densities at target wavelengths on an ELISA plate reader.

For quantitative results, compare signal of unknown samples against those of a standard curve. Standards must be run with each assay to ensure accuracy.

In the ELISA assays, the primary antibody molecules are bound on the side and bottom of the wells in a microliter plate. When the sample containing the target molecules is added into the well, the immobilized primary antibody will only capture those targets and the rest of the components in sample will be washed away. Comparing to the commonly used fluorescence-labeled antibody, the described polymer-dye-secondary antibody conjugates may emit a much stronger signal (10-100 fold) than the regular setup due to their higher light harvesting capability and their within-the-same-molecule design for better energy transfer efficiency. These advantages can also be translated into an assay with higher sensitivity. When further comparing the polymer-dye-secondary antibody conjugates with the other secondary antibody equipped with a signal amplification functionality (e.g., horseradish peroxidase labeled antibody), the polymer-dye-secondary antibody conjugates can provide a one-step process (without additional enzymatic substrate) to achieve the purpose of signal amplification. The cost effectiveness (in both of time and material) of the described conjugates is also anticipated to have a better market acceptance.

Example 2

General Protocol for Microarray Labeling with Polymer-Dye Conjugated Antibody:

1. Prepare total RNA or mRNA.
2. Use T7-oligo(dT) primer to perform one-cycle or two-cycle cDNA synthesis.
3. Cleanup of double stranded cDNA.
4. Use IVT (in vitro transcription) amplification kit to incorporate biotin-labeled ribonucleotide into cRNA.
5. Fragmentation of cRNA.
6. Hybridize cRNA fragments on chip.
7. Wash off residual cRNA and stain the chip with strep in-polymer-dye conjugate (Example B or D)
8. Wash off residual reagents on chip.
9. Scan microarray.

In the regular practice of microarray methodology, an integration of biotin-labeled nucleotides into the cRNA sequences is the means of sequestering the septavidin phycoerythrin conjugate and biotinylated anti-streptavidin antibody for amplified signal reporting. Due to the manufacture complexity of streptavidin phycoerythrin conjugate, the batch-to-batch variation is significant. Therefore, the streptavidin-polymer-dye conjugate can be a very good alternative to replace streptavidin phycoerythrin conjugate. Furthermore, prior publications have demonstrated that MULTICHROMOPHORES can amplify the fluorescence signals up to 75-fold through its light harvesting and energy transfer functionalities. It is reasonable to anticipate that the streptavidin-polymer-dye conjugate may perform equivalently or better than phycoerythrin.

While preferred embodiments of the present invention have been shown and described herein, it will be obvious to those skilled in the an that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Example 3

Synthesis of Cationic Conjugated Polymer with an Amine Functional Group, CA001:

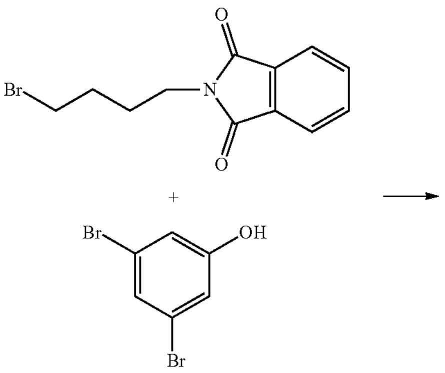

-continued

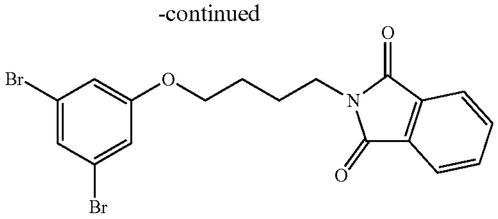

1-(4'-Phthalimidobutoxy)-3,5-dibromobenzene: 3,5-dibromophenol (970 mg, 3.85 mmol) was recrystallized from Hexanes. After removal of solvent, N-(4-bromobutyl) phthalimide (1.38 g, 4.89 mmol), $K_2CO_3$ (1.88 g, 13.6 mmol), 18-crown-6 (53 mg, 0.20 mmol), and acetone (20 mL) were added. This was refluxed for 1 hour, and then poured into 100 mL of water. The aqueous layer was extracted with dichloromethane (4×30 mL). The organic layers were combined, washed with water, saturated $NaHCO_3$, and brine, then dried over $MgSO_4$ and filtered. Removal of solvent yielded a white solid, which) was purified by column chromatography (4:1 hexanes:$CH_2Cl_2$) followed by recrystallization in hexanes to yield colorless needles (650 mg, 87%). $^1H$ NMR ($CDCl_3$): 7.860 (m, 2H); 7.733 (m, 2H); 7.220 (t, J=1.6 Hz, 1H); 6.964 (d, J=2.0 Hz, 2H); 3.962 (t, J=6.0 Hz, 2H); 3.770 (t, J=6.6 Hz, 2H); 1.846 (m, 4H).

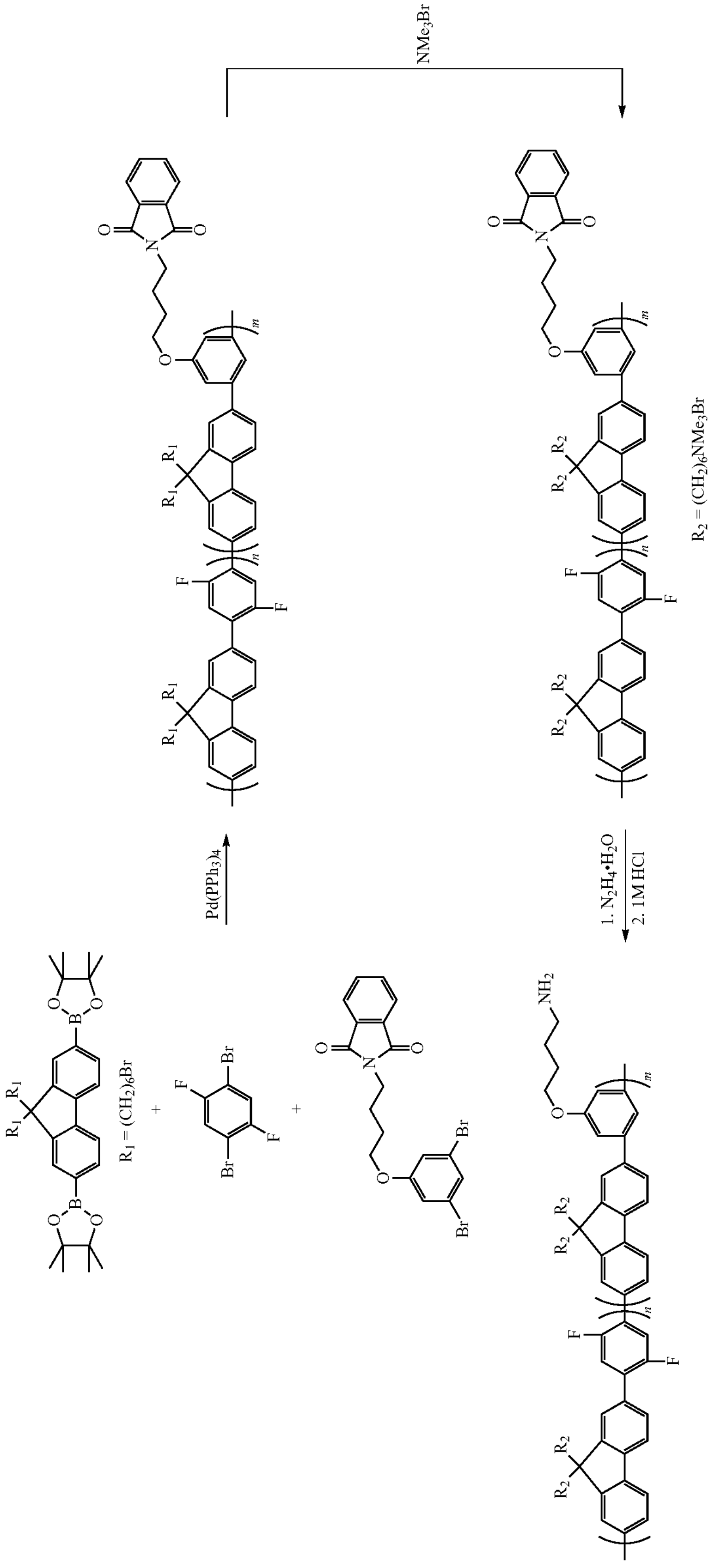
$R_1 = (CH_2)_6Br$
$Pd(PPh_3)_4$
$NMe_3Br$
$R_2 = (CH_2)_6NMe_3Br$
1. $N_2H_4 \cdot H_2O$
2. 1M HCl Poly[2,7-{9,9-bis(6'-bromohexyl)}fluorene-co-alt-1,4-{2,5-difluoro}phenylene)-co-(2,7-{9,9-bis(6'-bromohexyl)}fluorene-co-alt-3,5-1-(4'-phthalimidobutoxy)phenylene)]:
A solution of 2,7-(4,4,5,5-tetramethyl-1,3,2-dioxaborolan-2-yl)-9,9-bis(6'-bromohexyl)fluorene (1.001 g, 1.34 mmol), 1,4-dibromo-2,5-difluorobenzene (346.6 mg, 1.274 mmol), 1-(4'-phthalimidobutoxy)-3,5-dibromobenzene (30.8 mg, 0.068 mmol), potassium carbonate (2.15 g, 15.5 mmol), and tetrakis(triphenylphosphine)palladium (0) (37.2 mg, 0.032 mmol)) in THF (45 mL) and water (15 mL) in a 100 mL round-bottomed flask equipped with a water jacketed reflux condenser was degassed via four freeze-pump-thaw cycles, with argon being introduced after the third and fourth round of degassing. The solution was then heated to reflux for 48 hours under an argon atmosphere. After cooling, the solution was added dropwise to 40 mL of stirring methanol to precipitate the polymer, which was collected by centrifugation. This was followed by decanting and washing with methanol (twice) to remove low molecular weight fractions, yielding a pale yellow, fluffy powder (500 mg, 62%). 1H NMR (CD2Cl2): 7.912-7.419 (m, 8H); 3.322 (t, J=7.4 Hz, 4H); 2.120 (br s, 4H); 1.693 (t, J=7.0 Hz, 4H); 1.237 (br s, 4H); 1.153 (br s, 4H); 0.788 (br s, 4H). Mn 17K, PDI 2.1.

Poly[(2,7-{9,9-bis(6'-(N,N,N-trimethylammoniumbromide)hexyl)}fluorene-co-alt-1,4-{2,5-difluro}pheneylene)-co-(2,7-{9,9-bis(6'-(N,N,N-trimethylammoniumbromide)hexyl)}fluorene-co-alt-3,5-1-(4'-phthalimidobutoxy)phenylene)]: Trimethylamine (1 mL) was condensed into a solution of poly[(2,7-{9,9-bis(6'-bromohexyl)}fluorene-co-alt-1,4-{2,5-difluoro}phenylene)-co-(2,7-{9,9-bis(6'-bromohexyl)}fluorene-co-alt-3,5-1-(4'-phthalimidobutoxy)phenylene)] (130 mg, 0.215 mmol) in THF (10 mL) under reduced pressure. This solution was stirred for 24 h, at which point the polymer precipitated from solution. Methanol was added (50 mL) to solubilize the polymer, then another 1 mL of trimethylamine was condensed into the reaction flask under reduced pressure. This was stirred an additional 24 hours, then all solvents and excess trimethylamine removed under reduced pressure to give a pale yellow film (140 mg, 90%). 1H NMR (D2O): 7.871-7.423 (m, 8H); 3.148 (m, 4H); 2.970 (br s, 18H); 2.116 (br s, 4H); 1.525 (br s, 4H); 1.119 (br s, 8H); 0.681 (br s, 4H).

CA001, poly[(2,7-{9,9-bis(6'-(N,N,N-trimethylammoniumbromide)hexyl)}fluorene-co-alt-1,4-{2,5-difluoro}phenylene)-co-(2,7-{9,9-bis(6'-(N,N,N-trimethylammoniumbromide)hexyl)}fluorene-co-alt-3,5-1-(4'-aminobutoxy)phenylene)]: A solution of hydrazine monohydrate (73.1 mg, 1.46 mmol), poly[(2,7-{9,9-bis(6'-(N,N,N-trimethylammoniumbromide)hexyl)}fluorene-co-alt-1,4-{2,5-difluoro}phenylene)-co-(2,7-{9,9-bis(6'-(N,N,N-trimethylammoniumbromide)hexyl)}fluorene-co-alt-3,5-1-(4'-phthalimidobutoxy)phenylene)] (100 mg, 0.137 mmol) in methanol (10 mL) were refluxed for 5 hours. After cooling to room temperature, 0.9 mL 1M HCl were then added to the solution, which was then refluxed for an additional 2 hours. The resulting solution was dialyzed against 50% methanol in water, then evaporated to dryness.

Figure 24:
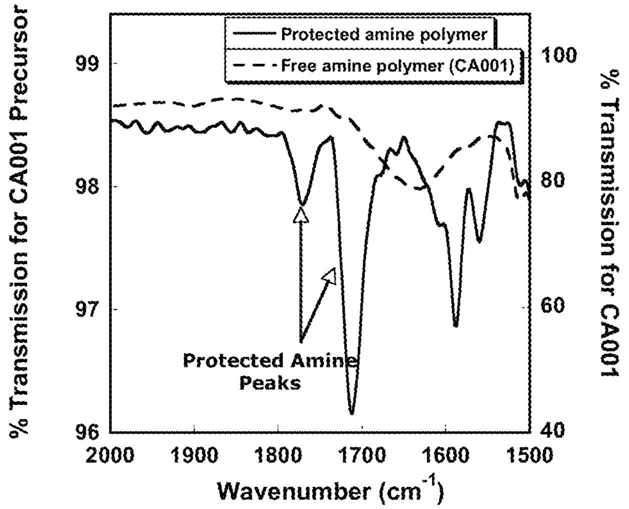
FIG. 24. Plot of an infrared (IR) spectroscopic analysis of an embodiment of the invention.

A method was determined for evaluating the incorporation of the functionalized monomers into the final polymer structures. The amine functional groups were protected as phthalimide during the polymerization reaction to prevent catalyst contamination. This protecting group has a unique signature in infrared (IR) spectroscopy, shown as a solid line in FIG. 24. The peaks indicated correspond to unique C=O peaks only present for the phthalimide protecting group. Post deprotection of the phthalimide group (yielding a free amine) gives a CA001 IR signature that lacks the phthalimide's signature C=O peaks (dashed line, FIG. 24), and indicates an active amine available for conjugation.

Figure 25:
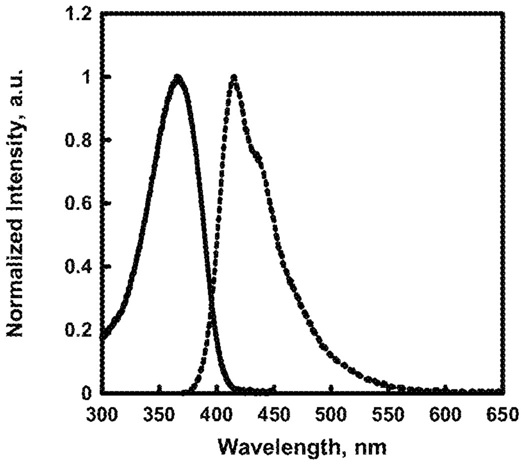
FIG. 25. Plot of the optical spectra of an embodiment of the invention.

The optical spectra of CA001 are shown in FIG. 25, where the solid line indicates the absorption and the dotted line indicates the emission spectra.

Example 4

Synthesis of Cationic Conjugated Polymer—FAM Conjugate, CA001-FAM:

The deprotected polymer CA001 (having a free amine) was reacted with a succinimidyl ester FAM, 5(6)FAM-SE (Invitrogen, #C1311), adapted from protocols available at www.invitrogen.com (last visited Oct. 4, 2007). As a negative control, the same polymer was incubated with fluorescein (no reactive group) under the same reaction conditions. The protocol for this procedure follows.

Conjugation of NHS-PAM to CA001
Purpose:
  To biotinylate CA001 with NHS-FAM and demonstrate FRET to covalently-bound dye.
Materials:
  Fluorometer, with UV-transparent cuvettes
  UV-VIS instrument
Purified CA001
  NHS-FAM (Invitrogen #C-1311)
  0.5 M NEt3 (1:14 dilution of stock (7.2M) NEt3)
  MC30 filters
Procedure:
  1. Set up reactions using a 10-fold XS of NH-FAM to amine-polymer. Use 50 ug polymer and 8.0 ug NHS-FAM per 10 uL rxn:

| Sample | uL Rxn | 90% M1T | CA001 | 0.25M NEt3 | NHS-FAM, 8.0 mg/mL DMSO | Fluorescein, 8.0 mg/mL DMSO |
|---|---|---|---|---|---|---|
| CA001 + NHS-FAM: | 10 | (8-x) uL | x uL | 1.0 uL | 1.0 uL | — |
| CA001 − NHS-FAM: | 10 | | | 1.0 | — | 1.0 uL |

Figure 26:
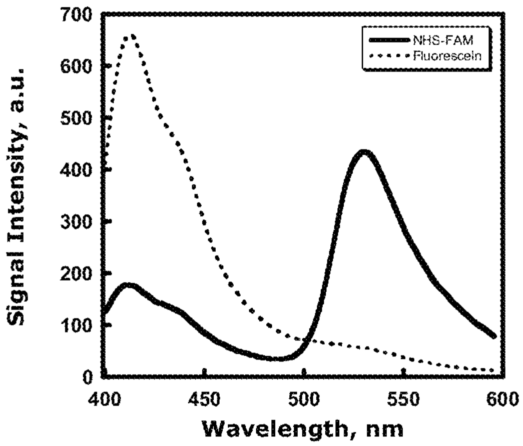
FIG. 26. Plot of the fluorescence spectra of an embodiment of the invention.

2. When all but dye have been combined, dissolve 1-2 mgs of dye in DMSO at 130 uL anhydrous DMSO/mg dye. Use NHS-reagents without delay after dissolving.
  3. Incubate 25 C on heat block for 30 min.
  4. Dilute in 90M1T (10 uL in 400 ul)
  5. Desalt by MC30, 2X
  6. Assay for concentration by UV/Vis Resulting fluorescence spectra for each reaction product are shown in FIG. 26. The fluorescence arising from the positive control is shown as a solid line. When the polymer is excited, FRET to the acceptor dye (now covalently bound to the polymer) occurs, resulting in intense fluorescein emission. The fluorescence arising from the negative control is shown as a dotted line. Because the fluorescein for the negative control cannot bind the polymer, when the polymer is excited, FRET does not occur and only polymer emission is observed. These data indicate that the amine on CA001 is available for conjugation.

Example 5

Synthesis of a Biotinylated Conjugated Polymer, Biotinyl-CA001:

Materials:
NanoDrop fluorometer
Perkin-Elmer fluorometer, model PE-LS55
UV-transparent plastic 1-ml cuvettes
pipeters+tips
biotinyl-CA001 (BCA)
CA001 (CA)
biotinyl-fluorescein (BEL)

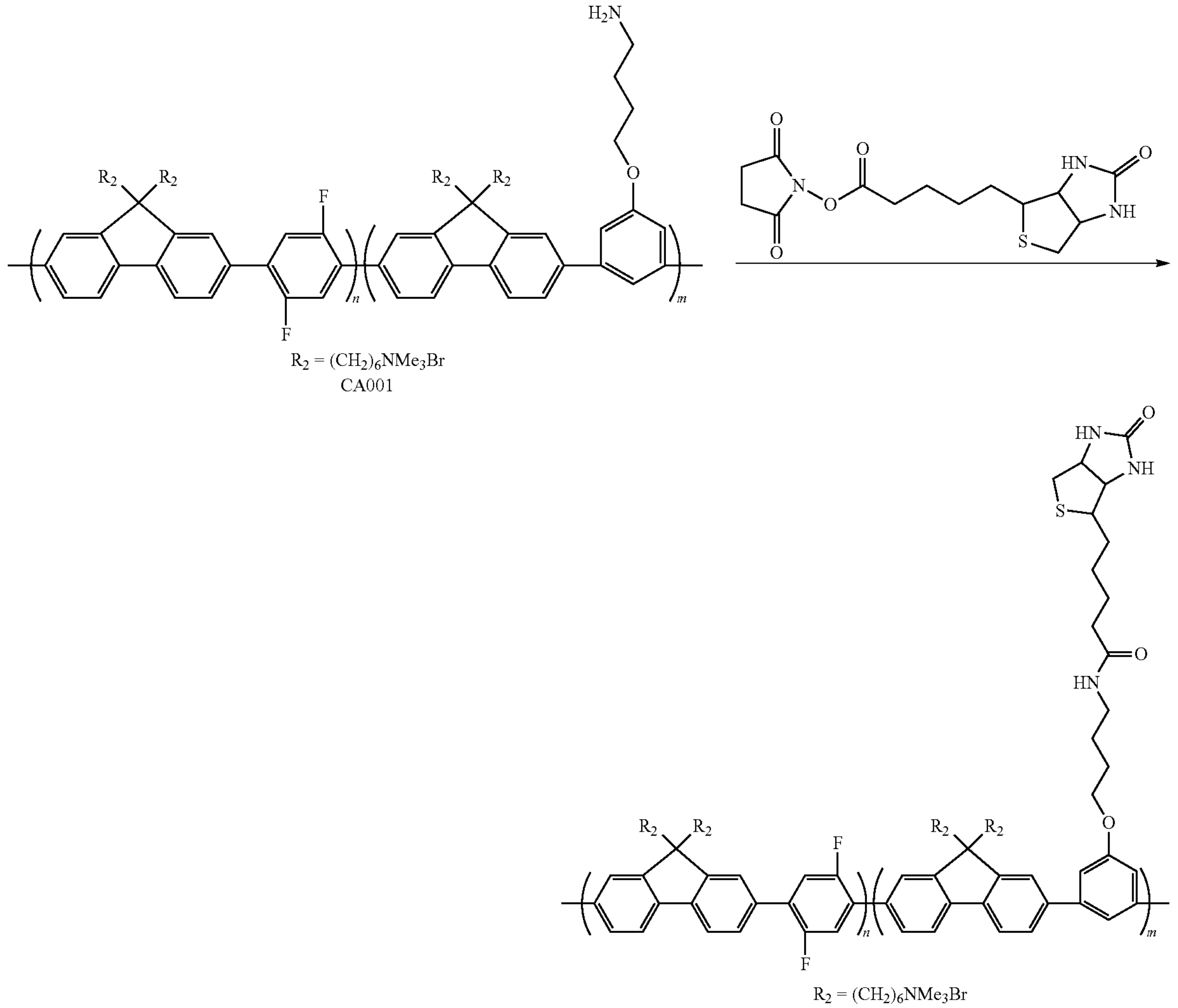

$R_2 = (CH_2)_6NMe_3Br$
CA001

$R_2 = (CH_2)_6NMe_3Br$
Biotinyl-CA001

The amine functionality on CA001 was converted to a biotin functionality using an NHS-biotin linker available from Pierce (#20217). The protocol for this procedure was modified from the Pierce protocol, found on the Pierce website, www.piercenet.com (last visited Sep. 23, 2007). The protocol for this procedure analogously follows that noted in Example 12.

Example 6

Procedure for the Amplification of Signal by Biotinyl-CA001, Avidin DN, and Biotinyl-Fluorescein:

Purpose:
To demonstrate fluorescent signal amplification via FRET, using biotinyl-CA001, Avidin DN, and biotinyl-fluorescein Avidin DN (ADN)
TBS Procedure:
1. In an eppendorf tube, combine reagents as listed in table below. Be sure add ADN last and to Mix together other reagents prior to addition of ADN. Dilute combinations 100-fold prior to measurement on a fluorometer, either 1 uL in 100 uL for the NanoDrop, 10 ul in 1 mL cuvette for a benchtop fluorometer.
2. Directly excite fluorescein at 488 nm as well as indirectly via FRET by exciting the polymer at 380 nm.
3. Collect data on peak heights at relevant wavelengths. Subtract background from peak heights, including these sources
3a) Buffer alone control 3b) Polymer peak tail (~5%) from FRET to fluorescein peaks

| | TBS | B-FL 5 uM | CA 5 uM | BCA 5 uM | ADN 5 uM | Exc. (nm) | 415 nm pk. ht. | 533 nm pk. ht. | 533 nm pk. ht. |
|---|---|---|---|---|---|---|---|---|---|
| TBS only | 20 uL | | | | | 488 | — | | |
| | | | | | | 380 | | | |
| BFL only | 20 uL | 1 uL | | | | 488 | — | | |
| CA only | 20 uL | | 1 uL | | | 380 | | | |
| BFL + CA + ADN, 1:1:1 | 20 uL | 1 uL | 1 uL | | 1 uL | 488 | | | |
| | | | | | | 380 | | | |
| BFL + BCA + ADN, 1:1:1 | 20 uL | 1 uL | | 1 uL | 1 uL | 488 | | | |
| | | | | | | 380 | | | |
| BFL + CA + ADN, 1:2:1 | 20 uL | 1 uL | 2 uL | | 1 uL | 488 | | | |
| | | | | | | 380 | | | |
| BFL + BCA + ADN, 1:2:1 | 20 uL | 1 uL | | 2 uL | 1 uL | 488 | | | |
| | | | | | | 380 | | | |

Example 7

Figure 27A:
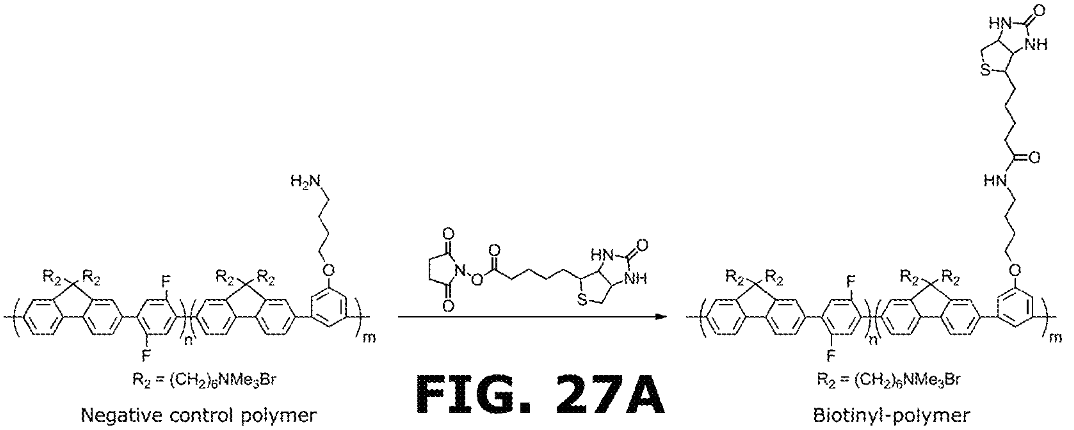
FIG. 27A. Schematic of the structure relating to biotinylation of one embodiment of the invention.
Figure 27B:
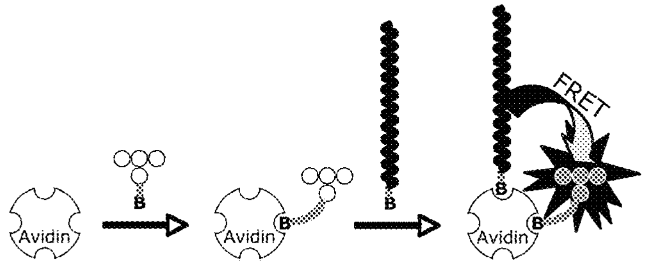
FIG. 27B. Schematic of a biotin-avidin binding assay of the invention.
Figure 27C:
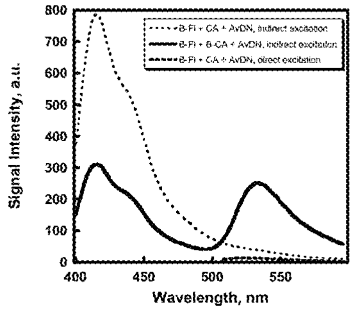
FIG. 27C. Plot of the fluorescence spectra relating to a biotin-avidin binding assay for one embodiment of the invention.

Analysis of Amplification of Signal by Biotinyl-CA001, Avidin DN, and Biotinyl-Fluorescein:

FIG. 27A shows the biotinylation of CA001. The amine polymer CA001 (precursor to the biotinyl polymer) should not bind avidin, and is used as the negative control polymer. FIG. 27B depicts the assay schematically. The biotinylated dye and polymer are brought together specifically by biotin-avidin binding. The negative control polymer (amine polymer CA001, noted as CA) should not bind the avidin. FIG. 37C shows the fluorescence spectra resulting from the assay followed in the above protocol (Example 6). The dotted line shows the fluorescence spectra upon excitation at 380 nm of nonspecific polymer (CA) in solution with Avidin DN (AvDN) and biotinylated fluorescein (B-Fl). Only polymer emission, centered at 420 nm, is observed. The solid line shows the fluorescence spectra upon excitation at 380 nm of biotinylated polymer (BCA) in solution with Avidin DN (AvDN) and biotinylated fluorescein (B-Fl). Strong energy transfer is observed, resulting in additional emission arising from the fluorescein, centered at 530 nm. FRET occurs only for biotinyl-CA001, indicating that the donor biotinyl-CA 001 and acceptor fluorescein are brought into close proximity via biotin-avidin binding. This corroborates the biotinylation CA001 following the Pierce procedure (Example 5). Direct excitation of the dye at 488 nm is shown as a dashed line. Comparison of the dashed line with the solid line reveals 19-fold amplification of the dye when excited indirectly (via FRET) versus directly.

Example 8

Synthesis of Cationic Conjugated Polymer Precursor with a Carboxylate Functional Group, CC001:

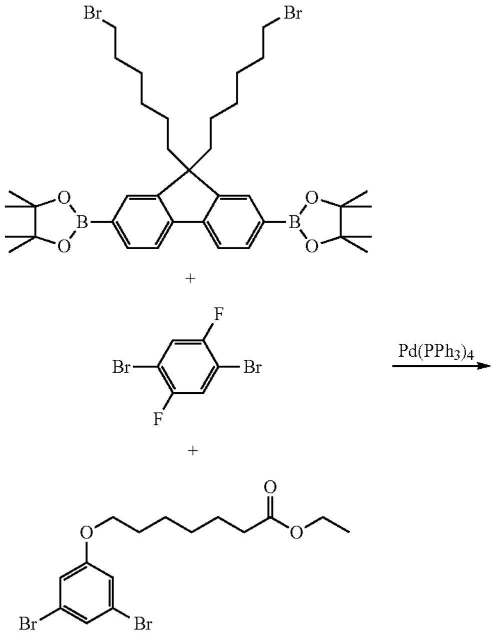

-continued

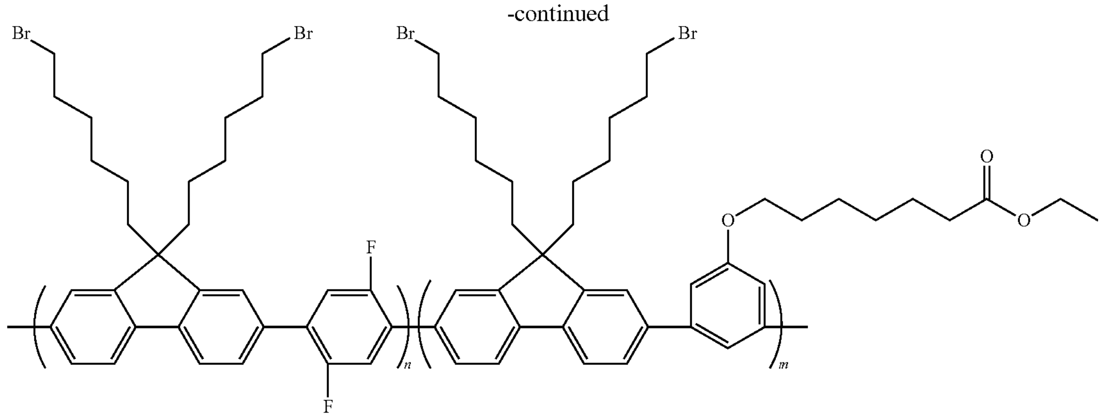

Poly[2,7-{9,9-bis(6'-bromohexyl)}fluorene-co-alt-1,4-{2,5-difluoro}phenylene)-co-(2,7-{9,9-bis(6'-bromohexyl)}fluorene-co-alt-3,5-1-(7'-ethylesterheptoxy)phenylene)]: A solution of 2,7-(4,4,5,5-tetramethyl-1,3,2-dioxaborolan-2-yl)-9,9-bis(6'-bromohexyl)fluorene (500 mg, 0.670 mmol), 1,4-dibromo-2,5-difluorobenzene (173.2 mg, 0.637 mmol), 1-(7'-ethylesterheptoxy)-3,5-dibromobenzene (13.6 mg, 0.033 mmol), potassium carbonate (1.12 g, 8.12 mmol), and tetrakis(triphenylphosphine)palladium (0) (21 mg, 0.018 mmol) in THF (15 mL) and water (5 mL) in a 50 mL round-bottomed flask equipped with a water-jacketed reflux condenser was degassed via four freeze-pump-thaw cycles, with argon being introduced after the third and fourth round of degassing. The solution was then heated to reflux for 48 hours under an argon atmosphere. After cooling, the solution was added dropwise to 40 mL of stirring methanol to precipitate the polymer, which was collected by centrifugation. This was followed by decanting and washing with methanol (twice) to remove low molecular weight fractions, yielding a pale yellow, fluffy powder. 1H NMR (CD2Cl2): 7.887-7.406 (m, 8H); 3.322 (t, J=6.6 Hz, 4H); 2.080 (br s, 4H); 1.710 (t, J=7.0 Hz, 4H); 1.269 (br s, 4H); 1.158 (br s, 4H); 0.799 (br s, 4H). Mn 39.5K, PDI 2.1.

Figure 28:
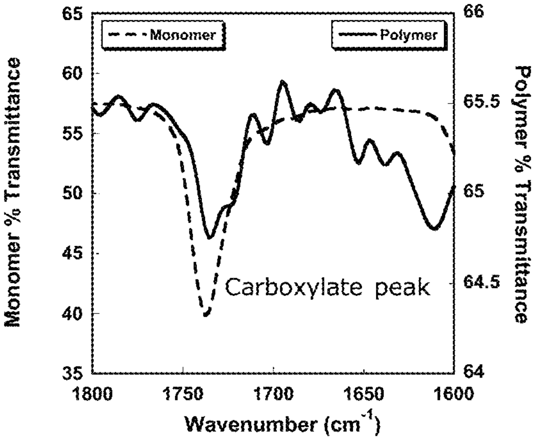
FIG. 28. Plot of an infrared (IR) spectroscopic analysis of another embodiment of the invention.

IR spectroscopy was used to evaluate the incorporation of the functionalized monomers into the final polymer structures. The carboxylate functional groups were protected as esters during the polymerization reaction to prevent catalyst contamination. This protecting group has a unique signature in infrared (IR) spectroscopy, as shown in FIG. 28. The peaks shown correspond to unique C=O peaks only present for the carboxylate protecting group. The dashed line in FIG. 28 corresponds to the IR spectra of the monomer, whereas the solid line corresponds to the IR spectra of the polymer. In both cases, a carboxylate peak is observed, indicating incorporation of the functional monomer.

Example 9

Synthesis of an Anionic Conjugated Polymer with an Amine Functional Group, AA003:

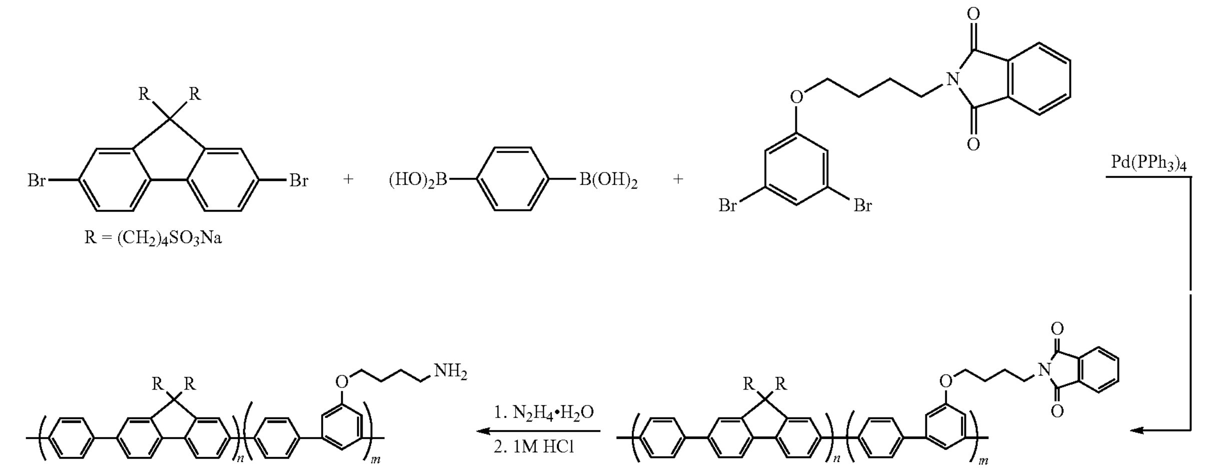

Poly[(2,7-{9,9-bis(4'-(sodiumsulfonate)butyl)}fluorene-co-alt-1,4-{2,5-difluoro}phenylene)-co-(2,7-{9,9-bis(4'-(sodiumsulfonate)butyl)}fluorene-co-alt-3,5-1-(4'-phthalimidobutoxy)phenylene)]: A solution of 2,7-dibromo-9,9-bis(4'-(sodiumsulfonate)butyl)fluorene (129.5 mg, 0.202 mmol), 1,4-diboronic acid (37.4 mg, 0.225 mmol), 1-(4'-phthalimidobutoxy)-3,5-dibromobenzene (10.4 mg, 0.023 mmol), potassium carbonate (366 mg, 2.65 mmol), and tetrakis(triphenylphosphine)palladium (0) (8.8 mg, 0.008 mmol) in DMF (20 mL) and water (20 mL) in a 100 mL round-bottomed flask equipped with a water-jacketed reflux condenser was degassed via four freeze-pump-thaw cycles, with argon being introduced after the third and fourth round of degassing. The solution was then heated to reflux for 48 hours under an argon atmosphere. Over the course of the reaction, a black precipitate formed. After cooling, the solution was removed and the precipitate was washed with acetone to give a brown powder, 1H NMR (DMSO): 7.910-7.597 (m, 10H); 2.206 (br s, 8H); 1.400 (br s, 4H); 0.668 (br s, 4H). IR: 1696 cm-1, indicating a protected amine (phthalimide).

AA003, Poly[(2,7-{9,9-bis(4'-(sodiumsulfonate)butyl)}fluorene-co-alt-1,4-{2,5-difluoro}phenylene)-co-(2,7-{9,9-bis(4'-(sodiumsulfonate)butyl)}fluorene-co-alt-3,5-1-(4'-aminobutoxy)phenylene)]: A solution of hydrazine monohydrate (29.9 mg, 0.598 mmol) and poly[(2,7-{9,9-bis(4'-(sodiumsulfonate)butyl)}fluorene-co-alt-1,4-{2,5-difluoro}phenylene)-co-(2,7-{9,9-bis(4'-(sodiumsulfonate)butyl)}fluorene-co-alt-3,5-1-(4'-aminobutoxy)phenylene)] (45 mg, 0.081 mmol) in 50% methanol/water (5 mL) were refluxed for 5 hours. After cooling to room temperature, the pH of the solution was adjusted to 3 with 1M HCl, then refluxed for an additional 2 hours. After cooling and transfer to a 15 mL Falcon tube, AA003 was purified by the following protocol.

Purifying Deprotected AA003

Purpose:

To enrich for amine-activated anionic polymer

Materials:

UV-transparent plastic 1-mL cuvettes centrifuge

UV-Vis spectrophotometer pipeters+tips

NaOH, 1.0 M, 0.1 mL:

| | |
|---|---|
| NaOH, 10M | 10 uL |
| H2O | 90 uL |

Crude AA003

90% MeOH, 1% T20 (90M1T, 50 mL)

MC30 filters

Procedure:

1. Sort out fractions:

1a) If there is a film lining the inside of the tube (precipitated polymer), pour off the supernate into a new tube. Using a pipet tip, remove all the supernate completely, and set it aside.

1b) Process the film (ppt) lining the tube:

i. Add 0.5 mL water and check pH by litmus. If necessary, neutralize to pH ~7-8 by adding NaOH (1-5 uL amounts of 0.1M NaOH at first, then of 1.0 M NaOH if more practical), mix, pellet, check on litmus. Go through several add-mix-pellet-check pH test cycles until pH 8 is maintained.

ii. Remove water extract, and place in a 1.5 mL eppi.

iii. Spin @14 krcf, 2'. Save sup. and pellet.

iv. Lyophilize pellet.

1c) Process the supernate from step 1a):

i. Sample 0.5 mL of supernate (usually a suspension) and place in a 1.5 mL eppi.

ii. Test pH by litmus and record pH.

iii. Neutralize to pH ~7-8 as in step 1b1 above.

iv. Centrifuge @14 krcf, 2'.

v. Separate sup. from pellet, keeping both.

vi. Lyophilize pellet.

vii. Re-suspend pellet in minimal amt. of anhydrous DMSO.

viii. Perform UV/V is spec. in water, record absorbance and calculate concentration of all fractions, using valid Ext. Coef.

2. Desalt by MC30.

Figure 29:
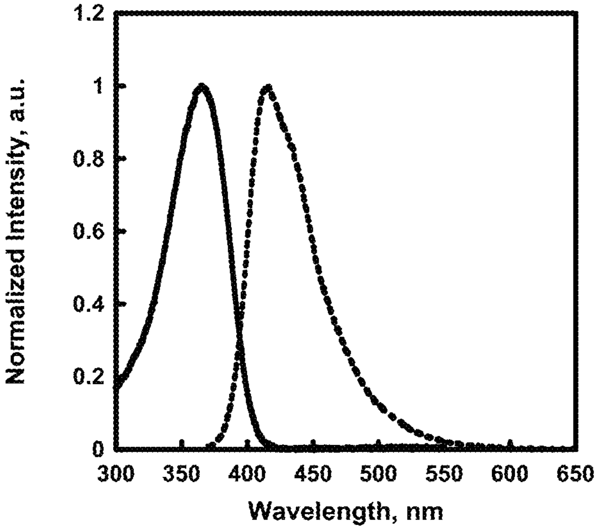
FIG. 29. Plot of the optical spectra of another embodiment of the invention.

The optical spectra of AA003 are shown in FIG. 29, where the solid line indicates the absorption and the dashed line indicates the emission spectra. The deprotected polymer AA003 (having a free amine) was reacted with a succimidyl ester FAM, 5(6)FAM-SE (Invitrogen, #C1311), adapted from protocols available at www.invitrogen.com (last visited Oct. 4, 2007). As a negative control, the same polymer was incubated with fluorescein (no reactive group) under the same reaction conditions. The protocol for this procedure analogously follows that of Example 4.

Example 10

Synthesis of Anionic Conjugated Polymer with a Maleimide Functional Group, AA003-M01:

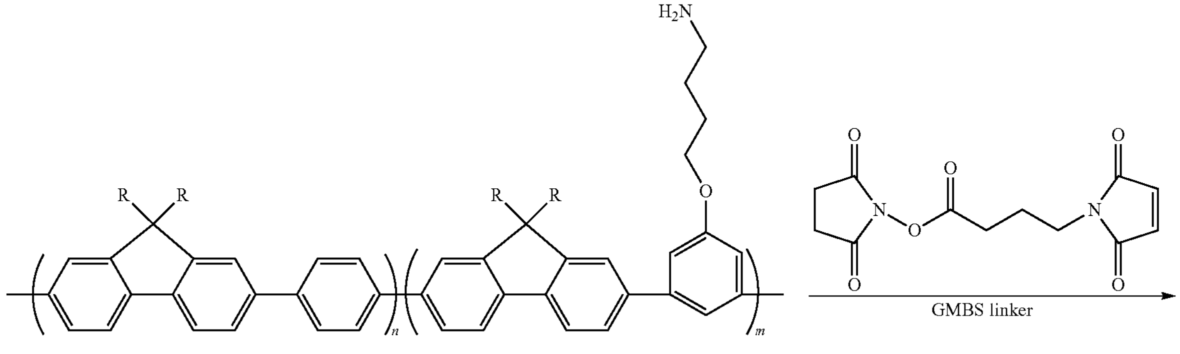

R = $(CH_2)_4SO_3Na$

AA003

-continued

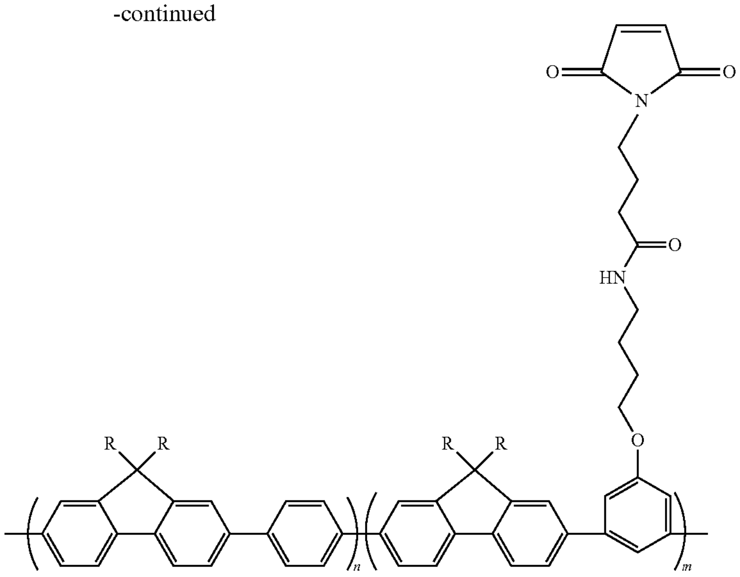

R = $(CH_2)_4SO_3Na$
AA003-M01

The amine functionality on a multichromophore can be converted to other functionalities with the use of a dual-functional linker, such as GMBS. This strategy was taken to convert AA003 to AA003-M01. The protocol for this procedure was modified from the Pierce protocol, found on the Pierce website, www.pierce.net.com (last visited Sep. 23, 2007). The protocol used can be found below.

Conjugation of GMBS to AA003

Purpose:

To functionalize AA003 with GMBS to give a maleimide moiety

Materials:

Centrifuge

UV-Vis spectrophotometer

UV-transparent, 1-mL cuvettes pipeters+tips

AA003

GMBS (Pierce #22309)

90% MeOH, 1% T20 (90M1T, 50 mL)

DMSO

NEt3

MC30 filters

Procedure:

1. To functionalize AA003 with Maleimide, here are useful amounts to use:

1a) For 40× XS, use 0.3 mM polymer and 12 mM GMBS. This means 3.0 nmol polymer/10 uL rxn as follows:

| Sample | Rxn. Vol. | 90% M1T | DMSO | AA003 | 0.5M NEt3 | GMBS, 120 mM |
|---|---|---|---|---|---|---|
| AA003 + G | 10 uL | 5.7 uL | — | 2.3 uL | 1.0 uL | 1.0 uL |
| AA003 − G | 10 | 5.7 | 1.0 uL | 2.3 uL | 1.0 | — |

2. When all reagents but linker have been combined:

2a) Dissolve GMBS in DMSO (Use GMBS without delay after dissolving):

i. 120 nM GMBS=3.4 mg/0.1 mL DMSO, or 30 uL/mg

2b) Incubate to 25 C on heat block for 30 min. Check for clarity.

3. Remove XS GMBS by MC30:

3a) Before applying to MC cup, dilute DMSO to <5%

3b) Separately combine each reaction w/400 uL 90M1T

3c) Apply to cup

3d) Spin 10 mins @14 k ref

3e) Determine if more time spinning is necessary by estimating volume of retentate 3f) Discard filtrate 3g) Add 400 uL more 90M1T and repeat spin 3h) If rerentate looks nearly dry, add 20 uL 90M1T and swirl a hit in cup 3i) Invert and spin to collect retentate 3j) Measure final retentate volumes=______uL 3k) Determine concentration by UV-vis, then adjust final concentration to 25 uM in 0.5×90M1T.

Example 11

Synthesis of Anionic Conjugated Polymer Fluorescein Conjugate, AA003-M01.-Fl:

The maleimide functional group on AA003-M01 was tested for thiol reactivity by reacting with SAMSA-fluorescein (Invitrogen) using protocols adapted from www.invitrogen.com (last visited Oct. 4, 2007). AA003 was used as a negative control. The modified protocol can be found below.

SAMSA Assay for Maleimide

Purpose: To demonstrate AA003-M01 has an active maleimide moiety using 10× XS SAMSA-fluorescein to AA003-M01

Materials:

Centrifuge

UV-transparent, 1-mL cuvettes

Fluorometer, model PE-LS55
pipeters+tips
potassium phos, 0.5M, pH 7.0, 0.2 mL:

| | |
|---|---|
| K2HPO4, 1M | 62 uL |
| KH2PO4, 1M | 39 uL |
| H20 | 100 uL |

HCl, 6 M, 0.2 mL:

| | |
|---|---|
| H2O | 0.1 mL |
| HCl, 12M | 0.1 mL |

NaOH, 0.1 M, 1 mL:

| | |
|---|---|
| NaOH, 10M | 10 uL |
| H2O | 990 uL |

AA003
AA003-M01
SAMSA-fluorescein (invitrogen, product A685)
MC30 filters

Procedure:

1. Prepare 1.0 mM deprotected SAMSA:
1a) Dissolve 1.0 mg SAMSA/95 uL of 0.1 M NaOH (20 mM SAMSA)
1b) Incubate at RT for 15 mins to remove acetyl protecting group
1c) Neutralize with 6 M HCl: 1.4 uL/mg SAMSA (20 mM SAMSA)
1d) Buffer with 20 uL 0.5M sodium phos, pH 7/mg SAMSA (16 mM SAMSA)
1e) Dilute 16-Fold to 1.0 mM SAMSA with water.
2. Setup rxns by adding:
2a) For AA003-M01: 10 uL of deprotected SAMSA to 10 uL of 25 uM AA003+GMBS (3.k+G from protocol in Example 10)

2b) For AA003: 10 uL of 1.0 mM deprotected SAMSA to 10 uL of 25 uM AA003−GMBS (3.k-G from protocol in Example 10)
3. Incubate on heat block @25 C, 30 mins
4. Remove XS SAMSA by MC30:
4a) Before applying to MC cup, dilute DMSO to <5%
4b) Separately combine each rxn w/400 uL 90N1ET
4c) Apply to cup
4d) Spin 10 mins @14 k ref
4e) Determine if more time spinning is necessary by est vol of retentate
4f) Discard filtrate
4g) Add 400 uL more 90M1T and repeat spin
4h) If retentate looks nearly dry, add 20 uL 90M1T and swirl a bit in cup
4i) Invert and spin to collect retentate
5. Analyze fluorescence @488 and 380 excitation of both AA003-M01 and AA003 samples from step 4.i.

FIG. 30C shows the results from this assay. AA003-M01 (FIG. 30B noted as Maleimide-functionalized polymer) and a negative control polymer (no maleimide, AA003 FIG. 30A noted as Negative control polymer) were reacted with a thiolated fluorescein (SAMSA-fluorescein) according the above procedure. The maleimide-functionalized polymer AA003-M01 reacts with the thiolated fluorescein, and becomes covalently bound to the fluorescein, ensuring a fixed distance between the donor polymer and the acceptor dye. Thus, excitation of the polymer results in FRET to the acceptor dye, and intense dye emission is observed (solid line, FIG. 30C). The negative control does not covalently bind fluorescein, and when the polymer is excited, only polymer emission is observed (dotted line, FIG. 30C).

Example 12

Synthesis of a Biotinylated Anionic Conjugated Polymer, Biotinyl-AA003:

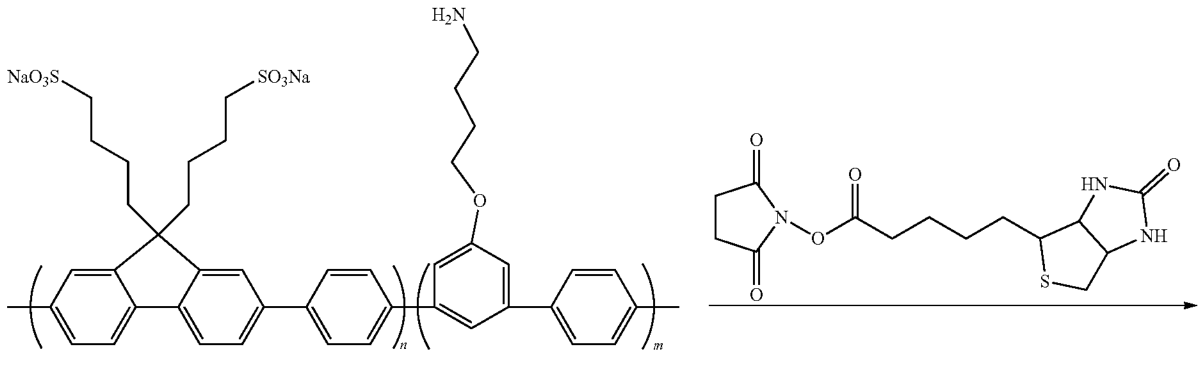

AA 003

-continued

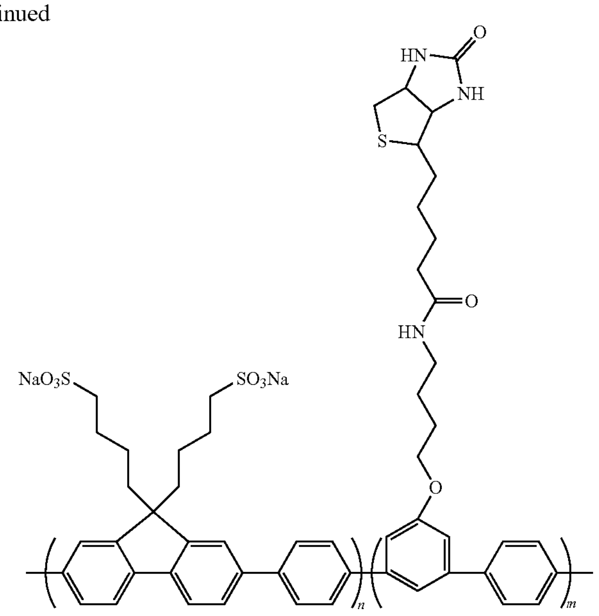

Biotinyl-AA003

The amine functionality on AA003 was converted to a biotin using an NHS-biotin linker available from Pierce (#20217). The protocol for this procedure was modified from the Pierce protocol, found on the Pierce website, www.piercenet.com (last visited Sep. 23, 2007). The protocol used can be found below.

Procedure for the Conjugation of NHS-Biotin to AA003

Purpose:

To biotinylate AA003 with NHS-Biotin.

Materials:

Fluorometer, with UV-transparent cuvettes

UV-VIS instrument

Purified AA003 (AA3)

NHS-biotin (Pierce #20217)

0.5 M NEt3 (1:14 dilution of stock (7.2M) NEt3)

DMSO

MC30 filters

Procedure:

1. Set up reactions, 0.5 mM polymer and 20 mM NHS-biotin:

| Sample | uL Rxn | 90% M1T | DMSO | AA3, 5.0 nmol/ 10 ul | 0.5M NEt3 | NHS-biotin, 200 mM |
|---|---|---|---|---|---|---|
| PC: CA1 + Biot | 10 | 6.8 uL | — | 1.2 uL | 1.0 uL | 1.0 uL |
| NC: CA1 − Biot | 10 | 6.8 | 1.0 uL | 1.2 uL | 1.0 | — |
| AA3 + B | 40 | 0 | — | 38 uL | 4.0 | 4.0 uL |
| AA3 + B | 10 | 0 | 1.0 | 9.6 uL | 1.0 | — |
| 2b3SUP + B | 35 | 0 | — | 34 uL | 3.5 | 3.5 uL |
| 2b3SUP − B | 10 | 0 | 1.0 | 9.8 uL | 1.0 | — |
| 2b3PEL + B | 70 | 20 | — | 36 uL | 7.0 | 7.0 uL |
| 2b3PEL − B | 10 | 2.9 | 1.0 | 5.1 uL | 1.0 | — |

2. When all but biotin has been combined, dissolve 1-2 mgs of NHS-biotin in DMSO at 15 uL anhydrous DMSO/mg NHS-biotin (or 1.7 mg/0.025 mL; 200 mM). Use NHS-reagents without delay after dissolving.

3. Incubate to 25 C on heat block for 30 min.

4. Dilute 1:100 in 90M1T (1 uL in 100, or 4 in 400 uL)

5. Desalt by MC30, 2X

6. Assay for concentration by UV/V is

Example 13

Procedure for Amplification of Signal by Bio-AA003 and Avidin D-Fluorescein:

Purpose:

To demonstrate specific fluorescent signal via FRET using biotinyl-AA003 and Avidin D-Fluorescein.

Materials:

Fluorometer (NanoDrop or Perkin-Elmer PE-LS55)

UV-transparent plastic 1-mL cuvettes pipeters+tips biotinyl-AA003 (BAA)

AA003 (AA)

Avidin D-Fluorescein (A-Fl)

TBS

Procedure:

1. In an eppendorf tube, combine reagents as listed in table below. Incubate for five minutes, then dilute combinations 100-fold prior to measurement on a fluorometer, either 1 uL, in 100 uL for the NanoDrop, or 10 uL in 1 mL cuvette for a benchtop fluorometer.

2. Directly excite A-Fl at 488 nm as well as indirectly via FRET by exciting the polymer at 380 nm.
3. Collect data on peak heights at relevant wavelengths. Subtract background from peak heights, including these sources
   3a) Buffer alone control
   3b) Polymer peak tail (~5%) from FRET to fluorescein peaks

| | TBS | A-Fl 5 uM | AA 5 uM | BAA 5 uM | Exc. (nm) | 415 nm pk. ht. | 566 nm pk. ht. | 533 nm pk. ht. |
|---|---|---|---|---|---|---|---|---|
| TBS only | 20 uL | | | | 550 | — | | |
| | | | | | 380 | | | |
| AA only | 20 uL | | 3 uL | | 380 | | | |
| AA + A-Fl 6:1 | 20 uL | 0.5 uL | 3 uL | | 550 | | | |
| | | | | | 380 | | | |
| BAA only | 20 uL | | | 3 uL | 380 | | | |
| BAA + A-Fl 6:1 | 20 uL | 0.5 uL | 3 uL | 3 uL | 488 | | | |
| | | | | | 380 | | | |

Example 14

Figure 31A:
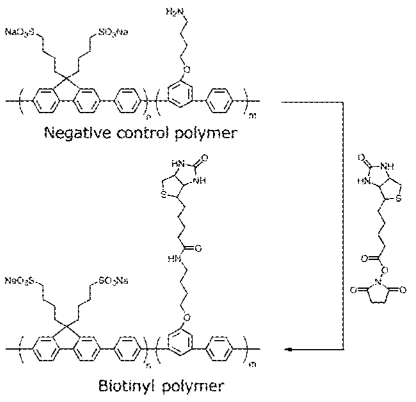
FIG. 31A. Schematics of control polymer and experimental polymer structures relating to one embodiment of the invention.
Figure 31B:
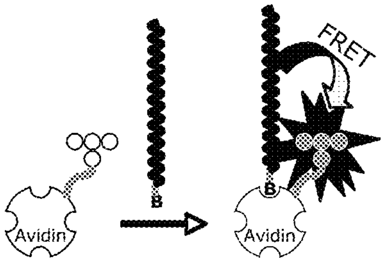
FIG. 31B. Schematic of a fluorescence assay relating to control and experimental polymers.

Analysis of Amplification of Signal by Biotinyl-AA003 and Fluorescein-Labeled Avidin D:

This assay is described procedurally in Example 13. A scheme of this assay is shown in FIG. 31B, Biotinyl-AA003 (see FIG. 31A noted as Biotinyl polymer) is incubated with fluorescein-labeled Avidin D. As a negative control, the amine polymer AA003 (see FIG. 31A noted as Negative control polymer) is incubated with fluorescein-labeled Avidin D in a similar manner. In each case, the polymer is excited, and fluorescein emission observed. For the negative control AA003, only polymer emission (centered at 420 nm) is observed, whereas for the biotinyl-AA003, strong dye emission is observed.

Figure 32A:
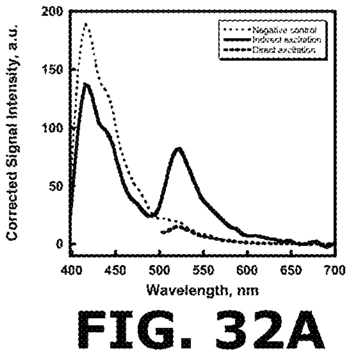
FIG. 32A. Plot of the fluorescence spectra for one embodiment of a polymer of the invention.
Figure 32B:
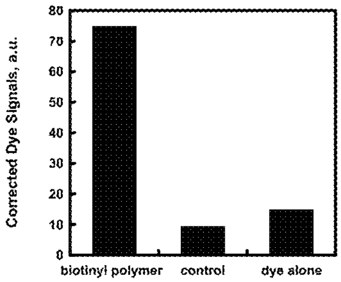
FIG. 32B. Plot showing corrected values for fluorescence spectra of one embodiment of the invention.

Results from this assay are shown in FIGS. 32A-B. The biotinyl-AA003 was tested with Avidin D containing 4 dyes per avidin. Signals from the control polymer and the dye alone were also recorded and are presented in FIGS. 32A-B. FIG. 32A shows the resulting fluorescence spectra. The dye signals at 523 nm from this data set are summarized in FIG. 32B.

These data indicate the fluorescein signal (at 523 nm) is amplified in the presence of the polymer (FIG. 32A, solid vs dashed spectra, left and biotinyl-AA003 vs dye alone, right) and the signals observed were due to specific polymer-Avidin D complexes (FIG. 32A, solid vs dotted spectra, left and biotinyl-polymer vs control, right). The amine polymer control (no biotin) was not able to bind the avidin and thus minimal energy transfer was observed (88% specificity). Specificity is defined as 1-(control signal/specific dye signal). The right figure illustrates the difference in dye signal with and without polymer and between the positive and negative control samples. The data presented in FIG. 32B are corrected for signals arising from buffer and polymer tail. The polymer tail contribution at 523 nm is 5% of the polymer peak height at 419 nm.

Example 15

Amplification Effects of Varying Dye:Avidin D Ratios:

Different ratios of polymer to dye were tested. This was evaluated using Avidin D conjugates from Vector Laboratories which contained an average of 0.8, 1.5 and 4 fluorescein dyes per avidin. As the number of dyes is increased the ratio of extinction coefficients (absorbance) between the polymer and dye is decreased. It was therefore predicted that for this set of fluorescein-labeled Avidin D, the best amplification values would be observed for the avidin conjugates containing the lowest number of dyes. Polymer concentration was held constant at two equivalents of polymer per Avidin D.

Figure 33A:
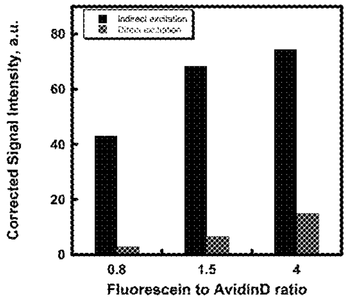
FIG. 33A. Plot of the fluorescence signal intensity for a polymer of one embodiment of the invention.
Figure 33B:
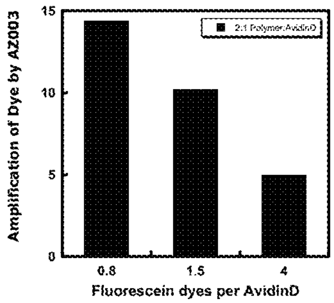
FIG. 33B. Plot of signal amplification relating to a polymer of one embodiment of the invention.

The data shown in FIGS. 33A-B indicate a dependence on the ratio of polymer to dye as was expected. This ratio was varied by increasing the number of dyes per Avidin D at constant polymer and avidin concentrations. The data indicate that as the ratio of dye:avidin increases from 0.8 to 4 as the signal intensity of the dye increases (FIG. 33A) while the observed amplification drops (FIG. 33B). As the number of dyes increases, so does the direct dye signal due to the higher absorbance and thus higher fluorescence (gray bars, FIG. 33A).

Example 16

Synthesis of Anionic Conjugated Polymer with an Amine Functional Group, AA002, Capable of 405 nm Excitation:

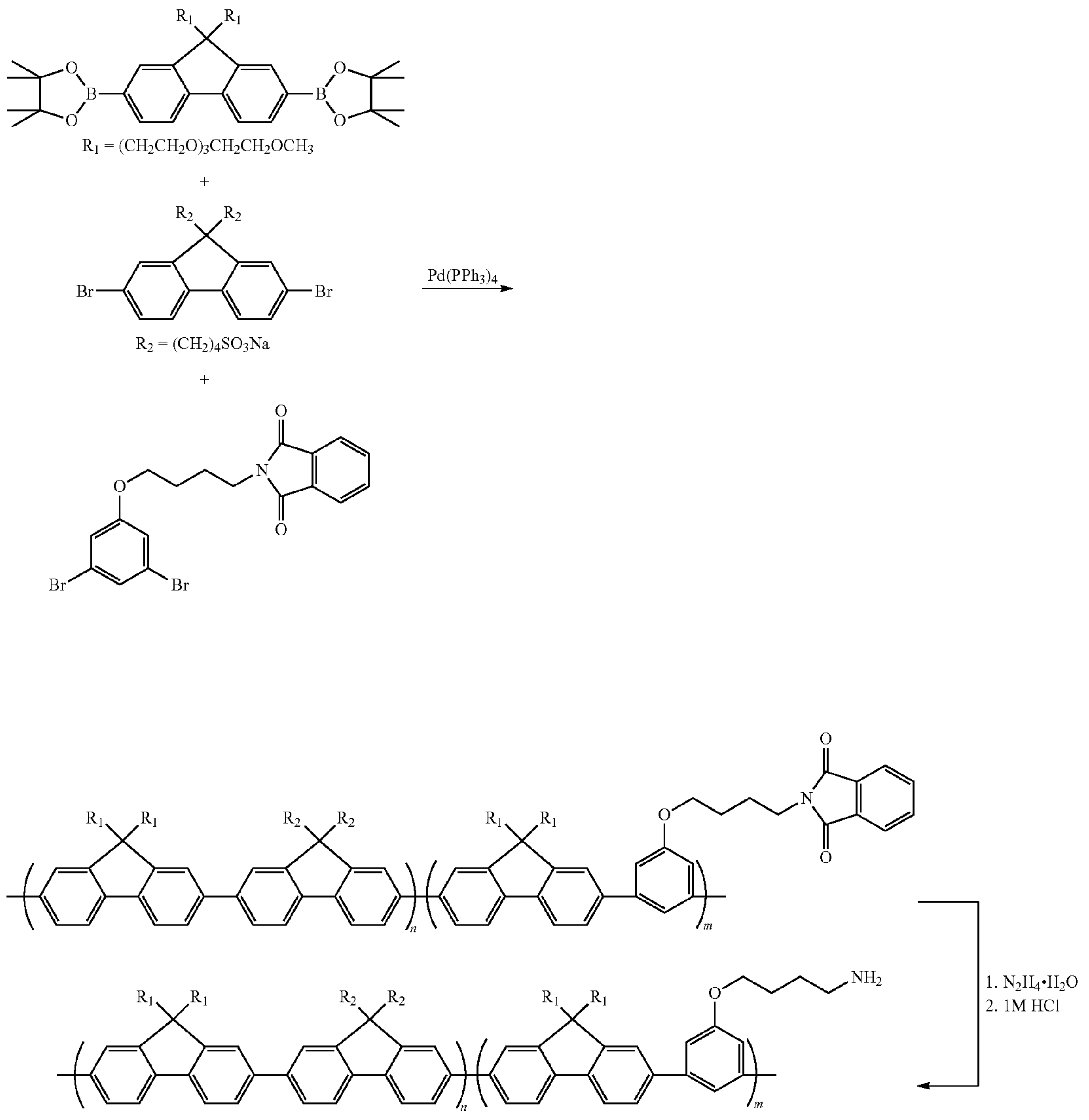

Poly[2,7-{9,9-bis(1-(2-(2-methoxyethoxy)ethoxy)ethoxy)))}-co-alt-(2,7-{9,9-bis(4'-(sodiumsulfonate)butyl)}fluorene-co-2,7-{9,9-bis(1-(2-(2-methoxyethoxy)ethoxy)ethoxy)))}-co-alt-3,5-1-(4'-phthalimidobutoxy)phenylene)]: A solution of 2,7-(4,4,5,5-tetramethyl-1,3,2-dioxaborolan-2-yl)-9,9-bis(1-(2-(2-methoxyethoxy)ethoxy)ethoxy)))fluorene (120.1 mg, 0.150 mmol), 2,7-dibromo{9,9-bis(4'-(sodiumsulfonate)butyl)}fluorene (91.3 mg, 0.143 mmol), 1-(4'-phthalimidobutoxy)-3,5-dibromobenzene (3.7 mg, 0.0082 mmol), potassium carbonate (234 mg, 1.7 mmol), and tetrakis(triphenylphosphine)palladium (0) (6.2 mg, 0.0054 mmol) in DMF (3.8 mL), THF (2.5 mL), and water (2.5 mL) in a 48 mL Schlenck tube was degassed via sparging with argon for 20 minutes. The solution was then heated to 85° C. for 3 days under an argon atmosphere. The solution was added drop wise into stirring acetone to give a dark brown solid. The solid was then stirred with methanol, the filtrate collected, and the solvent removed to yield a bright yellow solid. 1H NMR (DMSO): 8.055-7.828 (m, 12H); 3.558-3.293 (m, 24H); 3.188 (m, 12H); 2.217-2.161 (m, 8H); 1,417 (Iv s, 4H); 0.664 (br s, 4H). Bimodal, Mn 7.3K, PD1 1.02, and Mn 49K, PDI1.2.

Figure 34:
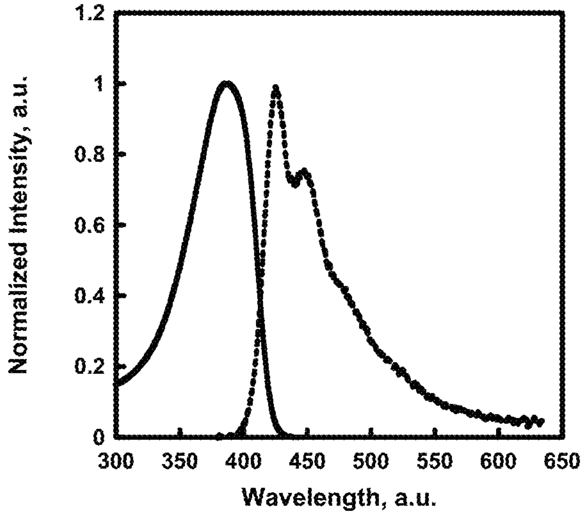
FIG. 34. Plot of the optical spectra of a further embodiment of the invention.

This polymer was then deprotected and purified to give AA002, using procedures analogous to those noted in Example 9. The optical spectra for AA002 are shown in FIG. 34, where the solid line indicates the absorption and the dashed line indicates the emission spectra.

Example 17

Synthesis of a Biotinylated Conjugated Polymer, Biotinyl-AA002:

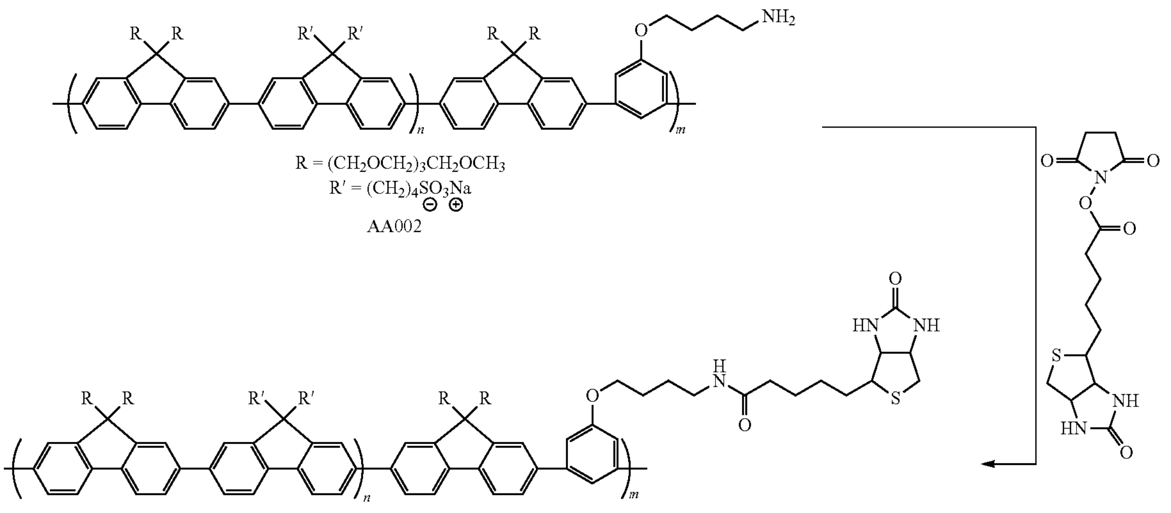

R = $(CH_2OCH_2)_3CH_2OCH_3$
R' = $(CH_2)_4SO_3Na$
AA002

R = $(CH_2OCH_2)_3CH_2OCH_3$
R' = $(CH_2)_4SO_3Na$
Biotinyl-AA002

The amine functionality on AA002 was converted to a biotin functionality using an NHS-biotin linker available from Pierce (#20217). The protocol for this procedure was modified from the Pierce protocol, found on the Pierce website, www.piercenet.com (last visited Sep. 23, 2007). The protocol for this procedure analogously follows that noted in Example 12.

Example 18

Amplification Effects of Varying Polymer:Avidin D Ratios

Figure 35A:
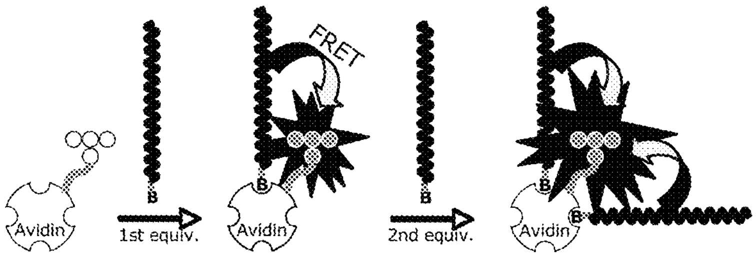
FIG. 35A. Schematic of a biotin-avidin binding assay of the invention.
Figure 35B:
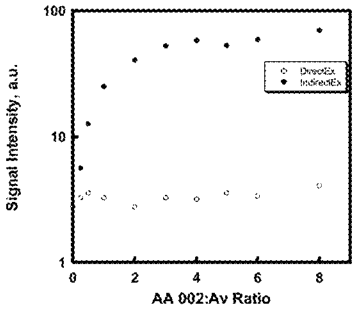
FIG. 35B. Plot of fluorescein emission for one embodiment of the invention.

Fluorescein-labeled Avidin D, or Avidin D-Fl (0.8 dyes per avidin), held at a constant concentration, was incubated with a series of increasing biotinyl-AA002 concentrations ranging from 0 to 8 equivalents. This is shown schematically in FIG. 35A for the first two equivalents of biotinyl-AA002. For each ratio, dye fluorescence was recorded for direct and indirect excitation (via FRET). As the polymer to dye ratio increased, signals arising from direct excitation remained fairly constant, whereas the signals arising from indirect excitation increased, as shown in FIG. 35B a plot of fluorescein emission as a function of the ratio of AA002 to Avidin D-Fl. A plateau of this increase in signal was reached at roughly four equivalents of biotinyl-AA002, consistent with the occupation of all the biotin binding sites on the Avidin D.

These data are consistent with the specific binding; biotinyl-AA002 to fluorescein-labeled Avidin D. High signal amplification is observed, which plateaus at four equivalents of polymer, indicating the occupation of all available biotin binding sites.

Example 19

Electrostatic Amplification of Dye Signals

Figure 36A:
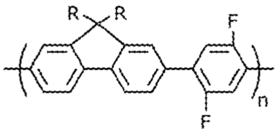
FIG. 36A. Schematic of a polymer structure relating to one embodiment of the invention.
Figure 36B:
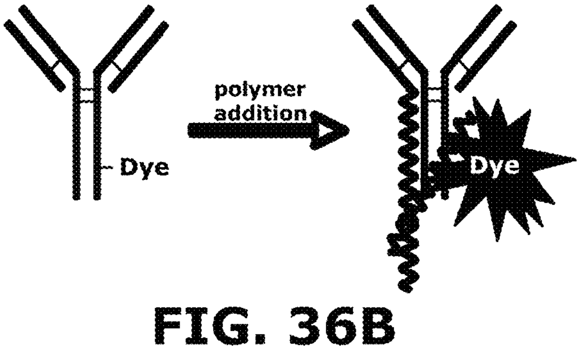
FIG. 36B. Schematic of a fluorescence assay relating to a polymer of one embodiment of the invention.
Figure 36C:
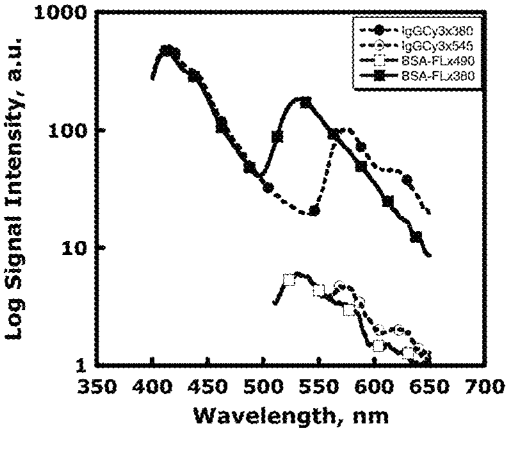
FIG. 36C. Plot of the fluorescence spectra for one embodiment of a polymer of the invention.

As shown schematically in FIG. 36B, dye-labeled proteins (Cy3-labeled IgG and fluorescein-labeled BSA) were each independently incubated with cationic polymer FFP-2F (see FIG. 36A). Nonspecific electrostatic association occurred between the polymer and each dye-labeled protein. Each solution was excited at 380 nm, and the emission spectra collected. These spectra were compared with the emission spectra collected from direct excitation of the dye, as shown in FIG. 36C indicating 30-fold amplification of Cy3-labeled IgG and 25-fold amplification of fluorescein-labeled BSA. The Cy3 labeled IgG used was an anti-digoxigenin antibody which is used to target digoxigenin labeled antibodies.

While preferred embodiments of the present invention have been shown and described herein, it will be obvious to these skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of assaying a sample for a target, the method comprising:

contacting the sample with a sensor for the target, wherein the sensor is capable of interacting with the target and is conjugated to a conjugated polymer having a linear backbone of TT-conjugated repeat units and comprising the structure:

$$-\!\!\left[\left[[CP_1]_a-[CP_2]_b\right]_m[CP_1]_a-[CP_3]_c\right]_n\!\!-$$

wherein:

$CP_1$ is a 2,7-linked fluorene repeat unit;

$CP_2$ is an aromatic repeat unit;

$CP_3$ is an aromatic repeat unit comprising the sensor or a bioconjugation functional group capable of covalently linking to the sensor, wherein at least one of the $CP_3$ comprises the sensor;

$CP_1$, $CP_2$ and $CP_3$ are different from one another and at least one of the $CP_1$, $CP_2$ or CPs repeat unit is linked by one single bond to at least one other of the $CP_1$, $CP_2$ or $CP_3$ repeat unit;

m is 1 to 10,000;

n is independently 1 to 10,000;

a, b and c are independently 1 to 250;

wherein $CP_1$, $CP_2$ and $CP_3$ are TT-conjugated repeat units randomly distributed along the conjugated polymer and the conjugated polymer does not comprise a biotin group; and wherein the sensor is selected from the group consisting of a protein, an antibody, a nucleic acid, an affinity ligand, a sugar, a lipid, and a peptide.

2. The method according to claim 1, wherein the conjugated polymer is substituted with a plurality of charge neutral water-soluble groups.

3. The method according to claim 1, wherein $CP_1$ and $CP_2$ are each independently substituted with one or more water-soluble groups.

4. The method according to claim 3, wherein the water-soluble groups comprise one or more groups selected from ethylene glycol oligomer, ethylene glycol polymer, ω-ammonium alkoxy salt and ω-sulfonate alkoxy salt.

5. The method according to claim 1, wherein the sensor is a protein, an antibody or a nucleic acid.

6. The method according to claim 5, wherein the sensor is an antibody.

7. A kit comprising:

a conjugated polymer covalently linked to a sensor, wherein the conjugated polymer has a linear backbone of TT-conjugated repeat units comprises the structure:

$$-\!\!\left[\left[CP_1\right]_a-\left[CP_2\right]_b\right]_m\!\!\left[\left[CP_1\right]_a-\left[CP_3\right]_c\right]_n\!\!-$$

wherein:

$CP_1$ is a 2,7-linked fluorene repeat unit;

$CP_2$ is an aromatic repeat unit;

$CP_3$ is an aromatic repeat unit comprising the sensor or a bioconjugation functional group capable of covalently linking to the sensor, wherein at least one of the $CP_3$ comprises the sensor;

$CP_1$, $CP_2$ and $CP_3$ are different from one another and at least one of the $CP_1$, $CP_2$ or CPs repeat unit is linked by one single bond to at least one other of the $CP_1$, $CP_2$ or $CP_3$ repeat unit;

m is 1 to 10,000;

n is independently 1 to 10,000;

a, b and c are independently 1 to 250;

wherein $CP_1$, $CP_2$ and $CP_3$ are TT-conjugated repeat units randomly distributed along the conjugated polymer and the conjugated polymer does not comprise a biotin group; and wherein the sensor is selected from the group consisting of a protein, an antibody, a nucleic acid, an affinity ligand, a sugar, a lipid, and a peptide.

8. The kit according to claim 7, wherein the conjugated polymer is substituted with a plurality of charge neutral water-soluble groups.

9. The kit according to claim 8, wherein $CP_1$ and $CP_2$ are each independently substituted with one or more water-soluble groups.

10. The kit according to claim 9, wherein the water-soluble groups comprise one or more groups selected from ethylene glycol oligomer, ethylene glycol polymer, ω-ammonium alkoxy salt and ω-sulfonate alkoxy salt.

11. The kit according to claim 7, wherein the sensor is a protein, an antibody or a nucleic acid.

12. The kit according to claim 11, wherein the sensor is an antibody.

13. The method according to claim 1, wherein CP1 comprises a substituted fluorene.

14. The kit according to claim 7, wherein CP1 comprises a substituted fluorene.

* * * * *